United States Patent
Ozaki et al.

(10) Patent No.: US 10,550,412 B2
(45) Date of Patent: Feb. 4, 2020

(54) METHOD OF PRODUCING LIPID

(71) Applicant: Kao Corporation, Chuo-ku, Tokyo (JP)

(72) Inventors: Tatsuro Ozaki, Wakayama (JP);
Takeshi Saito, Wakayama (JP);
Tadahiro Ozawa, Utsunomiya (JP)

(73) Assignee: Kao Corporation, Tokyo (JP)

( * ) Notice: Subject to any disclaimer, the term of this patent is extended or adjusted under 35 U.S.C. 154(b) by 414 days.

(21) Appl. No.: 15/317,345

(22) PCT Filed: Jun. 18, 2015

(86) PCT No.: PCT/JP2015/067581
§ 371 (c)(1),
(2) Date: Dec. 8, 2016

(87) PCT Pub. No.: WO2015/194628
PCT Pub. Date: Dec. 23, 2015

(65) Prior Publication Data
US 2017/0114376 A1   Apr. 27, 2017

(30) Foreign Application Priority Data

Jun. 20, 2014 (JP) .................. 2014-127378

(51) Int. Cl.
*C12P 7/64* (2006.01)
*C12N 9/16* (2006.01)
*C12N 15/70* (2006.01)
*C12N 15/79* (2006.01)

(52) U.S. Cl.
CPC .............. *C12P 7/6409* (2013.01); *C12N 9/16* (2013.01); *C12N 15/70* (2013.01); *C12N 15/79* (2013.01); *C12Y 301/02014* (2013.01)

(58) Field of Classification Search
None
See application file for complete search history.

(56) References Cited

U.S. PATENT DOCUMENTS

| | | | |
|---|---|---|---|
| 9,828,613 B2 | 11/2017 | Ozaki | |
| 10,066,248 B2 | 9/2018 | Sugihara et al. | |
| 10,087,428 B2 | 10/2018 | Ozaki et al. | |
| 2009/0317878 A1 | 12/2009 | Champagne et al. | |
| 2011/0217743 A1 | 9/2011 | Yoshida et al. | |
| 2013/0219557 A1 | 8/2013 | Kawahara | |
| 2015/0111254 A1 | 4/2015 | Ozaki et al. | |
| 2015/0247172 A1 | 9/2015 | Kawahara | |
| 2015/0307860 A1 | 10/2015 | Ozaki et al. | |
| 2016/0130615 A1 | 5/2016 | Ozaki et al. | |
| 2017/0044580 A1 | 2/2017 | Sugihara et al. | |
| 2017/0107545 A1 | 4/2017 | Togo et al. | |
| 2017/0335353 A1 | 11/2017 | Ozaki | |
| 2017/0335354 A1 | 11/2017 | Ozaki | |
| 2018/0135084 A1 | 5/2018 | Kawahara et al. | |
| 2018/0223299 A1 | 8/2018 | Sugihara | |
| 2019/0071698 A1 | 3/2019 | Sugihara | |

FOREIGN PATENT DOCUMENTS

| | | |
|---|---|---|
| JP | 07-501924 A | 3/1995 |
| JP | 11-505115 A | 5/1999 |
| JP | 2002-502263 A | 1/2002 |
| JP | 2011-147438 A | 8/2011 |
| JP | 2014-60943 A | 4/2014 |
| JP | 2014-132892 A | 7/2014 |
| JP | 2015-177771 A | 10/2015 |
| WO | WO 92/20236 A1 | 11/1992 |
| WO | WO 96/36719 A1 | 11/1996 |
| WO | WO 98/55633 A1 | 12/1998 |
| WO | WO 2011/108755 A1 | 9/2011 |
| WO | WO 2011/150410 A2 | 12/2011 |
| WO | WO 2012/061647 A2 | 5/2012 |
| WO | WO 2014/103930 A1 | 7/2014 |
| WO | WO 2015/005139 A1 | 1/2015 |
| WO | WO 2015/133305 A1 | 9/2015 |
| WO | WO 2016/021481 A1 | 2/2016 |
| WO | WO 2016/076231 A1 | 5/2016 |
| WO | WO 2016/088511 A1 | 6/2016 |
| WO | WO2017/183421 A1 | 10/2017 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Excerpted file history, U.S. Appl. No. 14/897,049, § 371 Date: Dec. 9, 2015, Non-final office action dated Mar. 15, 2017, from the United States Patent and Trademark Office, Alexandria, VA.
GenBank Database Accession No. AY835984 version AY835984.1, "Diploknema butyracea chloroplast palmitoyl/oleoyl specific acyl-acyl carrier protein thioesterase precursor (FatB) mRNA, partial cds; nuclear gene for chloroplast product," printed from www.ncbi.nlm.nih.gov/nuccore/61661996?sat=4&satkey=45297464, dated Mar. 13, 2017.
Sang, H., "Prospects for transgenesis in the chick," Mech Dev. Sep. 2004;121(9):1179-1186, Elsevier, Elsevier Ireland Ltd.
Excerpted file history, U.S. Appl. No. 15/110,635, § 371 Date: Jul. 8, 2016, preliminary amendment filed Sep. 26, 2016 and preliminary amendment filed Jul. 8, 2016 at the United States Patent and Trademark Office, Alexandria, VA.
Excerpted file history, U.S. Appl. No. 14/646,895, § 371 Date: May 22, 2015, amendment and reply filed Jul. 11, 2017 and non-final office action dated Feb. 13, 2017.
Excerpted file history, U.S. Appl. No. 14/897,049, § 371 Date: Dec. 9, 2015, amendment and reply filed Jul. 12, 2017.

(Continued)

*Primary Examiner* — Iqbal H Chowdhury
(74) *Attorney, Agent, or Firm* — Sterne, Kessler, Goldstein & Fox P.L.L.C.

(57) ABSTRACT

Provided is a method of producing a lipid, the method comprising the steps of:
introducing a gene encoding an acyl-ACP thioesterase into a host, and thereby obtaining a transformant, and
culturing the transformant, to produce the lipid.

20 Claims, 1 Drawing Sheet
Specification includes a Sequence Listing.

(56) References Cited

OTHER PUBLICATIONS

Excerpted file history, U.S. Appl. No. 15/317,347, § 371 Date: Dec. 8, 2016, preliminary amendment filed Dec. 8, 2016.
International Search Report (ISR) for PCT/JP2015/067581; I.A. fd Jun. 18, 2015, dated Sep. 1, 2015 from the Japan Patent Office, Tokyo, Japan.
International Preliminary Report on Patentability (IPRP), Chapter I of the Patent Cooperation Treaty, including the Written Opinion for PCT/JP2015/067581; I.A. fd Jun. 18, 2015, dated Dec. 20, 2016, by the International Bureau of WIPO, Geneva, Switzerland.
Nannochloropsis gaditana strain B-31 contig00219, whole genome shotgun sequence, [online], Feb. 14, 2014, database GenBank, AZIL01000370, protein id : EWM27855.1, [retrieval date Aug. 19, 2015], Internet<URL:http://www.ncbi.nlm.nih.gov/nuccore/AZIL01000370.
Tojo, T. et al., "Kokoyashi Yurai Acyl-ACP Thioesterase wa Chusa Shibosan no Seisan ni Kan' yo suru," ("Characterization of Acyl-ACP thioesterase derived from coconut"), [online], 2012, Japan Society for Bioscience, Biotechnology, and Agrochemistry 2012 Nendo Taikai Topic Sho Happyo Bango: 2C10a02, [retrieval date Aug. 20, 2015 (Aug. 20, 2015) ], Internet<URL: http://www.jsbba.or.jp/wp-content/uploads/file/award/2012/topics/7_2C10a02.pdf, Dynacom Co., Ltd.
Mayer, KM et al., "Identification of amino acid residues involved in substrate specificity of plant acyl-ACP thioesterases using a bioinformatics-guided approach," BMC Plant Biol. Jan. 3, 2007;7:1, DOI: 10.1186/1471-2229-7-1, 11 pages, BioMed Central, London, England.
Yuan, L et al., "The catalytic cysteine and histidine in the plant acyl-acyl carrier protein thioesterases," J Biol Chem. Feb. 16, 1996;271(7):3417-3419, American Society for Biochemistry and Molecular Biology, Baltimore, MD.
Yuan, L et al., "Modification of the substrate specificity of an acyl-acyl carrier protein thioesterase by protein engineering," Proc Natl Acad Sci U S A. Nov. 7, 1995;92(23):10639-10643, National Academy of Sciences, Washington, DC.
Voelker, TA et al., "Fatty acid biosynthesis redirected to medium chains in transgenic oilseed plants," Science. Jul. 3, 1992;257(5066):72-74, American Association for the Advancement of Science, Washington, DC.
Gong, Y et al., "Characterization of a novel thioesterase (PtTE) from *Phaeodactylum tricornutum*," J Basic Microbiol. Dec. 2011;51(6):666-72. doi: 10.1002/jobm.201000520. Epub Jun. 9, 2011, Wiley-VCH Verlag , Weinheim, Germany.
Excerpted file history, U.S. Appl. No. 14/646,895, § 371 Date: May 22, 2015, Applicant's preliminary amendment filed May 22, 2015 at the United States Patent and Trademark Office, Alexandria, VA.
Excerpted file history, U.S. Appl. No. 14/897,049, § 371 Date: Dec. 9, 2015, restriction requirement dated Jan. 23, 2017 and Applicant's preliminary amendment filed Dec. 9, 2015 at the United States Patent and Trademark Office, Alexandria, VA.
GenBank Accession No. EKU23063.1, Thioesterase superfamily member 4 [Nannochloropsis gaditana CCMP526], Radakovits, R. et al., direct submission, GenBank version EKU23063.1, GI:422295764, PLN Nov. 20, 2012, retrieved from the Internet, www.ncbi.nlm.nih.gov/protein/EKU23063.1?report=girevhist>, on Feb. 3, 2014.
GenBank Accession No. EKU23063.1, Thioesterase superfamily member 4 [Nannochloropsis gaditana CCMP526], Radakovits, R. et al., direct submission, GenBank version EKU23063.1, GI:422295764, PLN Nov. 20, 2012, last update Mar. 18, 2015, retrieved from the Internet, www.ncbi.nlm.nih.gov/protein/EKU23063.1?report=girevhist>, on Apr. 23, 2015.
Leggat, W. et al., "Analysis of an EST library from the dinoflagellate (*Symbiodinium* sp.) symbiont of reef-building corals," Journal of Phycology 43(5): 1010-1021, Oct. 2007, Wiley.

Radakovits, R. et al., "Draft genome sequence and genetic transformation of the oleaginous alga *Nannochloropsis gaditana*," Nature Communications (Feb. 21, 2012), vol. 3, Article No. 686, ten pages (1-10), doi:10.1038/ncomms1688; and Corrigendum to correct the Title, Nature Communications vol. 4, Article No. 2356, Sep. 19, 2013; Nature Pub. Group, London, England).
Radakovits, R et al., "Genetic Engineering of Algae for Enhanced Biofuel Production," Eukaryot Cell, Apr. 2010; 9:486-501, American Society for Microbiology, Washington, DC.
Zhang, H. et al., "Proof that Dinoflagellate Spliced Leader (DinoSL) is a Useful Hook for Fishing Dinoflagellate Transcripts from Mixed Microbial Samples: *Symbiodinium kawagutii* as a Case Study," Protist 164:510-527 (Jul. 2013; Epub: Jun. 14, 2013), Elsevier GmbH.
Zhang, X et al., "Efficient free fatty acid production in *Escherichia coli* using plant acyl-ACP thioesterases," Metabolic Engineering 13 (2011) 713-722, Brugge, Belgium.
PCT phase of U.S. Appl. No. 14/646,895—International Search Report (ISR) for PCT/JP2013/084244; I.A. fd: Dec. 20, 2013, dated Feb. 18, 2014, the Japanese Patent Office, Tokyo, Japan.
PCT phase of U.S. Appl. No. 14/646,895—International Preliminary Report on Patentability (IPRP) including the Written Opinion of the International Searching Authority (PCT Rule 44bis) for PCT/JP2013/084244; I.A. fd: Dec. 20, 2013, dated Jun. 30, 2015, by the International Bureau of WIPO, Geneva, Switzerland.
PCT phase of U.S. Appl. No. 14/897,049—International Search Report (ISR) for PCT/JP2014/067137; I.A. fd: Jun. 27, 2014, dated Sep. 2, 2014, from the Japanese Patent Office, Tokyo, Japan.
PCT phase of U.S. Appl. No. 14/897,049—International Preliminary Report on Patentability (IPRP), Chapter I of the Patent Cooperation Treaty, including the Written Opinion for PCT/JP2014/067137; I.A. fd: Jun. 27, 2014, dated Jan. 12, 2016, from the International Bureau of WIPO, Geneva, Switzerland.
Excerpted file history, U.S. Appl. No. 14/646,895, § 371 Date: May 22, 2015, Non-Final Rejection dated Feb. 13, 2017, from the United States Patent and Trademark Office, Alexandria, VA.
Excerpted file history, U.S. Appl. No. 14/897,049, § 371 Date: Dec. 9, 2015, applicant's reply to restriction requirement filed Feb. 24, 2017, at the United States Patent and Trademark Office, Alexandria, VA.
Excerpted file history, U.S. Appl. No. 14/897,049, § 371 Date: Dec. 9, 2015, issue notification (dated Nov. 8, 2017), Notice of Allowance (dated Aug. 15, 2017), examiner initiated interview summary and two appendices (dated Aug. 4, 2017), miscellaneous incoming letter (stmt of common ownership) (Aug. 4, 2017); the United States Patent and Trademark Office, Alexandria, VA.
Excerpted file history, U.S. Appl. No. 14/646,895, § 371 Date: May 22, 2015, issue notification (dated Sep. 12, 2018), Notice of allowance and examiner initiated interview summary (dated Jun. 8, 2018), supplemental amendment (dated Jun. 1, 2018), RCE and amendment (dated Mar. 6, 2018), final rejection (dated Dec. 6, 2017), applicant summary of interview (dated Sep. 28, 2017), applicant initiated interview summary and appendix (dated Sep. 8, 2017), amendment and reply (dated Sep. 7, 2017), Notice regarding non-compliant or non-responsive amendment (dated Aug. 7, 2017); the United States Patent and Trademark Office, Alexandria, VA.
Excerpted file history, U.S. Appl. No. 15/110,635, § 371 Date: Jul. 8, 2016, issue notification (dated Aug. 21, 2028), Notice of allowance (dated May 9, 2018), terminal disclaimer review decision (dated Apr. 5, 2018), amendment and terminal disclaimer (dated Apr. 4, 2018), non-final rejection (dated Jan. 11, 2018), response to election/restriction and preliminary amendment (dated Dec. 11, 2017), requirement for restriction/election (dated Oct. 12, 2017); the United States Patent and Trademark Office, Alexandria, VA.
Excerpted file history, U.S. Appl. No. 15/317,347, § 371 Date: Dec. 8, 2016, final rejection (dated Jun. 6, 2018), amendment and reply (dated Mar. 19, 2018); non-final rejection (dated Dec. 21, 2017); preliminary amendment (dated Dec. 8, 2016); the United States Patent and Trademark Office, Alexandria, VA.

* cited by examiner

```
NoTE.prj    1:MTPLAFTVLGKLGGTLTFACVRRLYHLLRRATLSSHYQV-TRPYGHSNSGCSHSTTLRTSFPVLFAQLAATAAVTAAISLP-SPSL-   87
NgTE.prj    1:MLCCACKSVHATISVAFIGT-RKPH-RL-PALF-PL-FLAPARALSHQEPNPATCGTQNSS-FSILLKTVVAGSFVGA-AFIAGHTAGAS   83
NgrTE..prj  1:MTPLAFTALGEVGGMLAAACVRRKLHHLLRRAASSS--QV-TRPYSHSTANSTHSTTLSNSFPVLFAQLAAAAVMAATSLS-SPSL-   85
                 .   *     .  .  :     ..  ::      .  :  *.       : ..:.*   .:.:.:..::*:****:**  .   :***  ....

NoTE.prj    88:CETAHAGTEERRGERKAMREDG-GKGEATSSATC-NPSLFEHHDRVDTKLHRAYPEFLKFHLIHETLRGKEKIDGYEVKDRRDDSTVAY  175
NgTE.prj    84:CDEVKSPQEVNN------V--GGG-APVTAPYTVTFASNY--HDRVDTKLHRAYPEELQYHLIHETLRGKEKIEGYEVKDRRDDSTVAF  162
NgrTE..prj  86:CETAHTNTEERGGEGEAMREKG-G3GEATSSATC-APSFEHHDRVDTKLHRAYPEFLKFHLIHETLRGKEKIDGYEVYNRRDDSVAY   173
                 *   .            *  .  .:   ::.         ********** :::*************.****  *****:**:.  ..***

NoTE.prj    176:ARLGKLLSCHPDIIHGGSIAALLDNTMGVAFFAAKRGNGTANLIINYKRPITCGTEVKVLAREVEGRKVFLRAEITDAKDEAILYTE  265
NgTE.prj    163:ARLGKLLSGHPDIIHGGSIAALLDNTMGVAFFAANKGNGTANKGNGTANLIINYKRPIICCGTEIKVLARVERFEGRKVLARVEFEGRKVFLRAELRAEITDAKDEAVLYTE  252
NgrTE..prj  174:ARLGKLLSGHPDIIHGGSIAALLDNTMGVAFFAAKRGNGTANLIINYKRPITCGTEVKVLARVEKVEGRKVFLRAEITDAKDEAILYTE  263
                   ***********..  ***************************   **** .  ****   *. *****.. ..**********  .****

NoTE.prj    266:AKSLFITSQSPLLKGPKKIDIS  287
NgTE.prj    253:ATSLFITSQSPLLTGPKKVDIS  274
NgrTE..prj  264:ANSLFITSQSPLLKGPKKIDIS  285
                   * **************.****:.***
```

SEQUENCE LISTING

<160> NUMBER OF SEQ ID NOS: 69

<210> SEQ ID NO 1
<211> LENGTH: 287
<212> TYPE: PRT
<213> ORGANISM: Nannochloropsis oculata

<400> SEQUENCE: 1

```
Met Thr Pro Leu Ala Phe Thr Val Leu Gly Lys Leu Gly Gly Thr Leu
1               5                   10                  15

Thr Phe Ala Cys Val Arg Arg Leu Tyr His Leu Leu Arg Arg Ala
            20                  25                  30

Thr Leu Ser Ser His Tyr Gln Val Thr Arg Pro Tyr Gly His Ser Asn
        35                  40                  45

Ser Gly Cys Ser His Ser Thr Thr Thr Leu Arg Thr Ser Phe Pro Val
    50                  55                  60

Leu Phe Ala Gln Leu Ala Ala Ala Thr Ala Ala Val Val Ala Ala Ile
65                  70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
        115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
        195                 200                 205

Ala Lys Arg Gly Asn Gly Phe Thr Ala Asn Leu Thr Ile Asn Tyr Lys
    210                 215                 220

Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
                245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
        275                 280                 285
```

<210> SEQ ID NO 2
<211> LENGTH: 864
<212> TYPE: DNA
<213> ORGANISM: Nannochloropsis oculata

<400> SEQUENCE: 2

```
atgacgcctt tggccttcac ggtgctcggc aagcttggtg gcacgttgac ttttgcttgt    60
gtacgacgga ggctttatca cttgttacgg cgggcaactt tgtcctccca ttatcaggtc   120
actcggcctt acggtcacag caattccggc tgttcacata gcactaccac acttagaacc   180
agcttcccag tcctctttgc gcaattggca gcagccactg ctgccgtcgt cgctgccatt   240
```

```
tccctgccgt cgcctagtct atgcgagacg gcccacgccg ggactgagga gagacgaggt    300
gagaggaagg caatgaggga ggatggtgga aaaggcgagg ccacctcgtc tgctacatgc    360
aatccatcct tattcgaaca tcatgatcgc gtcgacacca agctgcatcg ggcctatcct    420
gaattcctga agttccacct tatccacgag acgctccgag caaagagaa aattgatggc     480 tacgaagttt acaaagacag gcgggatgat tcaattgtgg cgtatgctcg ccttggcaaa    540
ctgctgagcg acaccccga cataatccac ggagggtcca ttgcggcttt gctgacaat     600 accatgggag ttgccttttt cgccgccaag cgtggcaatg gttttacagc aaatctcacc    660
atcaactaca agcgacccat cacgtgtggc accgaagtca agttttagc tcgagtagag     720 aaggtggaag gcgcaaggt cttcttgcgg gccgagattc gagacgctaa ggatgaggct     780
atcctctaca ctgaagccaa atccctcttc atcacgtctc aaagtccttt attgaagggc    840
ccaaagaaaa ttgatattag ctag                                           864
```

<210> SEQ ID NO 3
<211> LENGTH: 274
<212> TYPE: PRT
<213> ORGANISM: Nannochloropsis gaditana

<400> SEQUENCE: 3

```
Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

Phe Leu Gln Tyr His Leu Ile His Glu Thr Leu Arg Gly Lys Glu Lys
    130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205

Asn Tyr Lys Arg Pro Ile Ile Cys Gly Thr Glu Ile Lys Val Leu Ala
    210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255
```

Phe Ile Thr Ser Gln Ser Pro Leu Leu Thr Gly Pro Lys Lys Val Asp
            260                 265                 270

Ile Ser

<210> SEQ ID NO 4
<211> LENGTH: 825
<212> TYPE: DNA
<213> ORGANISM: Nannochloropsis gaditana

<400> SEQUENCE: 4
atgctatgtt gcgcctgtaa atcagtgcat gcgactatta gtgtcgcctt tattggtact      60
cggaagccac atcgtttgcc tgcattgttt ccattgttcc ttgccccggc ccgagcactc     120
agccatcagg agccgaaccc tgcaacgtgc gggacgcaaa actcatcctt ctcgatcttg     180
ttgaaaacgg tagtagcagg atcattcgtc ggtgcggcat tcatcgctgg catacagca      240
ggggctagct gtgatgaagt aaagtctccg caggaggtga acaatgtagg aggcggcgcc     300
ccagtgactg cccctacac ggtcactttt gcgtccaatt atcatgatcg agtggacaca      360
aaacttcata gagcttatcc tgagttttta cagtaccatc ttattcatga aacgcttcga     420
ggcaaggaaa agatagaggg ctacgaggtg tacaaagata ggcgtgacga ttctatcgta     480
gcatttgctc gcctcgggaa gcttctcagc gggcatccgg atataatcca tggaggctct     540
atagccgcct tactcgacaa cactatgggc gtggcattct tcgctgccaa taaaggtaat     600
ggcttcactg ccaacctcac aatcaattac aagaggccga tcatttgtgg caccgagatc     660
aaggtcttgg cccgagtgga gcggtttgaa ggacgcaagg ttttcctacg agcagagatt     720
cgagatgcta aggacgaggc agtgttgtac acggaagcca catccctctt cataacttca     780
caaagtcctc tgcttacggg accgaagaag gtggacatca gttag                    825

<210> SEQ ID NO 5
<211> LENGTH: 38
<212> TYPE: DNA
<213> ORGANISM: Artificial Sequence
<220> FEATURE:
<223> OTHER INFORMATION: PCR primer 1 for NoTE_262

<400> SEQUENCE: 5
gcggccgctc tagagtgcga gacggcccac gccgggac                              38

<210> SEQ ID NO 6
<211> LENGTH: 39
<212> TYPE: DNA
<213> ORGANISM: Artificial Sequence
<220> FEATURE:
<223> OTHER INFORMATION: PCR primer 2 for NoTE_262

<400> SEQUENCE: 6
acaaaatatt aacgcctagc taatatcaat tttctttgg                             39

<210> SEQ ID NO 7
<211> LENGTH: 20
<212> TYPE: DNA
<213> ORGANISM: Artificial Sequence
<220> FEATURE:
<223> OTHER INFORMATION: PCR primer 1 for pBluescriptII

<400> SEQUENCE: 7
ctctagagcg gccgccaccg                                                  20

<210> SEQ ID NO 8

-continued

```
<211> LENGTH: 24
<212> TYPE: DNA
<213> ORGANISM: Artificial Sequence
<220> FEATURE:
<223> OTHER INFORMATION: PCR primer 2 for pBluescriptII

<400> SEQUENCE: 8
gcgttaatat tttgttaaaa ttcg                                           24

<210> SEQ ID NO 9
<211> LENGTH: 36
<212> TYPE: DNA
<213> ORGANISM: Artificial Sequence
<220> FEATURE:
<223> OTHER INFORMATION: PCR primer 3 for NoTE_262

<400> SEQUENCE: 9
ctggacaata ccatgtgggt tgccttttc gccgcc                              36

<210> SEQ ID NO 10
<211> LENGTH: 39
<212> TYPE: DNA
<213> ORGANISM: Artificial Sequence
<220> FEATURE:
<223> OTHER INFORMATION: PCR primer 4 for NoTE_262

<400> SEQUENCE: 10
ctggacaata ccatgggatg ggccttttc gccgccaag                           39

<210> SEQ ID NO 11
<211> LENGTH: 35
<212> TYPE: DNA
<213> ORGANISM: Artificial Sequence
<220> FEATURE:
<223> OTHER INFORMATION: PCR primer 5 for NoTE_262

<400> SEQUENCE: 11
ctggacaata ccatgtggtg ggccttttc gccgc                               35

<210> SEQ ID NO 12
<211> LENGTH: 35
<212> TYPE: DNA
<213> ORGANISM: Artificial Sequence
<220> FEATURE:
<223> OTHER INFORMATION: PCR primer 6 for NoTE_262

<400> SEQUENCE: 12
ctggacaata ccatgtggtt tgccttttc gccgc                               35

<210> SEQ ID NO 13
<211> LENGTH: 20
<212> TYPE: DNA
<213> ORGANISM: Artificial Sequence
<220> FEATURE:
<223> OTHER INFORMATION: PCR primer 7 for NoTE_262

<400> SEQUENCE: 13
catggtattg tccagcaaag                                               20

<210> SEQ ID NO 14
<211> LENGTH: 35
<212> TYPE: DNA
<213> ORGANISM: Artificial Sequence
<220> FEATURE:
<223> OTHER INFORMATION: PCR primer 8 for NoTE_262

<400> SEQUENCE: 14
```
gcctatcctg aattccctaa gttccacctt atcca                                     35

<210> SEQ ID NO 15
<211> LENGTH: 29
<212> TYPE: DNA
<213> ORGANISM: Artificial Sequence
<220> FEATURE:
<223> OTHER INFORMATION: PCR primer 9 for NoTE_262

<400> SEQUENCE: 15
gaattcagga taggcccgat gcagcttgg                                            29

<210> SEQ ID NO 16
<211> LENGTH: 35
<212> TYPE: DNA
<213> ORGANISM: Artificial Sequence
<220> FEATURE:
<223> OTHER INFORMATION: PCR primer 10 for NoTE_262

<400> SEQUENCE: 16
ggcaaagaga aaattgatgc ttacgaagtt tacaa                                     35

<210> SEQ ID NO 17
<211> LENGTH: 28
<212> TYPE: DNA
<213> ORGANISM: Artificial Sequence
<220> FEATURE:
<223> OTHER INFORMATION: PCR primer 11 for NoTE_262

<400> SEQUENCE: 17
aattttctct ttgcctcgga gcgtctcg                                             28

<210> SEQ ID NO 18
<211> LENGTH: 35
<212> TYPE: DNA
<213> ORGANISM: Artificial Sequence
<220> FEATURE:
<223> OTHER INFORMATION: PCR primer 12 for NoTE_262

<400> SEQUENCE: 18
gccaagcgtg gcaatccatt tacagcaaat ctcac                                     35

<210> SEQ ID NO 19
<211> LENGTH: 23
<212> TYPE: DNA
<213> ORGANISM: Artificial Sequence
<220> FEATURE:
<223> OTHER INFORMATION: PCR primer 13 for NoTE_262

<400> SEQUENCE: 19
cttggcggcg aaaaaggcaa ctc                                                  23

<210> SEQ ID NO 20
<211> LENGTH: 35
<212> TYPE: DNA
<213> ORGANISM: Artificial Sequence
<220> FEATURE:
<223> OTHER INFORMATION: PCR primer 14 for NoTE_262

<400> SEQUENCE: 20
gccgccaagc gtggctacgg ttttacagca aatct                                     35

<210> SEQ ID NO 21
<211> LENGTH: 24
<212> TYPE: DNA

<213> ORGANISM: Artificial Sequence
<220> FEATURE:
<223> OTHER INFORMATION: PCR primer 15 for NoTE_262

<400> SEQUENCE: 21
gccacgcttg gcggcgaaaa aggc                                          24

<210> SEQ ID NO 22
<211> LENGTH: 37
<212> TYPE: DNA
<213> ORGANISM: Artificial Sequence
<220> FEATURE:
<223> OTHER INFORMATION: PCR primer 1 for NoTE_382

<400> SEQUENCE: 22
gcggccgctc tagagcatga tcgcgtcgac accaagc                            37

<210> SEQ ID NO 23
<211> LENGTH: 36
<212> TYPE: DNA
<213> ORGANISM: Artificial Sequence
<220> FEATURE:
<223> OTHER INFORMATION: PCR primer 1 for NgTE

<400> SEQUENCE: 23
gcggccgctc tagaggatga agtaaagtct ccgcag                             36

<210> SEQ ID NO 24
<211> LENGTH: 37
<212> TYPE: DNA
<213> ORGANISM: Artificial Sequence
<220> FEATURE:
<223> OTHER INFORMATION: PCR primer 2 for NgTE

<400> SEQUENCE: 24
acaaaatatt aacgcctaac tgatgtccac cttcttc                            37

<210> SEQ ID NO 25
<211> LENGTH: 35
<212> TYPE: DNA
<213> ORGANISM: Artificial Sequence
<220> FEATURE:
<223> OTHER INFORMATION: PCR primer 3 for NgTE

<400> SEQUENCE: 25
ctcgacaaca ctatgtggtg ggcattcttc gctgc                              35

<210> SEQ ID NO 26
<211> LENGTH: 31
<212> TYPE: DNA
<213> ORGANISM: Artificial Sequence
<220> FEATURE:
<223> OTHER INFORMATION: PCR primer 4 for NgTE

<400> SEQUENCE: 26
catagtgttg tcgagtaagg cggctataga g                                  31

<210> SEQ ID NO 27
<211> LENGTH: 38
<212> TYPE: DNA
<213> ORGANISM: Artificial Sequence
<220> FEATURE:
<223> OTHER INFORMATION: PCR primer 1 for NoTE_262_Nanno

<400> SEQUENCE: 27
cgcggtgttg cgcgctgcga gacggcccac gccgggac                           38

<210> SEQ ID NO 28
<211> LENGTH: 39
<212> TYPE: DNA
<213> ORGANISM: Artificial Sequence
<220> FEATURE:
<223> OTHER INFORMATION: PCR primer 2 for NoTE_262_Nanno

<400> SEQUENCE: 28
ctcttccaca gaagcctagc taatatcaat tttctttgg                                    39

<210> SEQ ID NO 29
<211> LENGTH: 802
<212> TYPE: DNA
<213> ORGANISM: Artificial Sequence
<220> FEATURE:
<223> OTHER INFORMATION: VCP1 promoter

<400> SEQUENCE: 29
ggcggtcttt tgtcctttcc tctatagccc gcccgtctag agggcacacg cgatgatctt            60
tatatctctt catgtgtctt tgttttaact aggatactgc cgggtgaatg cccatcggac           120
aagaggccaa actctatcta cacccttttg acttctgttg tggtcgtagt gtgtgcttgc           180
atgccctgaa agtccaggca tcccacttgt gctctaaccc cattcaaaac agcagaagtg           240
cttaattaag atatagattc atgatctcct gtcccctcct tcttaccttt tcacaaacct           300
cacacagaag tctccactct tcgcctctaa aacctctttt taaattatgg taagttcgtg           360
cggcagtggg ttttcggatc tatatttgtc aagatccagt tcaaggtcag ggatgtagat           420
taagtacaga aggagaagca caagcgcgcc agttcgcccc tcacggcctg gagcagggca           480
tttaatccct ctatcttacc agaaccatac tatacaacca atcctgttgg catcgctctg           540
tctatttgtc gtgcgtgcat gtgtccatgg tgtggtgggg ggcaggggtt ttcggggttg           600
cggttgaagg caccttatca gaaagatgcc ctcagagata gaggtagccc cctcccccg           660 atcttcgacc agtcctgtca ggcgaacact ttcacccgtc gttcacctcg ttacacacaa           720
ggagtagacc tctgaagttc taattgtcat aaatgcccct ccccctccc tctttccctt           780 catcctcccc tccgagcaga tt                                                    802

<210> SEQ ID NO 30
<211> LENGTH: 99
<212> TYPE: DNA
<213> ORGANISM: Artificial Sequence
<220> FEATURE:
<223> OTHER INFORMATION: VCP1 chloroplast transit signal

<400> SEQUENCE: 30
atgaagaccg ccgctctcct cactgtctcc accctcatgg gcgcccaggc ctttatggcc            60
cccgccccca gttctcccg cacccgcggt gttgcgcgc                                    99

<210> SEQ ID NO 31
<211> LENGTH: 643
<212> TYPE: DNA
<213> ORGANISM: Artificial Sequence
<220> FEATURE:
<223> OTHER INFORMATION: VCP1 terminator

<400> SEQUENCE: 31
gcttctgtgg aagagccagt ggtagtagca gtagcagcag cagtagcagc cgcagcactc            60
agtgttggcg cgagagattg tccatccctt cttaacctac cggaagagaa ataaggcctt           120

```
tctcccgtag ctgtcttcgt tgtttgtgc tgattgcttg atatgagagt gttgaattcc    180
tgcatcatgt ttttctctgt agtcctttcc taccccgtc attttctttt ctccctggtt    240
cttcttttgt caccttatt ttacataaaa ttttctttgt ttatagtgag aggaaggtag    300 agagggaaa acaagaacaa cgaacgcaag cgtgtgaaag gagggcgagt agaagagaaa    360
cagatctgtt gagcattgag agtggagccg ggggaaaggc ttgtgtgttg tctttgaaaa    420
agttgtttaa atcacgaatc cgttagttct catgtgtacc tctttcacta catgtgatgg    480
agaaaacaaa agtgtgagga ttaattgaag aaaaagaaga gttcgacacg tcaaaccgcc    540
caaaagacgt cacaaagaga acttgattct ctttgccgtg ttgatcctgt cttttccccc    600
agcttttctt gccacccgtg gcacacgaga tggacaagat cag                     643
```

<210> SEQ ID NO 32
<211> LENGTH: 37
<212> TYPE: DNA
<213> ORGANISM: Artificial Sequence
<220> FEATURE:
<223> OTHER INFORMATION: PCR primer 1 for VCP1 promoter

<400> SEQUENCE: 32

```
cgagctcggt acccgggcgg tcttttgtcc tttcctc                             37
```

<210> SEQ ID NO 33
<211> LENGTH: 22
<212> TYPE: DNA
<213> ORGANISM: Artificial Sequence
<220> FEATURE:
<223> OTHER INFORMATION: PCR primer 2 for VCP1 promoter

<400> SEQUENCE: 33

```
aatctgctcg gaggggagga tc                                             22
```

<210> SEQ ID NO 34
<211> LENGTH: 36
<212> TYPE: DNA
<213> ORGANISM: Artificial Sequence
<220> FEATURE:
<223> OTHER INFORMATION: PCR primer 1 for VCP1 chloroplast transit
      signal

<400> SEQUENCE: 34

```
ccctccgagc agattatgaa gaccgccgct ctcctc                              36
```

<210> SEQ ID NO 35
<211> LENGTH: 28
<212> TYPE: DNA
<213> ORGANISM: Artificial Sequence
<220> FEATURE:
<223> OTHER INFORMATION: PCR primer 2 for VCP1 chloroplast transit
      signal

<400> SEQUENCE: 35

```
gcgcgcaaca ccgcgggtgc gggagaac                                       28
```

<210> SEQ ID NO 36
<211> LENGTH: 21
<212> TYPE: DNA
<213> ORGANISM: Artificial Sequence
<220> FEATURE:
<223> OTHER INFORMATION: PCR primer 1 for VCP1 terminator

<400> SEQUENCE: 36

```
gcttctgtgg aagagccagt g                                              21
```

<210> SEQ ID NO 37
<211> LENGTH: 35
<212> TYPE: DNA
<213> ORGANISM: Artificial Sequence
<220> FEATURE:
<223> OTHER INFORMATION: PCR primer 2 for VCP1 terminator

<400> SEQUENCE: 37
actctagagg atcccctgat cttgtccatc tcgtg                         35

<210> SEQ ID NO 38
<211> LENGTH: 20
<212> TYPE: DNA
<213> ORGANISM: Artificial Sequence
<220> FEATURE:
<223> OTHER INFORMATION: PCR primer 1 for plasmid pUC19

<400> SEQUENCE: 38
gggatcctct agagtcgacc                                          20

<210> SEQ ID NO 39
<211> LENGTH: 20
<212> TYPE: DNA
<213> ORGANISM: Artificial Sequence
<220> FEATURE:
<223> OTHER INFORMATION: PCR primer 2 for plasmid pUC19

<400> SEQUENCE: 39
cgggtaccga gctcgaattc                                          20

<210> SEQ ID NO 40
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 40
atggccaagc tgaccagcgc cgttccggtg ctcaccgcgc gcgacgtcgc cggagcggtc    60
gagttctgga ccgaccggct cgggttctcc cggacttcg tggaggacga cttcgccggt   120
gtggtccggg acgacgtgac cctgttcatc agcgcggtcc aggaccaggt ggtgccggac   180
aacaccctgg cctgggtgtg ggtgcgcggc ctggacgagc tgtacgccga gtggtcggag   240
gtcgtgtcca cgaacttccg ggacgcctcc gggccggcca tgaccgagat cggcgagcag   300
ccgtgggggc gggagttcgc cctgcgcgac ccggccggca ctgcgtgca cttcgtggcc    360 gaggagcagg actaa                                                   375

<210> SEQ ID NO 41
<211> LENGTH: 500
<212> TYPE: DNA
<213> ORGANISM: Artificial Sequence
<220> FEATURE:
<223> OTHER INFORMATION: Tubulin promoter

<400> SEQUENCE: 41
actgcgcatg gattgaccga cggccggttg ccaacttttg gggtcggccc ccctttttcta    60 gcccttgccc gtccagcaat taaaaattat caacggcata ccggcactgg aagcttcggg   120
tttacaattt tggcttgcct tcctaatact gtaccgcgga gaacgtatga tattacagaa   180
aaatgccttg cacagttagc gcaaagggaa aacgtttctc cgccattgta cttttggaa    240

```
gagggaaagc gattgtaaaa tatggctctc cgctacgaga gtttgggctg ttgatacatg    300
tgaaaataag tgtggacgac tttgaatgac ttgatcaggc tgtttgcaca tataaccagc    360
gcgcatgcac ttctgacatg tcaatgacga aatttcacac ttcaccaata aattgtatcc    420
ttacgttttg tctttctcac acgcacatat atgatcatag ataaaagcca atatcaagaa    480
gctgtctttt ttgtgaagca                                                500
```

```
<210> SEQ ID NO 42
<211> LENGTH: 37
<212> TYPE: DNA
<213> ORGANISM: Artificial Sequence
<220> FEATURE:
<223> OTHER INFORMATION: PCR primer 1 for zeocin resistance gene

<400> SEQUENCE: 42
cttttttgtg aagcaatggc caagttgacc agtgccg                              37

<210> SEQ ID NO 43
<211> LENGTH: 37
<212> TYPE: DNA
<213> ORGANISM: Artificial Sequence
<220> FEATURE:
<223> OTHER INFORMATION: PCR primer 2 for zeocin resistance gene

<400> SEQUENCE: 43
ctcttccaca gaagcttagt cctgctcctc ggccacg                              37

<210> SEQ ID NO 44
<211> LENGTH: 35
<212> TYPE: DNA
<213> ORGANISM: Artificial Sequence
<220> FEATURE:
<223> OTHER INFORMATION: PCR primer 1 for tubulin promoter

<400> SEQUENCE: 44
cgagctcggt acccgactgc gcatggattg accga                                35

<210> SEQ ID NO 45
<211> LENGTH: 28
<212> TYPE: DNA
<213> ORGANISM: Artificial Sequence
<220> FEATURE:
<223> OTHER INFORMATION: PCR primer 2 for tubulin promoter

<400> SEQUENCE: 45
tgcttcacaa aaagacagc ttcttgat                                         28

<210> SEQ ID NO 46
<211> LENGTH: 22
<212> TYPE: DNA
<213> ORGANISM: Artificial Sequence
<220> FEATURE:
<223> OTHER INFORMATION: PCR primer 1 for DNA fragment containing NoTE

<400> SEQUENCE: 46
ggcggtcttt tgtcctttcc tc                                              22

<210> SEQ ID NO 47
<211> LENGTH: 20
<212> TYPE: DNA
<213> ORGANISM: Artificial Sequence
<220> FEATURE:
<223> OTHER INFORMATION: PCR primer 2 for DNA fragment containing NoTE

<400> SEQUENCE: 47
```

-continued

```
ctgatcttgt ccatctcgtg                                                   20

<210> SEQ ID NO 48
<211> LENGTH: 20
<212> TYPE: DNA
<213> ORGANISM: Artificial Sequence
<220> FEATURE:
<223> OTHER INFORMATION: PCR primer 1 for DNA fragment containing zeocin
      resistance gene

<400> SEQUENCE: 48
actgcgcatg gattgaccga                                                   20

<210> SEQ ID NO 49
<211> LENGTH: 285
<212> TYPE: PRT
<213> ORGANISM: Nannochloropsis granulata

<400> SEQUENCE: 49

Met Thr Pro Leu Ala Phe Thr Ala Leu Gly Glu Val Gly Gly Met Leu
1               5                  10                  15

Ala Ala Ala Cys Val Arg Arg Lys Leu His His Leu Leu Arg Arg Ala
            20                  25                  30

Ala Ser Ser Ser Gln Val Thr Arg Pro Tyr Ser His Ser Thr Ala Asn
        35                  40                  45

Ser Thr His Ser Thr Thr Thr Leu Ser Asn Ser Phe Pro Val Leu Phe
    50                  55                  60

Ala Gln Leu Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285
```

<210> SEQ ID NO 50
<211> LENGTH: 858
<212> TYPE: DNA
<213> ORGANISM: Nannochloropsis granulata

<400> SEQUENCE: 50

```
atgacgcctt tggccttcac ggcgctcggc gaggtcggtg gcatgttggc tgctgcctgt      60
gtacgacgga agcttcatca cttgttgcgg cgggcagctt cgtcctccca ggtcactcga     120
ccttacagtc acagcaccgc caacagcaca catagcacca ccacacttag caacagcttt     180
ccagtcctct ttgcgcaact cgcagcagcc gctgctgccg tcatggctgc cacttccctg     240
tcgtcgccca gtctatgtga cacggcccac accaatactg aggagagagg aggcgaaggg     300
gaggcaatga gggagaaggg tggggaaggc gaggccactt cgtctgctac atgcgctcca     360
tctttcttcg agcatcatga tcgcgtcgac acgaagctgc atcgggccta tcccgagttt     420
ctgaagttcc acctcatcca cgagacgctc cgagggaaag agaaaattga tggctacgaa     480
gtatacaaaa acaggcggga cgattcagtt gtggcgtatg ctcgcctggg caaactgctg     540
agcggacacc ctgacataat tcacggaggg tccatcgctg ctttgctgga caacaccatg     600
ggagttgcct ttttcgccgc caagcgcggc aatggtttca cagcaaatct caccatcaac     660
tacaagcgac ccatcacgtg tggcaccgag gtcaaagttc tggctcgagt agagaaggtg     720
gaggggcgca aggtcttttt gcgggctgag atcagggacg ccaaggatga ggctatcctt     780
tacactgaag ccaactccct cttcatcacg tcgcaaagcc ctctattgaa gggcccaaag     840
aaaattgaca ttagctag                                                   858
```

<210> SEQ ID NO 51
<211> LENGTH: 23
<212> TYPE: DNA
<213> ORGANISM: Artificial Sequence
<220> FEATURE:
<223> OTHER INFORMATION: PCR primer 16 for NoTE_262

<400> SEQUENCE: 51

```
gaacttcagg aattcaggat agg                                              23
```

<210> SEQ ID NO 52
<211> LENGTH: 35
<212> TYPE: DNA
<213> ORGANISM: Artificial Sequence
<220> FEATURE:
<223> OTHER INFORMATION: PCR primer 17 for NoTE_262

<400> SEQUENCE: 52

```
gaattcctga agttcaacct tatccacgag acgct                                 35
```

<210> SEQ ID NO 53
<211> LENGTH: 35
<212> TYPE: DNA
<213> ORGANISM: Artificial Sequence
<220> FEATURE:
<223> OTHER INFORMATION: PCR primer 18 for NoTE_262

<400> SEQUENCE: 53

```
gaattcctga agttctcact tatccacgag acgct                                 35
```

<210> SEQ ID NO 54
<211> LENGTH: 25
<212> TYPE: DNA
<213> ORGANISM: Artificial Sequence
<220> FEATURE:

<223> OTHER INFORMATION: PCR primer 19 for NoTE_262

<400> SEQUENCE: 54
ggtattgtcc agcaaagccg caatg                                   25

<210> SEQ ID NO 55
<211> LENGTH: 35
<212> TYPE: DNA
<213> ORGANISM: Artificial Sequence
<220> FEATURE:
<223> OTHER INFORMATION: PCR primer 20 for NoTE_262

<400> SEQUENCE: 55
ttgctggaca ataccttcgg atgggccttt ttcgc                         35

<210> SEQ ID NO 56
<211> LENGTH: 35
<212> TYPE: DNA
<213> ORGANISM: Artificial Sequence
<220> FEATURE:
<223> OTHER INFORMATION: PCR primer 21 for NoTE_262

<400> SEQUENCE: 56
ttgctggaca atacccatgg atgggccttt ttcgc                         35

<210> SEQ ID NO 57
<211> LENGTH: 35
<212> TYPE: DNA
<213> ORGANISM: Artificial Sequence
<220> FEATURE:
<223> OTHER INFORMATION: PCR primer 22 for NoTE_262

<400> SEQUENCE: 57
ttgctggaca ataccctagg atgggccttt ttcgc                         35

<210> SEQ ID NO 58
<211> LENGTH: 35
<212> TYPE: DNA
<213> ORGANISM: Artificial Sequence
<220> FEATURE:
<223> OTHER INFORMATION: PCR primer 23 for NoTE_262

<400> SEQUENCE: 58
ttgctggaca atacccaagg atgggccttt ttcgc                         35

<210> SEQ ID NO 59
<211> LENGTH: 35
<212> TYPE: DNA
<213> ORGANISM: Artificial Sequence
<220> FEATURE:
<223> OTHER INFORMATION: PCR primer 24 for NoTE_262

<400> SEQUENCE: 59
ttgctggaca ataccgtagg atgggccttt ttcgc                         35

<210> SEQ ID NO 60
<211> LENGTH: 23
<212> TYPE: DNA
<213> ORGANISM: Artificial Sequence
<220> FEATURE:
<223> OTHER INFORMATION: PCR primer 25 for NoTE_262

<400> SEQUENCE: 60
gcccttcaat aaaggacttt gag                                     23

<210> SEQ ID NO 61
<211> LENGTH: 35
<212> TYPE: DNA
<213> ORGANISM: Artificial Sequence
<220> FEATURE:
<223> OTHER INFORMATION: PCR primer 26 for NoTE_262

<400> SEQUENCE: 61
cctttattga agggccagaa gaaaattgat attag                          35

<210> SEQ ID NO 62
<211> LENGTH: 28
<212> TYPE: DNA
<213> ORGANISM: Artificial Sequence
<220> FEATURE:
<223> OTHER INFORMATION: PCR primer 3 for VCP1 promoter

<400> SEQUENCE: 62
ggcaagaaaa gctgggggaa aagacagg                                  28

<210> SEQ ID NO 63
<211> LENGTH: 35
<212> TYPE: DNA
<213> ORGANISM: Artificial Sequence
<220> FEATURE:
<223> OTHER INFORMATION: PCR primer 3 for plasmid pUC19

<400> SEQUENCE: 63
ccagcttttc ttgccactgc gcatggattg accga                          35

<210> SEQ ID NO 64
<211> LENGTH: 35
<212> TYPE: DNA
<213> ORGANISM: Artificial Sequence
<220> FEATURE:
<223> OTHER INFORMATION: PCR primer for NoTE_1

<400> SEQUENCE: 64
gcggccgctc tagagatgac gcctttggcc ttcac                          35

<210> SEQ ID NO 65
<211> LENGTH: 36
<212> TYPE: DNA
<213> ORGANISM: Artificial Sequence
<220> FEATURE:
<223> OTHER INFORMATION: PCR primer for NoTE_172

<400> SEQUENCE: 65
gcggccgctc tagagcttag aaccagcttc ccagtc                         36

<210> SEQ ID NO 66
<211> LENGTH: 36
<212> TYPE: DNA
<213> ORGANISM: Artificial Sequence
<220> FEATURE:
<223> OTHER INFORMATION: PCR primer for NoTE_232

<400> SEQUENCE: 66
gcggccgctc tagaggctgc catttccctg ccgtcg                         36

<210> SEQ ID NO 67
<211> LENGTH: 35
<212> TYPE: DNA
<213> ORGANISM: Artificial Sequence
<220> FEATURE:
<223> OTHER INFORMATION: PCR primer for NoTE_292

```
<400> SEQUENCE: 67
gcggccgctc tagagagacg aggtgagagg aaggc                              35

<210> SEQ ID NO 68
<211> LENGTH: 36
<212> TYPE: DNA
<213> ORGANISM: Artificial Sequence
<220> FEATURE:
<223> OTHER INFORMATION: PCR primer for NoTE_322

<400> SEQUENCE: 68
gcggccgctc tagaggatgg tggaaaaggc gaggcc                             36

<210> SEQ ID NO 69
<211> LENGTH: 39
<212> TYPE: DNA
<213> ORGANISM: Artificial Sequence
<220> FEATURE:
<223> OTHER INFORMATION: PCR primer for NoTE_352

<400> SEQUENCE: 69
gcggccgctc tagaggctac atgcaatcca tccttattc                          39
```

US 10,550,412 B2

METHOD OF PRODUCING LIPID

TECHNICAL FIELD

The present invention relates to a method of producing a lipid. Further, the present invention also relates to an acyl-ACP thioesterase variant, a gene encoding the same, and a transformant obtained by introducing the gene, for use in this method.

BACKGROUND ART

Fatty acids are one of the principal components of lipids. In vivo, fatty acids are bonded to glycerin via an ester bond to form lipids such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkylbenzenesulfonic acid salts and the like are utilized as anionic surfactants. Further, polyoxyalkylene alkyl ethers, alkyl polyglycosides and the like are utilized as nonionic surfactants. These surfactants are used for detergents or disinfectants. Other higher alcohol derivatives, such as alkylamine salts and mono- or dialkyl-quaternary amine salts are commonly used for fiber treatment agents, hair conditioning agents or disinfectants. Moreover, benzalkonium type quaternary ammonium salts are commonly used for disinfectants or antiseptics. Furthermore, higher alcohols having approximately 18 carbon atoms are also useful as a growth promoter for a plant.

Fatty acids and lipids are widely used for various applications shown above, and therefore, it has been attempted to enhance the productivity of fatty acids or lipids in vivo by using plants and the like. Furthermore, the applications and usefulness of fatty acids depend on the number of carbon atoms. Therefore, controlling of the number of carbon atoms of the fatty acids, namely, a chain length thereof has also been attempted. For example, a method of accumulating fatty acids having 12 carbon atoms by introducing an acyl-ACP (acyl carrier protein) thioesterase derived from *Umbellularia californica* (California bay) (Patent Literature 1, and Non-Patent Literature 1) has been proposed.

Recently, algae attract attention due to its usefulness in biofuel production. The algae can produce lipids that can be used as the biodiesel fuels through photosynthesis, and do not compete with foods. Therefore, the algae attract attention as next-generation biomass resources. Moreover, the algae are also reported to the effect that the algae have higher lipid productivity and accumulation ability in comparison with plants.

Research has started on a lipid synthesis mechanism of the algae and lipid production technologies utilizing the mechanism, but unclear parts remain in many respects. For example, almost no report has been made so far on the above-mentioned acyl-ACP thioesterase derived from algae, either, and only limited examples of reports are made on Class Diatomea or the like (for example, Non-Patent Literature 2).

CITATION LIST

Patent Literatures

Patent Literature 1: WO 92/20236

Non-Patent Literatures

Non-Patent Literature 1: Voelker T A, et al., Science, 1992, vol. 257(5066), p. 72-74
Non-Patent Literature 2: Yangmin Gong, et al., Journal of Basic Microbiology, 2011, vol. 51, p. 666-672

SUMMARY OF INVENTION

The present invention relates to a method of producing a lipid, containing the steps of:
introducing a gene encoding any one of the following proteins (A) to (C) into a host, and thereby obtaining a transformant, and
culturing the transformant, to produce a lipid:
(A) A protein consisting of an amino acid sequence of the 128th to 287th positions set forth in SEQ ID NO: 1 in which at least one of the glycine of the 203rd position and the valine of the 204th position set forth in SEQ ID NO: 1 is substituted with tryptophan;
(B) A protein consisting of an amino acid sequence having 85% or more identity with the amino acid sequence of the 128th to 287th positions set forth in SEQ ID NO: 1, in which at least one of the amino acids corresponding to the 203rd position and the 204th position set forth in SEQ ID NO: 1 is substituted with tryptophan, and having acyl-ACP thioesterase activity; and
(C) A protein containing the amino acid sequence of the protein (A) or (B), and having acyl-ACP thioesterase activity.

The present invention relates to the proteins (A) to (C).
Further, the present invention relates to a gene encoding any one of the proteins (A) to (C).
Furthermore, the present invention relates to a transformant which is obtained by introducing the gene into a host.

BRIEF DESCRIPTION OF DRAWINGS

FIG. 1 is a FIGURE to compare the amino acid sequence of the acyl-ACP thioesterase derived from *Nannochloropsis oclata* (hereinafter, also referred to as "NoTE") (SEQ ID NO: 1), the amino acid sequence of the acyl-ACP thioesterase derived from *Nannochloropsis gaditana* (hereinafter, also referred to as "NgTE") (SEQ ID NO: 3), and the amino acid sequence of the acyl-ACP thioesterase derived from *Nannochloropsis granulata* (hereinafter, also referred to as "NgrTE") (SEQ ID NO: 49).

MODE FOR CARRYING OUT THE INVENTION

The present invention provides an acyl-ACP thioesterase variant, in which the amino acid sequence of the wild type acyl-ACP thioesterase derived from an alga belonging to the genus *Nannochloropsis* is modified; and a method of producing a lipid using the same. Further, the present invention provides a gene encoding the acyl-ACP thioesterase variant. Furthermore, the present invention provides a transformant produced by Introducing the gene, in which a fatty acid composition in a lipid to be produced is changed.

The present inventors conducted research on an acyl-ACP thioesterase derived from algae belonging to the genus

*Nannochloropsis*, in which a wild type acyl-ACP thioesterase derived from *Nannochloropsis oculata* is obtained, and mutation is introduced into this amino acid sequence to obtain a plurality of acyl-ACP thioesterase variants. Further, as a result of conducting transformation by using them, the present inventors found that, in several transformants, the ratio of the content of fatty acids having a specific number of carbon atoms to total fatty acid components in the lipid is significantly improved in comparison with a transformant having the introduced wild type acyl-ACP thioesterase. The present invention was completed based on this finding.

The transformant of the present invention is excellent in ability to produce the fatty acids having the specific number of carbon atoms in comparison with the transformant having the introduced wild type acyl-ACP thioesterase derived from algae belonging to the genus *Nannochloropsis*. A method of producing a lipid using the transformant according to the present invention is particularly excellent in productivity of the fatty acids having the specific number of carbon atoms and the lipid containing these fatty acids as components. The acyl-ACP thioesterase variant, the gene encoding this acyl-ACP thioesterase variant, the transformant and the method of producing a lipid of the present invention can be suitably used for the industrial production of fatty acids having the specific number of carbon atoms and lipids.

In the present specification, the term "lipid(s)" covers simple lipids, complex lipids and derived lipids. Specifically, "lipid(s)" covers fatty acids, aliphatic alcohols, hydrocarbons (such as alkanes), neutral lipids (such as triacylglycerol), wax, ceramides, phospholipids, glycolipids, sulfolipids and the like.

Further, in the present specification, the description of "Cx:y" for the fatty acid or the acyl group constituting the fatty acid represents a fatty acid or an acyl group having "x" as the number of carbon atoms, and "y" as the number of double bonds. Furthermore, the descriptions of "Cx fatty acid" and "Cx acyl" represent a fatty acid and an acyl group having "x" as the number of carbon atoms, respectively.

Hereinafter, in the present specification, "acyl-ACP thioesterase" is also simply referred to as "TE", and the gene encoding the TE is also simply referred to as "acyl-ACP thioesterase gene" or "TE gene".

Hereinafter, the acyl-ACP thioesterase variant, the gene encoding the acyl-ACP thioesterase variant, the transformant using the same, and the method of producing a lipid of the present invention are described below in order.

1. Acyl-ACP Thioesterase Variant

The protein of the present invention (hereinafter, also referred to as "acyl-ACP thioesterase variant" or "TE variant") includes a protein having an amino acid sequence set forth in SEQ ID NO: 1 in which a part of the amino acid sequence is modified, and having acyl-ACP thioesterase activity (hereinafter, also referred to as "TE activity"); and a protein functionally equivalent to the protein.

The acyl-ACP thioesterase is an enzyme involved in the biosynthesis pathway of fatty acids and derivatives thereof (such as triacylglycerol (triglyceride)). This enzyme hydrolyzes a thioester bond of an acyl-ACP to form free fatty acids in a plastid such as a chloroplast of plants and algae or in a cytoplasm of bacteria, fungi and animals. The acyl-ACP is a composite composed of an acyl group as a fatty add residue and an acyl carrier protein, and is an intermediate in the process of fatty acid biosynthesis. The function of the TE terminates the synthesis of the fatty acid on the ACP, and then the thus-produced free fatty acids are supplied to the synthesis of triglyceride and the like. To date, several TEs having different reaction specificities depending on the number of carbon atoms and the number of unsaturated bonds of the acyl group (fatty acid residue) of the acyl-ACP substrate are identified. Therefore, TE is considered to be an important factor in determining the fatty acid composition in vivo.

The "acyl-ACP thioesterase activity" described in this specification means an activity of hydrolyzing the thioester bond of the acyl-ACP.

Specific examples of the TE variant of the present invention include the following proteins (A) to (C).

(A) A protein consisting of an amino acid sequence of the 128th to 287th positions set forth in SEQ ID NO: 1 in which at least one of the glycine of the 203rd position and the valine of the 204th position set forth in SEQ ID NO: 1 is substituted with tryptophan.

(B) A protein consisting of an amino acid sequence having 85% or more identity with the amino acid sequence of the 128th to 287th positions set forth in SEQ ID NO: 1, in which at least one of the amino acids corresponding to the 203rd position and the 204th position set forth in SEQ ID NO: 1 is substituted with tryptophan, and having TE activity.

(C) A protein containing the amino acid sequence of the protein (A) or (B), and having TE activity.

The amino acid sequence set forth in SEQ ID NO: 1 is an amino acid sequence of the TE (NoTE) derived from *Nannochloropsis oculata* strain NIES2145, which is an alga belonging to the genus *Nannochloropsis*.

The present inventors found that the region of the 128th to 287th positions in the amino acid sequence set forth in SEQ ID NO: 1 is an important and sufficient region for exhibiting the TE activity. That is, the protein consisting of the amino acid sequence of the 128th to 287th positions set forth in SEQ ID NO: 1 has the TE activity.

The protein (A) has a region sufficient for this TE activity, and acts as the TE.

The amino acid sequence of the protein (A) basically consists of the amino acid sequence at the 128th to 287th positions set forth in SEQ ID NO: 1, being a sufficient region for TE activity, in which an amino acid at a specific position in the sequence is further substituted. In the TE variant in which an amino acid at the position as described later in the SEQ ID NO: 1 is substituted, specificity to the acyl-ACP having the specific number of carbon atoms, particularly to at least one kind of acyl-ACP selected from the group consisting of C8 acyl-ACP, C10 acyl-ACP and C12 acyl-ACP is improved. That is, in comparison with the wild type TE, the TE variant of the present invention selectively utilizes as a substrate acyl-ACP having the specific number of carbon atoms (specifically, at least one kind of acyl-ACP selected from the group consisting of C8 acyl-ACP, C10 acyl-ACP and C12 acyl-ACP) and has higher activity of hydrolyzing this substrate.

With respect to the protein (A), at least one of the amino acids of the 203rd and 204th positions is substituted with tryptophan in the amino acid sequence of the 128th to 287th positions set forth in SEQ ID NO: 1. In the wild type TE having the amino acid sequence set forth in SEQ ID NO: 1, the amino add of the 203rd position is glycine, and the amino acid of the 204th position is valine.

From a viewpoint of improving the specificity to the acyl-ACP having the specific number of carbon atoms, particularly to at least one kind of acyl-ACP selected from the group consisting of C8 acyl-ACP, C10 acyl-ACP and C12 acyl-ACP, in the protein (A), it is preferable that the glycine of the 203rd position set forth in SEQ ID NO: 1 is substituted with tryptophan, and the valine of the 204th position set forth in SEQ ID NO: 1 is substituted with tryptophan or phenylalanine; and it is more preferable that the glycine of the 203rd position and the valine of the 204th position set forth in SEQ ID NO: 1 are substituted with tryptophan, respectively.

In the present specification, the TE variant having specific amino acid substitution is abbreviated as follows in several cases.

NoTE(G203W): A TE variant derived from *Nannochloropsis oculata* in which the glycine (Gly; G) at the 203rd position set forth in SEQ ID NO: 1 is substituted with tryptophan (Trp; W).

NoTE(G203W+V204F): A TE variant derived from *Nannochloropsis oculata* in which the glycine (Gly; G) at the 203rd position set forth in SEQ ID NO: 1 is substituted with tryptophan (Trp; W), and the valine (Val; V) at the 204th position set forth in SEQ ID NO: 1 is substituted with phenylalanine (Phe; F).

Further, the protein (A) may have amino acid substitution at a position other than the 203rd and 204th positions set forth in SEQ ID NO: 1. For example, from a viewpoint of Improving the specificity to the acyl-ACP having the specific number of carbon atoms, it is preferable that at least one selected from the group consisting of the following amino acid substitutions (Ca-1) to (Cg-1) is further Introduced into the amino acid sequence of the protein (A).

(Ca-1) The leucine (Leu; L) of the 143rd position set forth in SEQ ID NO: 1 is substituted with proline (Pro; P).
(Cb-1) The histidine (His; H) of the 146th position set forth in SEQ ID NO: 1 is substituted with asparagine (Asn; N) or serine (Ser S).
(Cc-1) The glycine (Gly; G) of the 160th position set forth in SEQ ID NO: 1 is substituted with alanine (Ala; A).
(Cd-1) The methionine (Met; M) of the 202nd position set forth in SEQ ID NO: 1 is substituted with phenylalanine (Phe; F), histidine (His; H), leucine (Leu; L), glutamine (Gln; Q), or valine (Val; V).
(Ce-1) The glycine (Gly; G) of the 212th position set forth in SEQ ID NO: 1 is substituted with proline (Pro; P).
(Cf-1) The asparagine (Asn; N) of the 213th position set forth in SEQ ID NO: 1 is substituted with tyrosine (Tyr Y).
(Cg-1) The proline (Pro; P) of the 281st position set forth in SEQ ID NO: 1 is substituted with glutamine (Gln; Q).

It is more preferable that the glycine of the 203rd position and the valine of the 204th position set forth in SEQ ID NO: 1 are substituted with tryptophan in the amino acid sequence of the protein (A), respectively, and one or two selected from the group consisting of the amino acid substitutions (Ca-1) to (Cg-1) are introduced into the amino acid sequence of the protein (A). Alternatively, it is more preferable that the valine of the 204th position set forth in SEQ ID NO: 1 is substituted with tryptophan in the amino acid sequence of the protein (A), and one or two selected from the group consisting of the amino acid substitutions (Ca-1) to (Cg-1) are introduced into the amino acid sequence of the protein (A).

The protein (B) basically consists of an amino acid sequence having 85% or more identity with the amino acid sequence of the 128th to 287th positions set forth in SEQ ID NO: 1, and has TE activity.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the TE activity is kept and a part of the amino acid sequence set forth in SEQ ID NO: 1 is subjected to mutation.

In the present specification, the identity of the amino acid sequence and nucleotide sequence is calculated through the Lipman-Pearson method (see Science, 1985, vol. 227, p. 1435-1441). Specifically, the identity can be determined through use of a homology analysis (homology search) program of genetic information processing software Genetyx-Win (Software Development Co., Ltd.) with the Unit size to compare (ktup) being set to 2.

Further, the amino acid sequence of the protein (B) has, in the amino acid sequence having 85% or more identity with the amino acid sequence of the 128th to 287th positions set forth in SEQ ID NO: 1, amino acid substitution similar to the amino acid substitution in the protein (A). That is, at least one of the amino acids corresponding to the 203rd position and the 204th position set forth in SEQ ID NO: 1 is substituted with tryptophan in the amino acid sequence of the protein (B).

As well as the above-described protein (A), in the amino acid sequence of the protein (B), it is also preferable the amino acid corresponding to the 203rd position set forth in SEQ ID NO: 1 is substituted with tryptophan and the amino acid corresponding to the 204th position set forth in SEQ ID NO: 1 is substituted with tryptophan or phenylalanine; and more preferable that the amino acids corresponding to the 203rd position and the 204th position set forth in SEQ ID NO: 1 are substituted with tryptophan, respectively.

Further, the protein (B) may have amino acid substitution at a position other than the positions corresponding to the 203rd and 204th positions set forth in SEQ ID NO: 1. For example, it is preferable that at least one selected from the group consisting of the following amino acid substitutions (Ca-2) to (Cg-2) is further introduced into the amino acid sequence of the protein (B).

(Ca-2) The amino acid corresponding to the 143rd position set forth in SEQ ID NO: 1 is substituted with proline.
(Cb-2) The amino acid corresponding to the 146th position set forth in SEQ ID NO: 1 is substituted with asparagine or serine.
(Cc-2) The amino acid corresponding to the 160th position set forth in SEQ ID NO: 1 is substituted with alanine.
(Cd-2) The amino acid corresponding to the 202nd position set forth in SEQ ID NO: 1 is substituted with phenylalanine, histidine, leucine, glutamine, or valine.
(Ce-2) The amino acid corresponding to the 212th position set forth in SEQ ID NO: 1 is substituted with proline.
(Cf-2) The amino acid corresponding to the 213th position set forth in SEQ ID NO: 1 is substituted with tyrosine.
(Cg-2) The amino acid corresponding to the 281st position set forth in SEQ ID NO: 1 is substituted with glutamine.

It is more preferable that the amino adds corresponding to the 203rd position and the 204th position set forth in SEQ ID NO: 1 are substituted with tryptophan in the amino acid sequence of the protein (B), respectively, and one or two selected from the group consisting of the amino acid substitutions (Ca-2) to (Cg-2) are further introduced into the amino acid sequence of the protein (B). Alternatively, it is more preferable that the amino acids corresponding to the 204th position set forth in SEQ ID NO: 1 is substituted with tryptophan in the amino acid sequence of the protein (B), and one or two selected from the group consisting of the amino acid substitutions (Ca-2) to (Cg-2) are further introduced into the amino acid sequence of the protein (B).

The term "position corresponding thereto" or "region corresponding thereto" in the amino acid sequence or the nucleotide sequence described in the present specification can be determined by comparing an objective amino acid sequence with a reference sequence to align (provide alignment to) the sequence so as to give the maximum homology for a conserved amino acid residue existing in each amino acid sequence. The alignment can be executed by using a publicly known algorithm, and the procedures are publicly known to a person skilled in the art. The alignment can be manually performed, for example, based on the Lipman-Pearson method mentioned above; or alternatively, can be performed by using the Clustal W multiple alignment program (Thompson, J. D. et al, Nucleic Acids Res., 1994, vol. 22, p. 4673-4680) by default. The Clustal W is available from websites: for example, European Bioinformatics Institute: (EBI, [www.ebi.ac.uk/index.html]) and DNA Data Bank of Japan (DDBJ, [www.ddbj.nig.ac.jp/Welcome-j.html]) managed by the National Institute of Genetics.

Examples of the amino acid sequence having the 85% or more Identity with the amino acid sequence of the 128th to 287th positions set forth in SEQ ID NO: 1 include the amino acid sequence of the 115th to 274th positions set forth in SEQ ID NO: 3, and the amino acid sequence of the 126th to 285th positions set forth in SEQ ID NO: 49. The amino acid sequence set forth in SEQ ID NO: 3 is an amino acid sequence of the TE (NgTE) derived from *Nannochloropsis gaditana* strain CCMP526. The amino acid sequence set forth in SEQ ID NO: 49 is an amino acid sequence of the TE (NgrTE) derived from *Nannochloropsis granulata* strain NIES2588.

Herein, a protein consisting of the amino acid sequence set forth in SEQ ID NO: 1, 3 or 49 or a partial sequence thereof is referred to as "wild type TE", and a protein consisting of an amino acid sequence in which a part of the amino acid sequence of the wild type TE is subjected to mutation is referred to as "TE variant."

As shown in FIG. 1, the amino acid sequence of the 128th to 287th positions set forth in SEQ ID NO: 1, the amino acid sequence of the 115th to 274th positions set forth in SEQ ID NO: 3, and the amino acid sequence of the 126th to 285th positions set forth in SEQ ID NO: 49 have high identity with each other. The identity between the amino acid sequence of the 128th to 287th positions set forth in SEQ ID NO: 1 and the amino acid sequence of the 115th to 274th positions set forth in SEQ ID NO: 3 is about 91%. Further, the identity between the amino acid sequence of the 128th to 287th positions set forth in SEQ ID NO: 1 and the amino acid sequence of the 126th to 285th positions set forth in SEQ ID NO: 49 is about 98%.

The present inventors confirmed that the region of the 115th to 274th positions in the amino acid sequence set forth in SEQ ID NO: 3 and the region of the 126th to 285th positions in the amino acid sequence set forth in SEQ ID NO: 49 are also important for acting the TE, and sufficient for exhibiting the TE activity, as well as the amino acid sequence set forth in SEQ ID NO: 1. Therefore, the protein consisting of the amino acid sequence of the 115th to 274th positions set forth in SEQ ID NO: 3, and the protein consisting of the amino acid sequence of the 126th to 285th positions set forth in SEQ ID NO: 49 also have the TE activity.

The protein (B) is preferably the following protein (Ba) or (Bb).
(Ba) A protein consisting of an amino acid sequence of the 115th to 274th positions set forth in SEQ ID NO: 3, in which at least one of the glycine of the 190th position and the valine of the 191st position set forth in SEQ ID NO: 3 is substituted with tryptophan, and having TE activity.
(Bb) A protein consisting of an amino acid sequence of the 126th to 285th positions set forth in SEQ ID NO: 49, in which at least one of the glycine of the 201st position and the valine of the 202nd position set forth in SEQ ID NO: 49 is substituted with tryptophan, and having TE activity.

As shown in FIG. 1, the glycine at the 203rd position, the valine at the 204th position, the leucine at the 143rd position, the histidine at the 146th position, the glycine at the 160th position, the methionine at the 202nd position, the glycine at the 212th position, the asparagine at the 213th position, and the proline at the 281st position set forth in SEQ ID NO: 1 are corresponding to the glycine at the 190th position, the valine at the 191st position, the leucine at the 130th position, the histidine at the 133rd position, the glycine at the 147th position, the methionine at the 189th position, the glycine at the 199th position, the asparagine at the 200th position, and the proline at the 268th position set forth in SEQ ID NO: 3, respectively.

In addition, the glycine at the 203rd position, the valine at the 204th position, the leucine at the 143rd position, the histidine at the 146th position, the glycine at the 160th position, the methionine at the 202nd position, the glycine at the 212th position, the asparagine at the 213th position, and the proline at the 281st position set forth in SEQ ID NO: 1 are corresponding to the glycine at the 201st position, the valine at the 202nd position, the leucine at the 141st position, the histidine at the 144th position, the glycine at the 158th position, the methionine at the 200th position, the glycine at the 210th position, the asparagine at the 211th position, and the proline at the 279th position set forth in SEQ ID NO: 49, respectively.

Also the amino acid sequences of the proteins (Ba) and (Bb) are preferably substituted in a manner similar to the protein (A).

With respect to the protein (Ba), the specificity to the acyl-ACP having the specific number of carbon atoms is improved in a manner similar to the protein (A). The amino acid sequence of the protein (Ba) has about 90% identity with the amino acid sequence of the protein (A). Therefore, the protein (B) has preferably 86% or more identity, more preferably 88% or more identity, and further preferably 90% or more identity, with the amino acid sequence of the 128th to 287th positions set forth in SEQ ID NO: 1.

Further, with respect to the protein (B), as the amino acid sequence having 85% or more identity with the amino acid sequence of the 128th to 287th positions set forth in SEQ ID NO: 1, a protein consisting of an amino acid sequence in which 1 or several amino acids (preferably 1 to 8 amino acids, more preferably 1 to 5 amino acids, further preferably 1 to 4 amino acids, furthermore preferably 1 to 3 amino acids, furthermore preferably 1 to 2 amino acids) are deleted, substituted, inserted or added in the amino acid sequence of the 128th to 287th positions set forth in SEQ ID NO: 1, the 115th to 274th positions set forth in SEQ ID NO: 3, or the 126th to 285th positions set forth in SEQ ID NO: 49, is also preferable.

A method of introducing the mutation such as deletion, substitution, addition or Insertion into an amino acid sequence includes a method of, for example, introducing a mutation into a nucleotide sequence encoding the amino acid sequence. The method of introducing a mutation into a nucleotide sequence is described later.

The protein (C) contains the amino acid sequence of the protein (A) or (B) as a part of the amino acid sequence of the protein (C), and exhibits TE activity.

Specific examples of the sequence other than the amino acid sequence of the protein (A) or (B) in the amino acid sequence that constitutes the protein (C) include an arbitrary amino acid sequence other than the 128th to 287th positions set forth in SEQ ID NO: 1, an arbitrary amino acid sequence other than the 115th to 274th positions set forth in SEQ ID NO: 3, an arbitrary amino acid sequence other than the 126th to 285th positions set forth in SEQ ID NO: 49, or an amino acid sequence in which one or several mutations (preferably 1 or more and 20 or less, more preferably 1 or more and 15 or less, further preferably 1 or more and 10 or less, furthermore preferably 1 or more and 5 or less, and furthermore preferably 1 or more and 3 or less) are introduced into these sequences. The above amino acid mutation includes deletion, substitution, insertion or addition of amino acid(s). These sequences are preferably added to the N-terminal side of the amino acid sequence of the protein (A) or (B).

Moreover, the protein (C) also preferably includes a protein consisting of an amino acid sequence formed such that a signal peptide engaging in transport or secretion of the protein is added to the amino acid sequence of the protein (A) or (B). Specific examples of addition of the signal peptide include addition to an N-terminal of chloroplast transit peptide.

The protein (C) preferably consists of an amino acid sequence in which the amino acid sequence of the 1st to 127th positions set forth in SEQ ID NO: 1, the amino acid sequence of the 49th to 127th positions set forth in SEQ ID NO: 1, the amino acid sequence of the 58th to 127th positions set forth in SEQ ID NO: 1, the amino acid sequence of the 78th to 127th positions set forth in SEQ ID NO: 1, the amino acid sequence of the 87th to 127th positions set forth in SEQ ID NO: 1, the amino acid sequence of the 88th to 127th positions set forth in SEQ ID NO: 1, the amino acid sequence of the 98th to 127th positions set forth in SEQ ID NO: 1, the amino acid sequence of the 108th to 127th positions set forth in SEQ ID NO: 1, the amino acid sequence of the 118th to 127th positions set forth in SEQ ID NO: 1, or an amino acid sequence in which 1 or several amino acids (preferably 1 or more and 20 or less amino acids, more preferably 1 or more and 15 or less amino acids, further preferably 1 or more and 10 or less amino acids, furthermore preferably 1 or more and 5 or less amino acids, and furthermore preferably 1 or more and 3 or less amino acids) are mutated (deleted, substituted, Inserted or added) to any one of these amino acid sequences, is added to the N-terminal of the amino acid sequence of the protein (A). The present inventors confirmed that the protein consisting of the amino acid sequence set forth in SEQ ID NO: 1, the protein consisting of the amino acid sequence of the 49th to 287th positions set forth in SEQ ID NO: 1, the protein consisting of the amino acid sequence of the 58th to 287th positions set forth in SEQ ID NO: 1, the protein consisting of the amino acid sequence of the 78th to 287th positions set forth in SEQ ID NO: 1, the protein consisting of the amino acid sequence of the 87th to 287th positions set forth in SEQ ID NO: 1, the protein consisting of the amino acid sequence of the 88th to 287th positions set forth in SEQ ID NO: 1, the protein consisting of the amino acid sequence of the 98th to 287th positions set forth in SEQ ID NO: 1, the protein consisting of the amino add sequence of the 108th to 287th positions set forth in SEQ ID NO: 1, and the protein consisting of the amino add sequence of the 118th to 287th positions set forth in SEQ ID NO: 1, have the TE activity.

Further, the protein (C) preferably consists of an amino acid sequence in which the amino acid sequence of the 36th to 114th positions set forth in SEQ ID NO: 3, the amino acid sequence of the 45th to 114th positions set forth in SEQ ID NO: 3, the amino acid sequence of the 55th to 114th positions set forth in SEQ ID NO: 3, the amino acid sequence of the 65th to 114th positions set forth in SEQ ID NO: 3, the amino acid sequence of the 75th to 114th positions set forth in SEQ ID NO: 3, the amino acid sequence of the 85th to 114th positions set forth in SEQ ID NO: 3, the amino acid sequence of the 95th to 114th positions set forth in SEQ ID NO: 3, the amino acid sequence of the 105th to 114th positions set forth in SEQ ID NO: 3, or an amino acid sequence in which 1 or several amino acids (preferably 1 or more and 20 or less amino acids, more preferably 1 or more and 15 or less amino acids, further preferably 1 or more and 10 or less amino acids, furthermore preferably 1 or more and 5 or less amino acids, and furthermore preferably 1 or more and 3 or less amino acids) are mutated (deleted, substituted, inserted or added) to any one of these amino acid sequences, is added to the N-terminal of the amino acid sequence of the protein (Ba). The present inventors confirmed that the protein consisting of the amino acid sequence of the 36th to 274th positions set forth in SEQ ID NO: 3, the protein consisting of the amino acid sequence of the 45th to 274th positions set forth in SEQ ID NO: 3, the protein consisting of the amino acid sequence of the 55th to 274th positions set forth in SEQ ID NO: 3, the protein consisting of the amino acid sequence of t the 65th to 274th positions set forth in SEQ ID NO: 3, the protein consisting of the amino acid sequence of the 75th to 274th positions set forth in SEQ ID NO: 3, the protein consisting of the amino acid sequence of the 85th to 274th positions set forth in SEQ ID NO: 3, the protein consisting of the amino acid sequence of the 95th to 274th positions set forth in SEQ ID NO: 3, and the protein consisting of the amino acid sequence of the 105th to 274th positions set forth in SEQ ID NO: 3, have the TE activity.

Furthermore, the protein (C) preferably consists of an amino acid sequence in which the amino acid sequence of the 1st to 125th positions set forth in SEQ ID NO: 49, the amino acid sequence of the 35th to 125th positions set forth in SEQ ID NO: 49, the amino acid sequence of the 55th to 125th positions set forth in SEQ ID NO: 49, the amino acid sequence of the 85th to 125th positions set forth in SEQ ID NO: 49, or an amino acid sequence in which 1 or several amino acids (preferably 1 or more and 20 or less amino acids, more preferably 1 or more and 15 or less amino acids, further preferably 1 or more and 10 or less amino acids, furthermore preferably 1 or more and 5 or less amino acids, and furthermore preferably 1 or more and 3 or less amino acids) are mutated (deleted, substituted, inserted or added) to any one of these amino acid sequences, is added to the N-terminal of the amino acid sequence of the protein (Bb). The present inventors confirmed that the protein consisting of the amino acid sequence set forth in SEQ ID NO: 49, the protein consisting of the amino acid sequence of the 35th to 285th positions set forth in SEQ ID NO: 49, the protein consisting of the amino acid sequence of the 55th to 285th positions set forth in SEQ ID NO: 49, and the protein consisting of the amino acid sequence of the 85th to 285th positions set forth in SEQ ID NO: 49, have the TE activity.

The protein (C) is preferably a protein consisting of an amino acid sequence in which at least one of the amino acids corresponding to the 203rd position and the 204th position set forth in SEQ ID NO: 1 is substituted with tryptophan in the amino acid sequence set forth in SEQ ID NO: 1, 3 or 49, and having TE activity.

Further, the protein (C) may be a protein consisting of an amino acid sequence that has, in the amino acid sequence set forth in SEQ ID NO: 1, 3 or 49, the above-mentioned amino acid substitution, and in which amino acids on an N-terminal side are deleted at an arbitrary position of the 1st to 127th positions set forth in SEQ ID NO: 1, the 1st to 114th positions set forth in SEQ ID NO: 3 or the 1st to 125th positions forth in SEQ ID NO: 49, respectively.

The TE activity of the TE variant of the present invention can be confirmed by, for example, introducing a fusion gene produced by linking the TE gene to the downstream of a promoter which functions in a host cell such as *Escherichia coli*, into a host cell which lacks a fatty acid degradation system, culturing the thus-obtained cell under the conditions suitable for the expression of the introduced TE gene, and analyzing any change caused thereby in the fatty acid composition of the host cell or the cultured liquid by using a gas chromatographic analysis or the like. In this case, a change in the specificity to the acyl-ACP having the specific number of carbon atoms in the TE variant can be confirmed by comparing a proportion of fatty acids having the specific number of carbon atoms each in the total amount of fatty acids with a proportion of a system in which the wild type TE is expressed.

Alternatively, the TE activity can be measured by introducing a fusion gene produced by linking the TE gene to the downstream of a promoter which functions in a host cell such as *Escherichia coli*, into a host cell, culturing the thus-obtained cell under the conditions suitable for the expression of the introduced TE gene, and subjecting a disruption liquid of the cell to a reaction which uses acyl-ACPs, as substrates, prepared according to the method of Yuan et al. (Yuan L. et al., Proc. Natl. Acad. Sci. U.S.A., 1995, vol. 92 (23), p. 10639-10643).

There are no particular limitations on the method for obtaining the protein of the present invention, and the protein can be obtained by chemical techniques, genetic engineering techniques or the like that are ordinarily carried out. Furthermore, protein synthesis may be carried out by chemical synthesis, or a recombinant protein may also be produced by gene recombination technologies. For example, the TE variant can be obtained by modifying a TE gene cloned from *Nannochloropsis oculata*, according to a gene recombination technology.

Moreover, the algae belonging to the genus *Nannochloropsis* such as *Nannochloropsis oculata* can be obtained from The culture collection of algae at University of Texas at Austin (UTEX), National Institute for Environmental Studies (NIES), National Center for Marine Algae and Microbiota (NCMA, previous name: CCMP), Culture Collection of Algae and Protozoa (CCAP), Australian National Algae Culture Collection (CSIRO), or the like, 2. Gene Encoding Acyl-ACP Thioesterase Variant The gene of the present invention is a gene encoding any one of the proteins (A) to (C).

Examples of the gene encoding the amino acid sequence set forth in SEQ ID NO: 1, include a gene consisting of the nucleotide sequence set forth in SEQ ID NO: 2. The nucleotide sequence set forth in SEQ ID NO: 2 is the nucleotide sequence of the gene encoding the wild type TE derived from *Nannochloropsis oculata* strain NIES2145. The nucleotide sequence of the 382nd to 864th positions set forth in SEQ ID NO: 2 encodes the amino acid sequence of the 128th to 287th positions set forth in SEQ ID NO: 1.

Examples of the gene encoding the amino add sequence set forth in SEQ ID NO: 3, Include a gene consisting of the nucleotide sequence set forth in SEQ ID NO: 4. The nucleotide sequence set forth in SEQ ID NO: 4 is the nucleotide sequence of the gene encoding the wild type TE derived from *Nannochloropsis gaditana* strain CCMP526. The nucleotide sequence of the 343rd to 825th positions set forth in SEQ ID NO: 4 encodes the amino acid sequence of the 115th to 274th positions set forth in SEQ ID NO: 3. The nucleotide sequence of the 343rd to 825th positions set forth in SEQ ID NO: 4 has about 76% identity with the nucleotide sequence of the 382nd to 864th positions set forth in SEQ ID NO: 2.

Examples of the gene encoding the amino acid sequence set forth in SEQ ID NO: 49, include a gene consisting of the nucleotide sequence set forth in SEQ ID NO: 50. The nucleotide sequence set forth in SEQ ID NO: 50 is the nucleotide sequence of the gene encoding the wild type TE derived from *Nannochloropsis granulata* strain NIES2588. The nucleotide sequence of the 376th to 858th positions set forth in SEQ ID NO: 50 encodes the amino acid sequence of the 126th to 285th positions set forth in SEQ ID NO: 49. The nucleotide sequence of the 376th to 858th positions set forth in SEQ ID NO: 50 has about 93% identity with the nucleotide sequence of the 382nd to 864th positions set forth in SEQ ID NO: 2.

Specific examples of the gene encoding any one of the proteins (A) to (C) include a gene consisting of any one of the following DNAs (A1) to (C1). However, the present invention is not limited thereto.

(A1) A DNA consisting of a nucleotide sequence of the 382nd to 864th positions set forth in SEQ ID NO: 2, in which at least one set of the nucleotides of the 607th to 609th positions and the nucleotides of the 610th to 612th positions set forth in SEQ ID NO: 2 is substituted with nucleotides encoding tryptophan.

(B1) A DNA consisting of a nucleotide sequence having 70% or more identity with the nucleotide sequence of the 382nd to 864th positions set forth in SEQ ID NO: 2, in which at least one set of the nucleotides corresponding to the 607th to 609th positions and the nucleotides corresponding to the 610th to 612th positions set forth in SEQ ID NO: 2 is substituted with nucleotides encoding tryptophan, and encoding a protein having TE activity.

(C1) A DNA containing the nucleotide sequence of the DNA (A1) or (B1), and encoding a protein having TE activity.

The gene consisting of the DNA (A1) is a gene encoding the protein (A).

In the nucleotide sequence of the gene consisting of the DNA (A1), it is preferable that the nucleotides (codon) of the 607th to 609th positions set forth in SEQ ID NO: 2 are substituted with nucleotides encoding tryptophan and the nucleotides of the 610th to 612th positions set forth in SEQ ID NO: 2 are substituted with nucleotides encoding tryptophan or phenylalanine, and more preferable that the nucleotides of the 607th to 609th positions and the nucleotides of the 610th to 612th positions set forth in SEQ ID NO: 2 are substituted with nucleotides encoding tryptophan, respectively.

Further, the nucleotide sequence in the gene consisting of the DNA (A1) may have a nucleotide substitution at a position other than the 607th to 609th positions and the 610th to 612th positions set forth in SEQ ID NO: 2. For example, it is preferable that at least one selected from the group consisting of the following nucleotide substitutions (C1a-1) to (C1g-1) is further introduced into the DNA (A1).

(C1a-1) The nucleotides of the 427th to 429th positions set forth in SEQ ID NO: 2 are substituted with nucleotides encoding proline.

(C1b-1) The nucleotides of the 436th to 438th positions set forth in SEQ ID NO: 2 are substituted with nucleotides encoding asparagine or serine.

(C1c-1) The nucleotides of the 478th to 480th positions set forth in SEQ ID NO: 2 are substituted with nucleotides encoding alanine.
(C1d-1) The nucleotides of the 604th to 606th positions set forth in SEQ ID NO: 2 are substituted with nucleotides encoding phenylalanine, histidine, leucine, glutamine or valine.
(C1e-1) The nucleotides of the 634th to 636th positions set forth in SEQ ID NO: 2 are substituted with nucleotides encoding proline.
(C1f-1) The nucleotides of the 637th to 639th positions set forth in SEQ ID NO: 2 are substituted with nucleotides encoding tyrosine.
(C1g-1) The nucleotides of the 841st to 843rd positions set forth in SEQ ID NO: 2 are substituted with nucleotides encoding glutamine.

It is more preferable that the nucleotides of the 607th to 609th positions and the nucleotides of the 610th to 612th positions set forth in SEQ ID NO: 2 are substituted with nucleotides encoding tryptophan in the nucleotide sequence of the gene consisting of the DNA (A1), respectively, and one or two selected from the group consisting of the nucleotide substitutions (C1a-1) to (C1g-1) are introduced into the nucleotide sequence of the gene consisting of the DNA (A1). Alternatively, it is more preferable that the nucleotides of the 610th to 612th positions set forth in SEQ ID NO: 2 are substituted with nucleotides encoding tryptophan in the nucleotide sequence of the gene consisting of the DNA (A1), and one or two selected from the group consisting of the nucleotide substitutions (C1a-1) to (C1g-1) are introduced into the nucleotide sequence of the gene consisting of the DNA (A1).

The gene consisting of the DNA (B1) is a gene having a nucleotide substitution corresponding to the amino acid substitution of the protein (B).

It is preferable that the nucleotides corresponding to the 607th to 609th positions set forth in SEQ ID NO: 2 are substituted with nucleotides encoding tryptophan and the nucleotides corresponding to the 610th to 612th positions set forth in SEQ ID NO: 2 are substituted with nucleotides encoding tryptophan or phenylalanine in the nucleotide sequence of the gene consisting of the DNA (B1); and more preferable that the nucleotides corresponding to the 607th to 609th positions and the nucleotides corresponding to the 610th to 612th positions set forth in SEQ ID NO: 2 are substituted with nucleotides encoding tryptophan in the nucleotide sequence of the gene consisting of the DNA (B1), respectively.

Further, the nucleotide sequence in the gene consisting of the DNA (B1) may have a nucleotide substitution at a position other than the positions corresponding to the 607th to 609th positions and the positions corresponding to the 610th to 612th positions set forth in SEQ ID NO: 2. For example, it is preferable that at least one selected from the group consisting of the following nucleotide substitutions (C1a-2) to (C1g-2) is further introduced into the DNA (B 1).
(C1a-2) The nucleotides corresponding to the 427th to 429th positions set forth in SEQ ID NO: 2 are substituted with nucleotides encoding proline.
(C1b-2) The nucleotides corresponding to the 436th to 438th positions set forth in SEQ ID NO: 2 are substituted with nucleotides encoding asparagine or serine.
(C1c-2) The nucleotides corresponding to the 478th to 480th positions set forth in SEQ ID NO: 2 are substituted with nucleotides encoding alanine.
(C1d-2) The nucleotides corresponding to the 604th to 606th positions set forth in SEQ ID NO: 2 are substituted with nucleotides encoding phenylalanine, histidine, leucine, glutamine or valine.
(C1e-2) The nucleotides corresponding to the 634th to 636th positions set forth in SEQ ID NO: 2 are substituted with nucleotides encoding proline.
(C1f-2) The nucleotides corresponding to the 637th to 639th positions set forth in SEQ ID NO: 2 are substituted with nucleotides encoding tyrosine.
(C1g-2) The nucleotides corresponding to the 841st to 843rd positions set forth in SEQ ID NO: 2 are substituted with nucleotides encoding glutamine.

It is more preferable that the nucleotides corresponding to the 607th to 609th positions and the nucleotides corresponding to the 610th to 612th positions set forth in SEQ ID NO: 2 are substituted with nucleotides encoding tryptophan in the nucleotide sequence of the gene consisting of the DNA (B1), respectively, and one or two selected from the group consisting of the nucleotide substitutions (C1a-2) to (C1g-2) are introduced into the nucleotide sequence of the gene consisting of the DNA (B1). Alternatively, it is more preferable that the nucleotides corresponding to the 610th to 612th positions set forth in SEQ ID NO: 2 are substituted with nucleotides encoding tryptophan in the nucleotide sequence of the gene consisting of the DNA (B1), and one or two selected from the group consisting of the nucleotide substitutions (C1a-2) to (C1 g-2) are introduced into the nucleotide sequence of the gene consisting of the DNA (B1).

The gene consisting of the DNA (B1) is preferably a gene consisting of the following DNAs (B1a) or (B1b).
(B1a) A DNA consisting of a nucleotide sequence of the 343rd to 825th positions set forth in SEQ ID NO: 4 in which at least one set of the nucleotides of the 568th to 570th positions and the nucleotides of the 571st to 573rd positions set forth in SEQ ID NO: 4 is substituted with nucleotides encoding tryptophan, and encoding a protein having TE activity.
(B1b) A DNA consisting of a nucleotide sequence of the 376th to 858th positions set forth in SEQ ID NO: 50 in which at least one set of the nucleotides of the 601st to 603rd positions and the nucleotides of the 604th to 606th positions set forth in SEQ ID NO: 50 is substituted with nucleotides encoding tryptophan, and encoding a protein having TE activity.

The nucleotides of the 607th to 609th positions, the nucleotides of the 610th to 612nd positions, the nucleotides of the 427th to 429th positions, the nucleotides of the 436th to 438th positions, the nucleotides of the 478th to 480th positions, the nucleotides of the 604th to 606th positions, the nucleotides of the 634th to 636th positions, the nucleotides of the 637th to 639th positions, and the nucleotides of the 841st to 843rd positions set forth in SEQ ID NO: 2 correspond to the nucleotides of the 568th to 570th positions, the nucleotides of the 571st to 573rd positions, the nucleotides of the 388th to 390th positions, the nucleotides of the 397th to 399th positions, the nucleotides of the 439th to 441st positions, the nucleotides of the 565th to 567th positions, the nucleotides of the 595th to 597th positions, the nucleotides of the 598th to 600th positions, and the nucleotides of the 802nd to 804th positions set forth in SEQ ID NO: 4, respectively.

Further, the nucleotides of the 607th to 609th positions, the nucleotides of the 610th to 612nd positions, the nucleotides of the 427th to 429th positions, the nucleotides of the 436th to 438th positions, the nucleotides of the 478th to 480th positions, the nucleotides of the 604th to 606th positions, the nucleotides of the 634th to 636th positions, the nucleotides of the 637th to 639th positions, and the nucleotides of the 841st to 843rd positions set forth in SEQ ID NO: 2 correspond to the nucleotides of the 601st to 603rd positions, the nucleotides of the 604th to 606th positions, the nucleotides of the 421st to 423rd positions, the nucleotides of the 430th to 432nd positions, the nucleotides of the 472nd to 474th positions, the nucleotides of the 598th to 600th positions, the nucleotides of the 628h to 630th positions, the nucleotides of the 631st to 633rd positions, and the nucleotides of the 835th to 837th positions set forth in SEQ ID NO: 50, respectively.

Also in the nucleotide sequences of the DNA (B1a) and (Bib), these nucleotides are preferably substituted in a manner similar to the nucleotide sequence of the DNA (A1).

The DNA (B1) has preferably 72% or more Identity, more preferably 74% or more identity, and further preferably 76% or more identity, with the nucleotide sequence of the 382nd to 864th positions set forth in SEQ ID NO: 2.

Further, with respect to the DNA (B1), as the nucleotide sequence having 70% or more identity with the nucleotide sequence of the 382nd to 864th positions set forth in SEQ ID NO: 2, a nucleotide sequence in which 1 or several nucleotides (preferably 1 to 20 nucleotides, more preferably 1 to 15 nucleotides, further preferably 1 to 10 nucleotides, further preferably 1 to 5 nucleotides, further preferably 1 to 3 nucleotides) are deleted, substituted, inserted or added to the nucleotide sequence of the 382nd to 864th positions set forth in SEQ ID NO: 2, the nucleotide sequence of the 343rd to 825th positions set forth in SEQ ID NO: 4 or the nucleotide sequence of the 376th to 858th positions set forth in SEQ ID NO: 50, is also preferable.

A method of introducing the mutation such as deletion, substitution, addition or insertion into a nucleotide sequence Includes a method of Introducing a site-specific mutation, for example. Specific examples of the method of introducing the site-specific mutation include a method of utilizing the Splicing overlap extension (SOE) PCR, the ODA method, and the Kunkel method. Further, commercially available kits such as Site-Directed Mutagenesis System Mutan-SuperExpress Km kit (manufactured by Takara Bio), Transformer™ Site-Directed Mutagenesis kit (manufactured by Clonetech Laboratories), and KOD-Plus-Mutagenesis Kit (manufactured by Toyobo) can also be utilized. Furthermore, a gene containing a desired mutation can also be obtained by introducing a genetic mutation at random, and then performing an evaluation of the enzyme activities and a gene analysis thereof by an appropriate method.

The DNA (C1) contains the nucleotide sequence of the DNA (A1) or (B1) as a part of the nucleotide sequence of the DNA (C1).

Specific examples of sequences other than the nucleotide sequence of the DNA (A1) or (B1) in the nucleotide sequence of the DNA (C1) include an arbitrary nucleotide sequence other than the 382nd to 864th positions set forth in SEQ ID NO: 2, an arbitrary nucleotide sequence other than the 343rd to 825th positions set forth in SEQ ID NO: 4, an arbitrary nucleotide sequence other than the 376th to 858th positions set forth in SEQ ID NO: 50, or a nucleotide sequence in which one or several mutations (preferably 1 or more and 20 or less, more preferably 1 or more and 15 or less, further preferably 1 or more and 10 or less, furthermore preferably 1 or more and 5 or less, and furthermore preferably 1 or more and 3 or less) are introduced into these sequences. The above nucleotide mutation includes deletion, substitution, insertion or addition of nucleotide(s). Any one of these sequences are preferably added to the 5'-terminal side of the nucleotide sequence of the DNA (A1) or (B1).

Moreover, the DNA (C1) also preferably includes a DNA consisting of a nucleotide sequence formed such that a nucleotide sequence encoding a signal peptide engaging in transport or secretion of the protein is added to the nucleotide sequence of the DNA (A1) or (B1). Specific example of the signal peptide to be added thereto includes the proteins described in the protein (C). The nucleotide sequence encoding the signal peptide is preferably added to the 5'-terminal side of the nucleotide sequence of the DNA (A1) or (B1).

The DNA (C1) preferably consists of a nucleotide sequence in which the nucleotide sequence of the 1st to 381st positions set forth in SEQ ID NO: 2, the nucleotide sequence of the 145th to 381st positions set forth in SEQ ID NO: 2, the nucleotide sequence of the 172nd to 381st positions set forth in SEQ ID NO: 2, the nucleotide sequence of the 232nd to 381st positions set forth in SEQ ID NO: 2, the nucleotide sequence of the 259th to 381st positions set forth in SEQ ID NO: 2, the nucleotide sequence of the 262nd to 381st positions set forth in SEQ ID NO: 2, the nucleotide sequence of the 292nd to 381st positions set forth in SEQ ID NO: 2, the nucleotide sequence of the 322nd to 381st positions set forth in SEQ ID NO: 2, the nucleotide sequence of the 352nd to 381st positions set forth in SEQ ID NO: 2, or a nucleotide sequence in which 1 or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, and furthermore preferably 1 or more and 3 or less nucleotides) are mutated (e.g., deleted, substituted, inserted or added) to any one of these sequences, is added to the 5'-terminal side of the nucleotide sequence of the DNA (A1). The present inventors confirmed that the protein encoded by the nucleotide sequence set forth in SEQ ID NO: 2, the nucleotide sequence of the 145th to 864th positions set forth in SEQ ID NO: 2, the nucleotide sequence of the 172nd to 864th positions set forth in SEQ ID NO: 2, the nucleotide sequence of the 232nd to 864th positions set forth in SEQ ID NO: 2, the nucleotide sequence of the 259th to 864th positions set forth in SEQ ID NO: 2, the nucleotide sequence of the 262nd to 864th positions set forth in SEQ ID NO: 2, the nucleotide sequence of the 292nd to 864th positions set forth in SEQ ID NO: 2, the nucleotide sequence of the 322nd to 864th positions set forth in SEQ ID NO: 2, or the nucleotide sequence of the 352nd to 864th positions set forth in SEQ ID NO: 2, has the TE activity.

Further, the DNA (C1) also preferably consists of a nucleotide sequence in which the nucleotide sequence of the 106th to 342nd positions set forth in SEQ ID NO: 4, the nucleotide sequence of the 133rd to 342nd positions set forth in SEQ ID NO: 4, the nucleotide sequence of the 163rd to 342nd positions set forth in SEQ ID NO: 4, the nucleotide sequence of the 193rd to 342nd positions set forth in SEQ ID NO: 4, the nucleotide sequence of the 223rd to 342nd positions set forth in SEQ ID NO: 4, the nucleotide sequence of the 253rd to 342nd positions set forth in SEQ ID NO: 4, the nucleotide sequence of the 283rd to 342nd positions set forth in SEQ ID NO: 4, the nucleotide sequence of the 313th to 342nd positions set forth in SEQ ID NO: 4, or a nucleotide sequence in which 1 or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, and furthermore preferably 1 or more and 3 or less nucleotides) are mutated (e.g., deleted, substituted, inserted or added) to any one of these sequences, is added to the 5'-terminal side of the nucleotide sequence of the DNA (B1a). The present inventors confirmed that the protein encoded by the nucleotide sequence of the 106th to 825th positions set forth in SEQ ID NO: 4, the nucleotide sequence of the 133rd to 825th positions set forth in SEQ ID NO: 4, the nucleotide sequence of the 163rd to 825th positions set forth in SEQ ID NO: 4, the nucleotide sequence of the 193rd to 825th positions set forth in SEQ ID NO: 4, the nucleotide sequence of the 223rd to 825th positions set forth in SEQ ID NO: 4, the nucleotide sequence of the 253rd to 825th positions set forth in SEQ ID NO: 4, the nucleotide sequence of the 283rd to 825th positions set forth in SEQ ID NO: 4, or the nucleotide sequence of the 313rd to 825th positions set forth in SEQ ID NO: 4, has the TE activity.

Furthermore, the DNA (C1) also preferably consists of a nucleotide sequence in which the nucleotide sequence of the 1st to 375th positions set forth in SEQ ID NO: 50, the nucleotide sequence of the 103rd to 375th positions set forth in SEQ ID NO: 50, the nucleotide sequence of the 163rd to 375th positions set forth in SEQ ID NO: 50, the nucleotide sequence of the 253rd to 375th positions set forth in SEQ ID NO: 50, or a nucleotide sequence in which 1 or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, and furthermore preferably 1 or more and 3 or less nucleotides) are mutated (e.g., deleted, substituted, inserted or added) to any one of these sequences, is added to the 5'-terminal side of the nucleotide sequence of the DNA (Bib). The present inventors confirmed that the protein encoded by the nucleotide sequence set forth in SEQ ID NO: 50, the nucleotide sequence of the 103rd to 858th positions set forth in SEQ ID NO: 50, the nucleotide sequence of the 163rd to 858th positions set forth in SEQ ID NO: 50, or the nucleotide sequence of the 253rd to 858th positions set forth in SEQ ID NO: 50, has the TE activity.

The DNA (C1) preferably consists of a nucleotide sequence in which at least one set of the nucleotides corresponding to the 607th to 609th positions set forth in SEQ ID NO: 2 and the nucleotides corresponding to the 610th to 612th positions set forth in SEQ ID NO: 2 is substituted with nucleotides encoding tryptophan in the nucleotide sequence set forth in SEQ ID NO: 2, 4 or 50; and encodes a protein having the TE activity.

Further, the DNA (C1) may be a DNA consisting of a nucleotide sequence that has, in the nucleotide sequence set forth in SEQ ID NO: 2, 4 or 50, the above-mentioned nucleotide substitution, in which nucleotides on a 5'-terminal side are deleted at an arbitrary position of the 1st to 381st positions set forth in SEQ ID NO: 2, the 1st to 342nd positions set forth in SEQ ID NO: 4, or the 1st to 375th positions set forth in SEQ ID NO: 50, respectively.

As one example of a method of preparing the gene encoding the TE variant, first, a nucleotide sequence of a wild type TE gene prepared by cloning a gene from a Nannochloropsis oculata strain NIES2145 (nucleotide sequence set forth in SEQ ID NO: 2) is integrated into a vector by using an In-Fusion (registered trademark) HD Cloning Kit (Clonthech, Mountain View, Calif.). Subsequently, a DNA fragment is amplified, according to a PCR method, using the resultant vector DNA as a template, and using as a primer an oligonucleotide containing a nucleotide sequence encoding an amino acid sequence in which the amino acid corresponding to the 203rd or 204th position in the amino acid sequence set forth in SEQ ID NO: 1 is substituted to tryptophan. Herewith, a preferred example of the reaction conditions for PCR as follows: a thermal denaturation reaction of making a double-stranded DNA into single strands is carried out at 98° C. for 10 seconds; an annealing reaction of hybridizing a primer pair with the single-stranded DNA is carried out at 55° C. for about 10 seconds; an elongation reaction of operating a DNA polymerase is carried out at 72° C. for about 30 seconds; and a process consisting of these three reactions as one cycle is carried out in 30 cycles.

The DNA amplified according to PCR is treated with a DpnI enzyme that specifically cleaves a methylated DNA. Eschericia coli is transformed using the resultant treated material, and the resultant product is selected in an antibiotic-containing plate medium. Plasmids are extracted from the transformed Eschericia coli, and thus a gene encoding the TE variant having a target amino acid mutation can be obtained.

3. Transformant

The transformant of the present invention is obtained by introducing a gene that encodes any one of the proteins (A) to (C) into a host. In the transformant, in comparison with the transformant having introduced wild type TE gene derived from algae belonging to the genus Nannochloropsis, the ability to produce a lipid having the specific number of carbon atoms, particularly the ability to produce C8 fatty acids, C10 fatty acids or C12 fatty acids, or a lipid containing these fatty acids as components is significantly improved. Moreover, in the transformant, in comparison with the transformant having introduced wild type TE gene, the fatty acid composition in the lipid to be produced changes by improvement of productivity of the above-mentioned fatty acids having the specific number of carbon atoms. The ability to produce fatty acids and lipids of the host or the transformant can be measured by the method used in the Examples.

The transformant of the present invention is obtained by introducing a TE gene that encodes the TE variant into a host according to an ordinarily genetic engineering method. Specifically, the transformant can be produced by preparing a gene expression vector or a gene expression cassette which is capable of expressing a gene that encodes the TE variant in a host cell, introducing this vector or cassette into host cells, and thereby transforming the host cells.

The host for the transformant can be appropriately selected from ordinarily used hosts. Specific examples of the hosts that can be used in the present invention include microorganisms (including algae and microalgae), plants or animals. Among these, microorganisms or plants are preferable, and microorganisms are more preferable as a host, from the viewpoints of production efficiency and the usability of lipids to be obtained.

As the microorganisms, prokaryotes and eukaryotes can be used. Prokaryotes Include microorganisms belonging to the genus Escherichia, microorganisms belonging to the genus Bacillus or the like. Eukaryotes include eukaryotic microorganisms belonging to yeast, filamentous fungi or the like. Among these, from the viewpoint of the productivity of lipids, Escherichia coli, Bacillus subtilis, Rhodosordium toruloides, and Mortierella sp. are preferable, and Escherichia coli is more preferable.

As the algae or microalgae, from a viewpoint of establishment of a gene recombination technique, algae belonging to the genus Chlamydomonas, algae belonging to the genus Chlorella, algae belonging to the genus Phaeodactylum, or algae belonging to the genus Nannochloropsis are preferable, and algae belonging to the genus Nannochlorop-

*sis* are more preferable. Specific examples of the algae belonging to the genus *Nannochloropsis* include *Nannochloropsis oculata, Nannochloropsis gaditana, Nannochloropsis saline Nannochloropsis oceanica, Nannochloropsis atomus, Nannochloropsis maculata, Nannochloropsis granulata*, and *Nannochloropsis* sp. Among these, from the viewpoint of the productivity of lipids, *Nannochloropsis oculata* or *Nannochloropsis gaditana* is preferable, and *Nannochloropsis oculata* is more preferable.

As the plants, from the viewpoint of a high lipid content of seeds, *Arabidopsis thaliana* rapeseed, *Cocos nucifera*, palm, cuphea, or *Jatropha curcas* is preferable, and *Arabidopsis thaliana* is more preferable.

A vector for use as the gene expression vector (plasmid) may be any vector capable of introducing the gene encoding the TE variant into a host, and expressing the gene in the host cell. For example, a vector which has expression regulation regions such as a promoter and a terminator in accordance with the type of the host to be used, and has a replication Initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector for gene expression that can be preferably used in the present invention include, in the case of using a microorganism as the host, pBluescript (pBS) II SK(−) (manufactured by Stratagene), a pSTV-based vector (manufactured by Takara Bio), pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (Mckenzie, T. et al., (1986), Plasmid 15(2); p. 93-103), pBR322 (manufactured by Takara Bio), pRS403 (manufactured by Stratagene), and pMW218/219 (manufactured by Nippon Gene). In particular, in the case of using *Escherichia coli* as the host, pBluescript II SK(−) or pMW218/219 is preferably used.

When the algae or microalgae are used as the host, specific examples of the vector include pUC19 (manufactured by Takara Bio), P66 (*Chlamydomonas* Center), P-322 (*Chlamydomonas* Center), pPha-T1 (see Non-Patent Literature 2) and pJET1 (manufactured by COSMO BIO). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Oliver Kilian, et al., Proceedings of the National Academy of Sciences of the United States of America, December 27; 108(52), 2011, by using the DNA fragment consisting of the gene of the present invention, a promoter and a terminator (gene expression cassette). Specific examples of this DNA fragment include a PCR-amplified DNA fragment and a restriction enzyme-cut DNA fragment.

In the case of using a plant cell as the host, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host, a pRI-based vector or a pBI-based vector Is preferably used.

The expression regulation regions such as a promoter and a terminator used for the expression vector and the gene expression cassette can be also appropriately selected in accordance with the type of the host and vector to be used.

Specific examples of the promoter that can be preferably used in the present invention include lac promoter, trp promoter, tac promoter, trc promoter, T7 promoter, SpoVG promoter, cauliflower mosaic virus 35S RNA promoter, promoters for housekeeping genes (e.g., tubulin promoter, actin promoter and ubiquitin promoter), rapeseed-derived *Napin* gene promoter, plant-derived Rubisco promoter, and a promoter of a violaxanthin/(chlorophyll a)-binding protein gene derived from the genus *Nannochloropsis*.

Moreover, a kind of selection marker for confirming Introduction of the gene encoding an objective protein can also be appropriately selected according to a kind of the host or the vector to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

The expression vector for transformation can be constructed by introducing the gene encoding the TE variant into the above-described vector according to an ordinary technique such as restriction enzyme treatment and ligation.

A transformation method can be appropriately selected from an ordinarily method according to the kind of the host or the vector to be used. For example, a method of using calcium ion, a general competent cell transformation method (J. Bacterial. 93, 1925 (1967)), a protoplast transformation method, an electroporation method, or an LP transformation method, can be used. When the host is the algae belonging to the genus *Nannochloropsis*, transformation can also be performed by using the electroporation method described in Randor Radakovits, et al., Nature Communications, DOI: 10.1038/ncomms1688, 2012, or the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR using a genome as a template and the like.

4. Method of Producing Lipid

The method of producing a lipid of the present invention contains a step of culturing a transformant produced by introducing a gene encoding the TE variant, to produce a lipid. From the viewpoint of improvement in the productivity of lipids, the process preferably includes a step of obtaining a cultured product by culturing, under suitable conditions, the transformant having the introduced gene encoding the TE variant; and a step of collecting the lipid from the resulting cultured product. Herein, the expression "culture the transformant" described in the present specification means culturing or growing of the microorganisms, the algae, the plants or the animals, or cells or tissues thereof, also including cultivating of the plants in soil or the like. Moreover, the "cultured product" includes a transformant itself subjected to cultivation or the like, in addition to medium used for culture of the transformant.

The culture condition can be appropriately selected in accordance with the host of the transformant.

Further, from the viewpoint of the production efficiency of lipids, substrates of TE or precursor substances participating in the fatty acid biosynthesis, such as glycerol, acetic acid or malonic acid, may be added to the medium.

For example of the culture condition, in the case of using *Escherichia coli* as the host for transformation, culture may be carried out in LB medium or Overnight Express Instant TB Medium (manufactured by Novagen) at 30° C. to 37° C. for half a day to 1 day.

In the case of using *Arabidopsis thaliana* as the host for transformation, growth may be carried out at soil under the temperature conditions of 20° C. to 25° C., by continuously irradiating white light or under light illumination conditions of a light period of 16 hours and a dark period of 8 hours, for one to two months.

When the host of the transformant is the algae, the following culture media and culture conditions can be applied.

As the culture medium, medium based on natural seawater or artificial seawater may be used. Alternatively, commercially available culture medium may also be used. Specific examples of the culture medium include f/2 medium, ESM medium, Daigo IMK medium, L1 medium and MNK medium. Above all, from viewpoints of an improvement in the productivity of lipids and a nutritional ingredient concentration, f/2 medium, ESM medium or Daigo IMK medium is preferred; f/2 medium or Daigo IMK medium is more preferred; and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the algae to be seeded to the culture medium is not particularly limited. In view of viability, the amount is preferably 1% to 50% (vol/vol), and more preferably 1% to 10% (vol/vol), per culture medium. Culture temperature is not particularly limited within the range in which the temperature does not adversely affect growth of the algae, and is ordinarily in the range of 5° C. to 40° C. From viewpoints of the growth promotion of the algae, the improvement in productivity of fatty adds, and reduction of production cost, the temperature is preferably 10° C. to 35° C., and more preferably 15° C. to 30° C.

Moreover, the algae are preferably cultured under Irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light Irradiation is preferably in the range of 100 lx to 50,000 lx, more preferably in the range of 300 lx to 10,000 lx, and further preferably 1,000 lx to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion or the improvement in the productivity of fatty acids, the concentration is preferably from 0.03% (which is the same degree as the concentration under atmospheric conditions) to 10%, more preferably from 0.05% to 5%, further preferably from 0.1% to 3%, and furthermore preferably from 0.3% to 1%. A concentration of the carbonate is not particularly limited. When the sodium hydrogen carbonate is used, for example, from viewpoints of the growth promotion and the improvement in the productivity of fatty adds, the concentration is preferably from 0.01% to 5% by mass, more preferably from 0.05% to 2% by mass, and further preferably from 0.1% to 1% by mass.

A culture time is not particularly limited, and the culture may be performed for a long time (for example, about 150 days) so that an alga body in which the lipid is accumulated at a high concentration can grow at a high concentration. From viewpoints of the growth promotion of the algae, the improvement in the productivity of fatty acids, and the reduction of production cost, the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, shaking culture is preferred.

Lipids produced in the transformant is collected by an ordinary method used for isolating lipid components and the like contained in the living body of the transformant. For example, lipid components can be isolated and collected from the above-described cultured product or the transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from the cultured product or the transformant through pressing or extraction, and then performing general purification processes such as degumming, deacdification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

In the TE variant of the present invention, in comparison with the wild type TE, specificity to the acyl-ACP having the specific number of carbon atoms, for example, to C8 acyl-ACP, C10 acyl-ACP or C12 acyl-ACP is improved. As a result, in the transformant having the introduced variant, in comparison with the transformant having the Introduced wild type TE, the ratio of the content of fatty acids having the specific number of carbon atoms, such as C8 fatty acids, C10 fatty acids and C12 fatty acids each in the total fatty acid components increases. Therefore, the production method in which the transformant is used of the present invention can be preferably applied to production of the lipid having the specific number of carbon atoms, particularly C8 fatty acids, C10 fatty acids or C12 fatty acids, and a lipid containing these fatty acids as the components.

The lipids produced in the production method of the present invention are preferably fatty acids or lipids containing these fatty acids as the components, and more preferably contain fatty acids or esters thereof, in view of usability thereof. From usability for a surfactant or the like, the fatty acid or the ester thereof contained in the lipid is preferably a fatty acid of C8 to C16 or an ester thereof, more preferably a fatty acid of C12 to C14 or an ester thereof, further preferably a fatty acid of C12 or an ester thereof, and furthermore preferably lauric acid or an ester thereof.

From a viewpoint of utilizing the fatty acid as the surfactant, the content of the C12 fatty acid relative to total fatty acid content in total collected lipid components is preferably 3% by mass or more. Here, "total collected lipid components" means total lipid components calculated by the method applied in Examples.

The fatty acids and lipids obtained by the production method or the transformant of the present invention can be utilized for food, as well as an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing a lipid, transformants, methods of producing a transformant, proteins, genes, methods of modifying fatty acid composition, and methods of enhancing productivity of lipid described below.

<1> A method of producing a lipid, containing the steps of:
introducing a gene encoding any one of the following proteins (A) to (C) into a host, and thereby obtaining a transformant, and
culturing the transformant, to produce a lipid:
(A) A protein consisting of an amino acid sequence of the 128th to 287th positions set forth in SEQ ID NO: 1 in which at least one of the glycine of the 203rd position and the valine of the 204th position set forth in SEQ ID NO: 1 is substituted with tryptophan;
(B) A protein consisting of an amino acid sequence having 85% or more identity with the amino acid sequence of the 128th to 287th positions set forth in SEQ ID NO: 1, in which at least one of the amino acids corresponding to the 203rd position and the 204th position set forth in SEQ ID NO: 1 is substituted with tryptophan, and having acyl-ACP thioesterase activity; and
(C) A protein containing the amino acid sequence of the protein (A) or (B), and having acyl-ACP thioesterase activity.

<2> The method of producing a lipid described in the above item <1>, wherein the identity of the protein (B) with the amino acid sequence of the 128th to 287th positions set forth in SEQ ID NO: 1 is 86% or more, preferably 88% or more, and more preferably 90% or more.

<3> The method of producing a lipid described in the above item <1> or <2>, wherein the protein (B) consists of an amino acid sequence in which 1 or several amino acids, preferably 1 to 5 amino acids, more preferably 1 to 4 amino acids, further preferably 1 to 3 amino acids, furthermore preferably 1 or 2 amino acids, are deleted, substituted, inserted or added to the amino acid sequence of the 128th to 287th positions set forth in SEQ ID NO: 1, the 115th to 274th positions set forth in SEQ ID NO: 3, or the 126th to 285th positions set forth in SEQ ID NO: 49, and at least one of the amino acid corresponding to the 203rd position and the amino acid corresponding to the 204th position set forth in SEQ ID NO: 1 is substituted with tryptophan; and has an acyl-ACP thioesterase activity.

<4> The method of producing a lipid described in any one of the above items <1> to <3>, wherein the protein (B) is the following protein (Ba) or (Bb):
(Ba) A protein consisting of an amino acid sequence of the 115th to 274th positions set forth in SEQ ID NO: 3, in which at least one of the glycine of the 190th position and the valine of the 191st position set forth in SEQ ID NO: 3 is substituted with tryptophan, and having acyl-ACP thioesterase activity; or
(Bb) A protein consisting of an amino acid sequence of the 126th to 285th positions set forth in SEQ ID NO: 49, in which at least one of the glycine of the 201st position and the valine of the 202nd position set forth in SEQ ID NO: 49 is substituted with tryptophan, and having acyl-ACP thioesterase activity.

<5> The method of producing a lipid described in any one of the above items <1> to <4>, wherein the protein (C) is a protein consisting of an amino acid sequence in which, in an amino acid sequence set forth in SEQ ID NO: 1, 3 or 49, at least one of an amino acid at a position corresponding to the 203rd position and an amino acid at a position corresponding to the 204th position set forth in SEQ ID NO: 1 is substituted with tryptophan, and an amino acid on an N-terminal side is deleted at an arbitrary position of the 1st to 127th positions set forth in SEQ ID NO: 1, the 1st to 114th positions set forth in SEQ ID NO: 3, or the 1st to 125th positions set forth in SEQ ID NO: 49, respectively.

<6> The method of producing a lipid described in any one of the above items <1> to <5>, wherein the protein (C) consists of an amino acid sequence in which the amino acid sequence of the 1st to 127th positions set forth in SEQ ID NO: 1, the amino acid sequence of the 49th to 127th positions set forth in SEQ ID NO: 1, the amino acid sequence of the 58th to 127th positions set forth in SEQ ID NO: 1, the amino acid sequence of the 78th to 127th positions set forth in SEQ ID NO: 1, the amino acid sequence of the 87th to 127th positions set forth in SEQ ID NO: 1, the amino acid sequence of the 88th to 127th positions set forth in SEQ ID NO: 1, the amino acid sequence of the 98th to 127th positions set forth in SEQ ID NO: 1, the amino acid sequence of the 108th to 127th positions set forth in SEQ ID NO: 1, the amino acid sequence of the 118th to 127th positions set forth in SEQ ID NO: 1, or an amino acid sequence in which 1 or several amino acids, preferably 1 or more and 20 or less amino acids, more preferably 1 or more and 15 or less amino acids, further preferably 1 or more and 10 or less amino acids, furthermore preferably 1 or more and 5 or less amino acids, furthermore preferably 1 or more and 3 or less amino acids, are deleted, substituted, Inserted or added to any one of these amino acid sequences, is added to the N-terminal side of the amino acid sequence of the protein (A), and has the acyl-ACP thioesterase activity.

<7> The method of producing a lipid described in any one of the above items <1> to <5>, wherein the protein (C) consists of an amino acid sequence in which the amino acid sequence of the 36th to 114th positions set forth in SEQ ID NO: 3, the amino acid sequence of the 45th to 114th positions set forth in SEQ ID NO: 3, the amino acid sequence of the 55th to 114th positions set forth in SEQ ID NO: 3, the amino acid sequence of the 65th to 114th positions set forth in SEQ ID NO: 3, the amino acid sequence of the 75th to 114th positions set forth in SEQ ID NO: 3, the amino acid sequence of the 85th to 114th positions set forth in SEQ ID NO: 3, the amino acid sequence of the 95th to 114th positions set forth in SEQ ID NO: 3, the amino acid sequence of the 105th to 114th positions set forth in SEQ ID NO: 3, or an amino acid sequence in which 1 or several amino acids, preferably 1 or more and 20 or less amino acids, more preferably 1 or more and 15 or less amino acids, further preferably 1 or more and 10 or less amino acids, furthermore preferably 1 or more and 5 or less amino acids, furthermore preferably 1 or more and 3 or less amino acids, are deleted, substituted, inserted or added to any one of these amino acid sequences, is added to the N-terminal side of the amino acid sequence of the protein (Ba), and has the acyl-ACP thioesterase activity.

<8> The method of producing a lipid described in any one of the above items <1> to <5>, wherein the protein (C) consists of an amino acid sequence in which the amino acid sequence of the 1st to 125th positions set forth in SEQ ID NO: 49, the amino acid sequence of the 35th to 125th positions set forth in SEQ ID NO: 49, the amino acid sequence of the 55th to 125th positions set forth in SEQ ID NO: 49, the amino acid sequence of the 85th to 125th positions set forth in SEQ ID NO: 49, or an amino acid sequence in which 1 or several amino acids, preferably 1 or more and 20 or less amino acids, more preferably 1 or more and 15 or less amino acids, further preferably 1 or more and 10 or less amino acids, furthermore preferably 1 or more and 5 or less amino acids, furthermore preferably 1 or more and 3 or less amino acids, are deleted, substituted, inserted or added to any one of these amino acid sequences, is added to the N-terminal side of the amino acid sequence of the protein (Bb), and has the acyl-ACP thioesterase activity.

<9> The method of producing a lipid described in any one of the above items <1> to <8>, wherein, in the proteins (A) to (C), the glycine of the 203rd position set forth in SEQ ID NO: 1 or the amino acid corresponding to this position is substituted with tryptophan, and the valine of the 204th position set forth in SEQ ID NO: 1 or the amino acid corresponding to this position is substituted with tryptophan or phenylalanine, preferably tryptophan.

<10> The method of producing a lipid described in any one of the above items 10<1> to <9>, wherein at least one selected from the group consisting of the following amino acid substitutions (Ca) to (Cg) is further introduced into the amino acid sequence of any of the proteins (A) to (C):

(Ca) The leucine of the 143rd position set forth in SEQ ID NO: 1 or the amino acid corresponding to this position is substituted with proline;

(Cb) The histidine of the 146th position set forth in SEQ ID NO: 1 or the amino acid corresponding to this position is substituted with asparagine or serine;

(Cc) The glycine of the 160th position set forth in SEQ ID NO: 1 or the amino acid corresponding to this position is substituted with alanine;

(Cd) The methionine of the 202nd position set forth in SEQ ID NO: 1 or the amino acid corresponding to this position is substituted with phenylalanine, histidine, leucine, glutamine or valine;

(Ce) The glycine of the 212th position set forth in SEQ ID NO: 1 or the amino acid corresponding to this position is substituted with proline;

(Cf) The asparagine of the 213th position set forth in SEQ ID NO: 1 or the amino acid corresponding to this position is substituted with tyrosine; and (Cg) The proline of the 281st position set forth in SEQ ID NO: 1 or the amino acid corresponding to this position is substituted with glutamine.

<11> The method of producing a lipid described in the above item <10>, wherein the glycine of the 203rd position set forth in SEQ ID NO: 1 or the amino acid corresponding to this position, and the valine of the 204th position set forth in SEQ ID NO: 1 or the amino acid corresponding to this position are substituted with tryptophan in the amino acid sequence of any of the proteins (A) to (C), respectively; and one or two selected from the group consisting of the amino acid substitutions (Ca) to (Cg) are introduced into the amino acid sequence of any of the proteins (A) to (C).

<12> The method of producing a lipid described in the above item <10>, wherein the valine of the 204th position set forth in SEQ ID NO: 1 or the amino acid corresponding to this position is substituted with tryptophan in the amino acid sequence of any of the proteins (A) to (C); and one or two selected from the group consisting of the amino acid substitutions (Ca) to (Cg) are introduced into the amino acid sequence of any of the proteins (A) to (C).

<13> The method of producing a lipid described in any one of the above items <1> to <12>, wherein the amino acid sequence of any of the proteins (A) to (C) has one of the amino acid substitutions specified in the following items (1) to (14):

(1) The glycine of the 203rd position set forth in SEQ ID NO: 1 or the amino acid corresponding to this position is substituted with tryptophan;

(2) The valine of the 204th position set forth in SEQ ID NO: 1 or the amino acid corresponding to this position is substituted with tryptophan;

(3) The glycine of the 203rd position and the valine of the 204th position set forth in SEQ ID NO: 1 or the amino acids corresponding to these positions are substituted with tryptophan, respectively;

(4) The glycine of the 203rd position set forth in SEQ ID NO: 1 or the amino acid corresponding to this position is substituted with tryptophan, and the valine of the 204th position set forth in SEQ ID NO: 1 or the amino acid corresponding to this position is substituted with phenylalanine;

(5) The glycine of the 203rd position and the valine of the 204th position set forth in SEQ ID NO: 1 or the amino acids corresponding to these positions are substituted with tryptophan, respectively, and the leucine of the 143rd position set forth in SEQ ID NO: 1 or the amino acid corresponding to this position is substituted with proline;

(6) The glycine of the 203rd position and the valine of the 204th position set forth in SEQ ID NO: 1 or the amino acids corresponding to these positions are substituted with tryptophan, respectively, and the glycine of the 160th position set forth in SEQ ID NO: 1 or the amino acid corresponding to this position is substituted with alanine;

(7) The glycine of the 203rd position and the valine of the 204th position set forth in SEQ ID NO: 1 or the amino acids corresponding to these positions are substituted with tryptophan, respectively, and the glycine of the 212th position set forth in SEQ ID NO: 1 or the amino acid corresponding to this position is substituted with proline;

(8) The glycine of the 203rd position and the valine of the 204th position set forth in SEQ ID NO: 1 or the amino acids corresponding to these positions are substituted with tryptophan, respectively, and the asparagine of the 213th position set forth in SEQ ID NO: 1 or the amino acid corresponding to this position is substituted with tyrosine;

(9) The glycine of the 203rd position and the valine of the 204th position set forth in SEQ ID NO: 1 or the amino acids corresponding to these positions are substituted with tryptophan, respectively, the glycine of the 160th position set forth in SEQ ID NO: 1 or the amino acid corresponding to this position is substituted with alanine, and the asparagine of the 213th position set forth in SEQ ID NO: 1 or the amino acid corresponding to this position is substituted with tyrosine;

(10) The glycine of the 190th position and the valine of the 191st position set forth in SEQ ID NO: 3 or the amino acids corresponding to these positions are substituted with tryptophan, respectively;

(11) The valine of the 204th position set forth in SEQ ID NO: 1 or the amino acid corresponding to this position is substituted with tryptophan, and the histidine of the 146th position set forth in SEQ ID NO: 1 or the amino acid corresponding to this position is substituted with asparagine or serine;

(12) The valine of the 204th position set forth in SEQ ID NO: 1 or the amino acid corresponding to this position is substituted with tryptophan, and the methionine of the 202nd position set forth in SEQ ID NO: 1 or the amino add corresponding to this position is substituted with phenylalanine, histidine, leucine, glutamine or valine;

(13) The valine of the 204th position set forth in SEQ ID NO: 1 or the amino acid corresponding to this position is substituted with tryptophan, and the proline of the 281st position set forth in SEQ ID NO: 1 or the amino acid corresponding to this position is substituted with glutamine; and

(14) The valine of the 204th position set forth in SEQ ID NO: 1 or the amino acid corresponding to this position is substituted with tryptophan, the methionine of the 202nd position set forth in SEQ ID NO: 1 or the amino acid corresponding to this position is substituted with histidine, and the proline of the 281st position set forth in SEQ ID NO: 1 or the amino acid corresponding to this position is substituted with glutamine.

<14> The method of producing a lipid described in any one of the above items <1> to <13>, wherein the gene encoding any one of the proteins (A) to (C) is a gene consisting of any one of the following DNAs (A1) to (C1):

(A1) A DNA consisting of a nucleotide sequence of the 382nd to 864th positions set forth in SEQ ID NO: 2, in which at least one set of the nucleotides of the 607th to 609th positions and the nucleotides of the 610th to 612th positions set forth in SEQ ID NO: 2 is substituted with nucleotides encoding tryptophan;

(B1) A DNA consisting of a nucleotide sequence having 70% or more identity with the nucleotide sequence of the 382nd to 864th positions set forth in SEQ ID NO: 2, in which at least one set of the nucleotides corresponding to the 607th to 609th positions and the nucleotides corresponding to the 610th to 612th positions set forth in SEQ ID NO: 2 is substituted with nucleotides encoding tryptophan, and encoding a protein having acyl-ACP thioesterase activity; and (C1) A DNA containing the nucleotide sequence of the DNA (A1) or (B1), and encoding a protein having acyl-ACP thioesterase activity.

<15> The method of producing a lipid described in the above item <14>, wherein the identity of the DNA (B1) with the nucleotide sequence of the 382nd to 864th positions set forth in SEQ ID NO: 2 is 72% or more, preferably 74% or more, and more preferably 76% or more.

<16> The method of producing a lipid described in the above item <14> or <15>, wherein the DNA (B1) consists of a nucleotide sequence in which 1 or several nucleotides, preferably 1 to 20 nucleotides, more preferably 1 to 15 nucleotides, further preferably 1 to 10 nucleotides, furthermore preferably 1 to 5 nucleotides, furthermore preferably 1 to 3 nucleotides, are deleted, substituted, inserted or added to the nucleotide sequence of the 382nd to 864th positions set forth in SEQ ID NO: 2, the 343rd to 825th positions set forth in SEQ ID NO: 4, or the 376th to 858th positions set forth in SEQ ID NO: 50, and at least one set of the nucleotides corresponding to the 607th to 609th positions and the nucleotides corresponding to the 610th to 612th positions set forth in SEQ ID NO: 2 is substituted with nucleotides encoding tryptophan; and encodes a protein having the acyl-ACP thioesterase activity.

<17> The method of producing a lipid described in any one of the above items <14> to <16>, wherein the DNA (B1) is the following DNA (B1a) or (B1b).

(B1a) A DNA consisting of a nucleotide sequence of the 343rd to 825th positions set forth in SEQ ID NO: 4 in which at least one set of the nucleotides of the 568th to 570th positions and the nucleotides of the 571st to 573rd positions set forth in SEQ ID NO: 4 is substituted with nucleotides encoding tryptophan, and encoding a protein having acyl-ACP thioesterase activity; or (B1 b) A DNA consisting of a nucleotide sequence of the 376th to 858th positions set forth in SEQ ID NO: 50 in which at least one set of the nucleotides of the 601st to 603rd positions and the nucleotides of the 604th to 606th positions set forth in SEQ ID NO: 50 is substituted with nucleotides encoding tryptophan, and encoding a protein having acyl-ACP thioesterase activity.

<18> The method of producing a lipid described in any one of the above items <14> to <17>, wherein the DNA (C1) is a DNA consisting of a nucleotide sequence in which, in a nucleotide sequence set forth in SEQ NO: 2, 4 or 50, at least one set of the nucleotides corresponding to the 607th to 609th positions, and the nucleotides corresponding to the 610th to 612th positions set forth in SEQ ID NO: 2 is substituted with nucleotides encoding tryptophan, and nucleotides on a 5'-terminal side are deleted at an arbitrary position of the 1st to 381st positions set forth in SEQ ID NO: 2, the 1st to 342nd positions set forth in SEQ ID NO: 4, or the 1st to 375th positions set forth in SEQ ID NO: 50, respectively.

<19> The method of producing a lipid described in any one of the above items <14> to <18>, wherein the DNA (C1) consists of a nucleotide sequence in which the nucleotide sequence of the 1st to 381st positions set forth in SEQ ID NO: 2, the nucleotide sequence of the 145th to 381st positions set forth in SEQ ID NO: 2, the nucleotide sequence of the 172nd to 381st positions set forth in SEQ ID NO: 2, the nucleotide sequence of the 232nd to 381st positions set forth in SEQ ID NO: 2, the nucleotide sequence of the 259th to 381st positions set forth in SEQ ID NO: 2, the nucleotide sequence of the 262nd to 381st positions set forth in SEQ ID NO: 2, the nucleotide sequence of the 292nd to 381st positions set forth in SEQ ID NO: 2, the nucleotide sequence of the 322nd to 381st positions set forth in SEQ ID NO: 2, the nucleotide sequence of the 352nd to 381st positions set forth in SEQ ID NO: 2, or a nucleotide sequence in which 1 or several nucleotides, preferably 1 or more and 20 or less nucleotides, more preferably 1 or more and 15 or less nucleotides, further preferably 1 or more and 10 or less nucleotides, furthermore preferably 1 or more and 5 or less nucleotides, furthermore preferably 1 or more and 3 or less nucleotides, are deleted, substituted, Inserted or added to any one of these sequences, is added to the 5'-terminal side of the nucleotide sequence of the DNA (A1), and encodes a protein having the acyl-ACP thioesterase activity.

<20> The method of producing a lipid described in any one of the above items <14> to <18>, wherein the DNA (C1) consists of a nucleotide sequence in which the nucleotide sequence of the 106th to 342nd positions set forth in SEQ ID NO: 4, the nucleotide sequence of the 133rd to 342nd positions set forth in SEQ ID NO: 4, the nucleotide sequence of the 163rd to 342nd positions set forth in SEQ ID NO: 4, the nucleotide sequence of the 193rd to 342nd positions set forth in SEQ ID NO: 4, the nucleotide sequence of the 223rd to 342nd positions set forth in SEQ ID NO: 4, the nucleotide sequence of the 253rd to 342nd positions set forth in SEQ ID NO: 4, the nucleotide sequence of the 283rd to 342nd positions set forth in SEQ ID NO: 4, the nucleotide sequence of the 313th to 342nd positions set forth in SEQ ID NO: 4, or a nucleotide sequence in which 1 or several nucleotides, preferably 1 or more and 20 or less nucleotides, more preferably 1 or more and 15 or less nucleotides, further preferably 1 or more and 10 or less nucleotides, furthermore preferably 1 or more and 5 or less nucleotides, furthermore preferably 1 or more and 3 or less nucleotides, are deleted, substituted, Inserted or added to any one of these sequences, is added to the 5'-terminal side of the nucleotide sequence of the DNA (B1a), and encodes a protein having the acyl-ACP thioesterase activity.

<21> The method of producing a lipid described in any one of the above items <14> to <18>, wherein the DNA (C1) consists of a nucleotide sequence in which the nucleotide sequence of the 1st to 375th positions set forth in SEQ ID NO: 50, the nucleotide sequence of the 103rd to 375th positions set forth in SEQ ID NO: 50, the nucleotide sequence of the 163rd to 375th positions set forth in SEQ ID NO: 50, the nucleotide sequence of the 253rd to 375th positions set forth in SEQ ID NO: 50, or a nucleotide sequence in which 1 or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, furthermore preferably 1 or more and 3 or less nucleotides) are deleted, substituted, Inserted or added to any one of these sequences, is added to the 5'-terminal side of the nucleotide sequence of the DNA (Bib), and encodes a protein having the acyl-ACP thioesterase activity.

<22> The method of producing a lipid described in any one of the above items <14> to <21>, wherein, in the DNAs (A1) to (C1), the nucleotides of the 607th to 609th positions set forth in SEQ ID NO: 2 or the nucleotides corresponding to these positions are substituted with nucleotides encoding tryptophan, and the nucleotides of the 610th to 612th positions set forth in SEQ ID NO: 2 or the nucleotides corresponding to these positions are substituted with nucleotides encoding tryptophan or phenylalanine, preferably tryptophan.

<23> The method of producing a lipid described in any one of the above items <14> to <22>, wherein, into the DNAs (A1) to (C1), at least one selected from the group consisting of the following nucleotide substitutions (C1a) to (C1g) is further introduced:

(C1a) The nucleotides of the 427th to 429th positions set forth in SEQ ID NO: 2 or the nucleotides corresponding to these positions are substituted with nucleotides encoding proline;

(C1b) The nucleotides of the 436th to 438th positions set forth in SEQ ID NO: 2 or the nucleotides corresponding to these positions are substituted with nucleotides encoding asparagine or serine;

(C1c) The nucleotides of the 478th to 480th positions set forth in SEQ ID NO: 2 or the nucleotides corresponding to these positions are substituted with nucleotides encoding alanine;

(C1d) The nucleotides of the 604th to 606th positions set forth in SEQ ID NO: 2 or the nucleotides corresponding to these positions are substituted with nucleotides encoding phenylalanine, histidine, leucine, glutamine or valine;

(C1e) The nucleotides of the 634th to 636th positions set forth in SEQ ID NO: 2 or the nucleotides corresponding to these positions are substituted with nucleotides encoding proline; and (C1f) The nucleotides of the 637th to 639th positions set forth in SEQ ID NO: 2 or the nucleotides corresponding to these positions are substituted with nucleotides encoding tyrosine; and (C1g) The nucleotides of the 841st to 843rd positions set forth in SEQ ID NO: 2 or the nucleotides corresponding to these positions are substituted with nucleotides encoding glutamine.

<24> The method of producing a lipid described in the above item <23>, wherein the nucleotides of the 607th to 609th positions set forth in SEQ ID NO: 2 or the nucleotides corresponding to these positions, and the nucleotides of the 610th to 612th positions set forth in SEQ ID NO: 2 or the nucleotides corresponding to these positions are substituted with nucleotides encoding tryptophan in the nucleotide sequence of any of the DNAs (A1) to (C1), respectively; and one or two selected from the group consisting of the nucleotide substitutions (C1a) to (C1g) are introduced into the nucleotide sequence of any of the DNAs (A1) to (C1).

<25> The method of producing a lipid described in the above item <23>, wherein the nucleotides of the 610th to 612th positions set forth in SEQ ID NO: 2 or the nucleotides corresponding to these positions are substituted with nucleotides encoding tryptophan in the nucleotide sequence of any of the DNAs (A1) to (C1); and one or two selected from the group consisting of the nucleotide substitutions (C1a) to (C1g) are introduced into the nucleotide sequence of any of the DNAs (A1) to (C1).

<26> The method of producing a lipid described in any one of the above items <14> to <25>, wherein the nucleotide sequence of any of the DNAs (A1) to (C1) has one of the nucleotide substitutions specified in the following items (1-1) to (14-1):

(1-1) The nucleotides of the 607th to 609th positions set forth in SEQ ID NO: 2 or the nucleotides corresponding to these positions are substituted with nucleotides encoding tryptophan;

(2-1) The nucleotides of the 610th to 612th positions set forth in SEQ ID NO: 2 or the nucleotides corresponding to these positions are substituted with nucleotides encoding tryptophan;

(3-1) The nucleotides of the 607th to 609th positions and the nucleotides of the 610th to 612th positions set forth in SEQ ID NO: 2 or the nucleotides corresponding to these positions are substituted with nucleotides encoding tryptophan, respectively;

(4-1) The nucleotides of the 607th to 609th positions set forth in SEQ ID NO: 2 or the nucleotides corresponding to these positions are substituted with nucleotides encoding tryptophan, and the nucleotides of the 610th to 612th positions set forth in SEQ ID NO: 2 or the nucleotides corresponding to these positions are substituted with nucleotides encoding phenylalanine;

(5-1) The nucleotides of the 607th to 609th positions and the nucleotides of the 610th to 612th positions set forth in SEQ ID NO: 2 or the nucleotides corresponding to these positions are substituted with nucleotides encoding tryptophan, respectively, and the nucleotides of the 427th to 429th positions set forth in SEQ ID NO: 2 or the nucleotides corresponding to these positions are substituted with nucleotides encoding proline;

(6-1) The nucleotides of the 607th to 609th positions and the nucleotides of the 610th to 612th positions set forth in SEQ ID NO: 2 or the nucleotides corresponding to these positions are substituted with nucleotides encoding tryptophan, respectively, and the nucleotides of the 478th to 480th positions set forth in SEQ ID NO: 2 or the nucleotides corresponding to these positions are substituted with nucleotides encoding alanine;

(7-1) The nucleotides of the 607th to 609th positions and the nucleotides of the 610th to 612th positions set forth in SEQ ID NO: 2 or the nucleotides corresponding to these positions are substituted with nucleotides encoding tryptophan, respectively, and the nucleotides of the 634th to 636th positions set forth in SEQ ID NO: 2 or the nucleotides corresponding to these positions are substituted with nucleotides encoding proline;

(8-1) The nucleotides of the 607th to 609th positions and the nucleotides of the 610th to 612th positions set forth in SEQ ID NO: 2 or the nucleotides corresponding to these positions are substituted with nucleotides encoding tryptophan, respectively, and the nucleotides of the 637th to 639th positions set forth in SEQ ID NO: 2 or the nucleotides corresponding to these positions are substituted with nucleotides encoding tyrosine;

(9-1) The nucleotides of the 607th to 609th positions and the nucleotides of the 610th to 612th positions set forth in SEQ ID NO: 2 or the nucleotides corresponding to these positions are substituted with nucleotides encoding tryptophan, respectively, the nucleotides of the 478th to 480th positions set forth in SEQ ID NO: 2 or the nucleotides corresponding to these positions are substituted with nucleotides encoding alanine, and the nucleotides of the 637th to 639th positions set forth in SEQ ID NO: 2 or the nucleotides corresponding to these positions are substituted with nucleotides encoding tyrosine;

(10-1) The nucleotides of the 568th to 570th positions and the nucleotides of the 571st to 573rd positions set forth in SEQ ID NO: 4 or the nucleotides corresponding to these positions are substituted with nucleotides encoding tryptophan, respectively;

(11-1) The nucleotides of the 610th to 612th positions set forth in SEQ ID NO: 2 or the nucleotides corresponding to these positions are substituted with nucleotides encoding tryptophan, and the nucleotides of the 436th to 438th positions set forth in SEQ ID NO: 2 or the nucleotides corresponding to these positions are substituted with nucleotides encoding asparagine or serine;

(12-1) The nucleotides of the 610th to 612th positions set forth in SEQ ID NO: 2 or the nucleotides corresponding to these positions are substituted with nucleotides encoding tryptophan, and the nucleotides of the 604th to 606th positions set forth in SEQ ID NO: 2 or the nucleotides corresponding to these positions are substituted with nucleotides encoding phenylalanine, histidine, leucine, glutamine or valine;

(13-1) The nucleotides of the 610th to 612th positions set forth in SEQ ID NO: 2 or the nucleotides corresponding to these positions are substituted with nucleotides encoding tryptophan, and the nucleotides of the 841st to 843rd positions set forth in SEQ ID NO: 2 or the nucleotides corresponding to these positions are substituted with nucleotides encoding glutamine; and (14-1) The nucleotides of the 610th to 612th positions set forth in SEQ ID NO: 2 or the nucleotides corresponding to these positions are substituted with nucleotides encoding tryptophan, the nucleotides of the 604th to 606th positions set forth in SEQ ID NO: 2 or the nucleotides corresponding to these positions are substituted with nucleotides encoding histidine, and the nucleotides of the 841st to 843rd positions set forth in SEQ ID NO: 2 or the nucleotides corresponding to these positions are substituted with nucleotides encoding glutamine.

<27> The method of producing a lipid described in any one of the above items <1> to <26>, wherein the host is a microorganism.

<28> The method of producing a lipid described in the above item <27>, wherein the microorganism is a microalga, preferably an alga belonging to the genus *Nannochloropsis*.

<29> The method of producing a lipid described in the above item <27>, wherein the microorganism is *Escherichia coli*.

<30> The method of producing a lipid described in any one of the above items <1> to <29>, wherein the lipid contains a fatty acid having 8, 10 or 12 carbon atoms, or an ester thereof.

<31> The method of producing a lipid described in any one of the above items <1> to <30>, wherein the ratio of the content of the fatty acid having 8, 10 or 12 carbon atoms in the lipid increases in comparison with a lipid collected from a transformant having Introduced gene encoding a protein consisting of an amino acid sequence set forth in SEQ ID NO: 1.

<32> A protein specified in any one of the above items (A) to (C).

<33> The protein described in the above item <32>, which is any one of the proteins specified in the method of producing a lipid as described in any one of the above items <1> to <13>.

<34> A gene encoding the protein described in the above item <32> or <33>.

<35> A gene consisting of the DNA specified in any one of the above items (A1) to (C1).

<36> The gene described in the above item <34> or <35>, wherein the DNA is any one of the DNAs specified in the method of producing a lipid as described in any one of the above items <14> to <26>.

<37> A recombinant vector, containing the gene described in any one of the above items <34> to <36>.

<38> A transformant, which is obtained by introducing the gene described in any one of the above items <34> to <36> or the recombinant vector described in the above item <37> into a host.

<39> A method of producing a transformant, containing introducing the gene described in any one of the above items <34> to <36> or the recombinant vector described in the above item <37> into a host.

<40> The transformant or the method of producing the same described in the above item <38> or <39>, wherein the host is a microorganism.

<41> The transformant or the method of producing the same described in the above item <40>, wherein the microorganism is a microalga, preferably an alga belonging to the genus *Nannochloropsis*.

<42> The transformant or the method of producing the same described in the above item <40>, wherein the microorganism is *Escherichia coli*.

<43> Use of the transformant or a transformant obtained by the method of producing a transformant described in any of the above items <38> to <42>, for producing a lipid.

<44> The use described in the above item <43>, wherein the lipid contains a fatty acid having 8, 10 or 12 carbon atoms, or an ester thereof.

<45> A method of modifying a fatty acid composition in a lipid, containing introducing the gene described in any one of the above items <34> to <36> or the recombinant vector described in the above item <37> into a host, to modify the fatty acid composition in a lipid produced by the thus-obtained transformant.
<46> A method of enhancing productivity of a lipid, containing introducing the gene described in any one of the above items <34> to <36> or the recombinant vector described in the above item <37> into a host.
<47> The method described in the above item <45> or <46>, wherein the lipid contains a fatty acid having 8, 10 or 12 carbon atoms, or an ester thereof.
<48> A method of enhancing productivity of a fatty acid having 8, 10 or 12 carbon atoms, containing introducing the gene described in any one of the above items <34> to <36> or the recombinant vector described in the above item <37> into a host.

EXAMPLES

Hereinafter, the present invention will be described more in detail with reference to Examples, but the present invention is not limited thereto. Herein, the nucleotide sequences of the primers used in Examples are shown in Tables 1 to 4.

TABLE 1

| Primer No. | SEQ ID NO: | Nucleotide sequence of primer |
|---|---|---|
| 5 | SEQ ID NO: 5 | gcggccgctctagagtgcgagacggcccacgccgggac |
| 6 | SEQ ID NO: 6 | acaaaatattaacgcctagctaatatcaattttctttgg |
| 7 | SEQ ID NO: 7 | ctctagagcggccgccaccg |
| 8 | SEQ ID NO: 8 | gcgttaatattttgttaaaattcg |
| 9 | SEQ ID NO: 9 | ctggacaataccatgtgggttgccttttcgccgcc |
| 10 | SEQ ID NO: 10 | ctggacaataccatgggatgggccttttcgccgccaag |
| 11 | SEQ ID NO: 11 | ctggacaataccatgtggtgggccttttcgccgc |
| 12 | SEQ ID NO: 12 | ctggacaataccatgtggtttgccttttcgccgc |
| 13 | SEQ ID NO: 13 | catggtattgtccagcaaag |
| 14 | SEQ ID NO: 14 | gcctatcctgaattccctaagttccaccttatcca |
| 15 | SEQ ID NO: 15 | gaattcaggataggcccgatgcagcttgg |
| 16 | SEQ ID NO: 16 | ggcaaagagaaaattgatgcttacgaagtttacaa |
| 17 | SEQ ID NO: 17 | aattttctctttgcctcggagcgtctcg |
| 18 | SEQ ID NO: 18 | gccaagcgtggcaatccatttacagcaaatctcac |
| 19 | SEQ ID NO: 19 | cttggcggcgaaaaaggcaactc |
| 20 | SEQ ID NO: 20 | gccgccaagcgtggctacggttttacagcaaatct |
| 21 | SEQ ID NO: 21 | gccacgcttggcggcgaaaaaggc |
| 22 | SEQ ID NO: 22 | gcggccgctctagagcatgatcgcgtcgacaccaagc |
| 23 | SEQ ID NO: 23 | gcggccgctctagaggatgaagtaaagtctccgcag |
| 24 | SEQ ID NO: 24 | acaaaatattaacgcctaactgatgtccaccttcttc |
| 25 | SEQ ID NO: 25 | ctcgacaacactatgtggtgggcattcttcgctgc |
| 26 | SEQ ID NO: 26 | catagtgttgtcgagtaaggcggctatagag |

TABLE 2

| Primer No. | SEQ ID NO: | Nucleotide sequence of primer |
|---|---|---|
| 27 | SEQ ID NO: 27 | cgcggtgttgcgcgctgcgagacggcccacgccgggac |
| 28 | SEQ ID NO: 28 | ctcttccacagaagcctagctaatatcaattttctttgg |
| 32 | SEQ ID NO: 32 | cgagctcggtacccggcggtcttttgtcctttcctc |
| 33 | SEQ ID NO: 33 | aatctgctcggagggaggatc |
| 34 | SEQ ID NO: 34 | ccctccgagcagattatgaagaccgccgctctcctc |

TABLE 2-continued

| Primer No. | SEQ ID NO: | Nucleotide sequence of primer |
|---|---|---|
| 35 | SEQ ID NO: 35 | gcgcgcaacaccgcgggtgcgggagaac |
| 36 | SEQ ID NO: 36 | gcttctgtggaagagccagtg |
| 37 | SEQ ID NO: 37 | actctagaggatcccctgatcttgtccatctcgtg |
| 38 | SEQ ID NO: 38 | gggatcctctagagtcgacc |
| 39 | SEQ ID NO: 39 | cgggtaccgagctcgaattc |
| 42 | SEQ ID NO: 42 | cttttttgtgaagcaatggccaagttgaccagtgccg |
| 43 | SEQ ID NO: 43 | ctcttccacagaagcttagtcctgctcctcggccacg |
| 44 | SEQ ID NO: 44 | cgagctcggtacccgactgcgcatggattgaccga |
| 45 | SEQ ID NO: 45 | tgcttcacaaaaaagacagcttcttgat |
| 46 | SEQ ID NO: 46 | ggcggtcttttgtcctttcctc |
| 47 | SEQ ID NO: 47 | ctgatcttgtccatctcgtg |
| 48 | SEQ ID NO: 48 | actgcgcatggattgaccga |

TABLE 3

| Primer No. | SEQ ID NO: | Nucleotide sequence of primer |
|---|---|---|
| 51 | SEQ ID NO: 51 | gaacttcaggaattcaggatagg |
| 52 | SEQ ID NO: 52 | gaattcctgaagttcaaccttatccacgagacgct |
| 53 | SEQ ID NO: 53 | gaattcctgaagttctcacttatccacgagacgct |
| 54 | SEQ ID NO: 54 | ggtattgtccagcaaagccgcaatg |
| 55 | SEQ ID NO: 55 | ttgctggacaataccttcggatgggccttttcgc |
| 56 | SEQ ID NO: 56 | ttgctggacaatacccatggatgggccttttcgc |
| 57 | SEQ ID NO: 57 | ttgctggacaatacccctaggatgggccttttcgc |
| 58 | SEQ ID NO: 58 | Ttgctggacaatacccaaggatgggccttttcgc |
| 59 | SEQ ID NO: 59 | Ttgctggacaataccgtaggatgggccttttcgc |
| 60 | SEQ ID NO: 60 | Gcccttcaataaaggactttgag |
| 61 | SEQ ID NO: 61 | Cctttattgaagggccagaagaaaattgatattag |
| 62 | SEQ ID NO: 62 | Ggcaagaaaagctgggggaaaagacagg |
| 63 | SEQ ID NO: 63 | ccagcttttcttgccactgcgcatggattgaccga |

TABLE 4

| Primer No. | SEQ ID NO: | Nucleotide sequence of primer |
|---|---|---|
| 64 | SEQ ID NO: 64 | gcggccgctctagagatgacgcctttggccttcac |
| 65 | SEQ ID NO: 65 | gcggccgctctagagcttagaaccagcttcccagtc |
| 66 | SEQ ID NO: 66 | gcggccgctctagaggctgccatttccctgccgtcg |
| 67 | SEQ ID NO: 67 | gcggccgctctagagagacgaggtgagaggaaggc |
| 68 | SEQ ID NO: 68 | gcggccgctctagaggatggtggaaaaggcgaggcc |
| 69 | SEQ ID NO: 69 | gcggccgctctagaggctacatgcaatccatccttattc |

Examples 1 Producing Lipid by *Escherichia coli* Having Introduced Gene Encoding NoTE Variant (1) Preparation of NoTE Gene, and Construction of Plasmid for NoTE Expression Total RNA of *Nannochloropsis oculata* strain NIES2145 (obtained from National institute for Environmental Studies (NIES)) was extracted. The cDNA was obtained by reverse transcription using the total RNA, and SuperScript (trademark) III First-Strand Synthesis SuperMix for qRT-PCR (manufactured by invitrogen). PCR using a pair of the primer Nos. 5 and 6 shown in Table 1 and the above cDNA as a template, was carried out to prepare a gene fragment consisting of the nucleotide sequence of the 262nd to 864th positions set forth in SEQ ID NO: 2. Moreover, using a plasmid vector pBluescriptII SK(−) (manufactured by Stratagene) as a template, and a pair of the primer Nos. 7 and 8 shown in Table 1, the pBluescriptII SK(−) was amplified by PCR. Then, the resultant template was subjected to digestion by restriction enzyme DDnI (manufactured by TOYOBO) treatment. These two fragments were purified using a High Pure PCR Product Purification Kit (manufactured by Roche Applied Science), and then fused using an In-Fusion HD Cloning Kit (manufactured by Clontech) to construct a plasmid NoTE_262 for NoTE expression. This plasmid NoTE_262 was constructed in the form of removing amino acid residues of the 1st to 87th positions on an N-terminal side of the amino acid sequence set forth in SEQ ID NO: 1, and fusing, to the upstream of the removed terminus, amino acid residues of the 1st to 29th positions on an N-terminal side of a LacZ protein derived from the plasmid vector pBluescriptII SK(−).

In the following plasmid notation, "NoTE_262" means that a plasmid had the nucleotide sequence of the 262nd to 864th positions set forth in SEQ ID NO: 2 as a nucleotide sequence encoding a polypeptide consisting of the amino acid sequence of the 88th to 287th positions set forth in SEQ ID NO: 1.

(2) Construction of Plasmid for NoTE Variant Expression

PCR was carried out by using the plasmid NoTE_262 as a template, and a pair of any one of the primer Nos. 9 to 12 and the primer No. 13 shown in Table 1, to obtain gene fragments in which a part of nucleotides of the 262nd to 864th positions of the nucleotide sequence set forth in SEQ ID NO: 2 was subjected to mutation, respectively. Various plasmids for NoTE variant expression (NoTE_262 (G203W), NoTE_262(V204W), NoTE_262(G203W+ V204W) and NoTE_262(G203W+V204F)) were constructed by using these gene fragments according to a technique in a manner similar to the above-described manner, respectively. With respect to these plasmids, the codon(s) at the following sites was modified relative to the nucleotide sequence set forth in SEQ ID NO: 2.

(i) NoTE_262(G203W): A codon encoding the glycine of the 203rd position of the amino acid sequence set forth in SEQ ID NO: 1 was substituted with a codon encoding tryptophan (TGG).

(ii) NoTE_262(V204W): A codon encoding the valine of the 204th position of the amino acid sequence set forth in SEQ ID NO: 1 was substituted with a codon encoding tryptophan (TGG).

(Iii) NoTE_262(G203W+V204W): A codon encoding the glycine of the 203rd position of the amino acid sequence set forth in SEQ ID NO: 1 was substituted with a codon encoding tryptophan (TGG), and a codon encoding the valine of the 204th position of the amino acid sequence set forth in SEQ ID NO: 1 was substituted with a codon encoding tryptophan (TGG), respectively.

(iv) NoTE_262(G203W+V204F): A codon encoding the glycine of the 203rd position of the amino acid sequence set forth in SEQ ID NO: 1 was substituted with a codon encoding tryptophan (TGG), and a codon encoding the valine of the 204th position of the amino acid sequence set forth in SEQ ID NO: 1 was substituted with a codon encoding phenylalanine (TTT), respectively.

Subsequently, PCR was carried out by using the plasmid NoTE_262(G203W+V204W) as a template, and a pair of the primer Nos. 14 and 15, a pair of the primer Nos. 16 and 17, a pair of the primer Nos. 18 and 19, and a pair of the primer Nos. 20 and 21 shown in Table 1, respectively, to obtain gene fragments in which a part of nucleotides of the 262nd to 864th positions of the nucleotide sequence set forth in SEQ ID NO: 2 was subjected to mutation, respectively. Various plasmids for NoTE variant expression (NoTE_262 (WW+L143P), NoTE_262(WW+G160A), NoTE_262 (WW+G212P) and NoTE_262(WW+N213Y)) were constructed by using these gene fragments according to a technique in a manner similar to the above-described manner, respectively. With respect to these plasmids, the codons at the following sites were modified relative to the nucleotide sequence set forth in SEQ ID NO: 2.

(v) NoTE_262(WW+L143P): A codon encoding the glycine of the 203rd position of the amino acid sequence set forth in SEQ ID NO: 1 was substituted with a codon encoding tryptophan (TGG), a codon encoding the valine of the 204th position of the amino acid sequence set forth in SEQ ID NO: 1 was substituted with a codon encoding tryptophan (TGG), and a codon encoding the leucine (L) of the 143rd position of the amino acid sequence set forth in SEQ ID NO: 1 was substituted with a codon encoding proline (CCT), respectively.

(vi) NoTE_262(WW+G160A): A codon encoding the glycine of the 203rd position of the amino acid sequence set forth in SEQ ID NO: 1 was substituted with a codon encoding tryptophan (TGG), a codon encoding the valine of the 204th position of the amino acid sequence set forth in SEQ ID NO: 1 was substituted with a codon encoding tryptophan (TGG), and a codon encoding the glycine of the 160th position of the amino acid sequence set forth in SEQ ID NO: 1 was substituted with a codon encoding alanine (GCT), respectively.

(vii) NoTE_262(WW+G212P): A codon encoding the glycine of the 203rd position of the amino acid sequence set forth in SEQ ID NO: 1 was substituted with a codon encoding tryptophan (TGG), a codon encoding the valine of the 204th position of the amino acid sequence set forth in SEQ ID NO: 1 was substituted with a codon encoding tryptophan (TGG), and a codon encoding the glycine of the 212th position of the amino acid sequence set forth in SEQ ID NO: 1 was substituted with a codon encoding proline (CCA), respectively.

(viii) NoTE_262(WW+N213Y): A codon encoding the glycine of the 203rd position of the amino acid sequence set forth in SEQ ID NO: 1 was substituted with a codon encoding tryptophan (TGG), a codon encoding the valine of the 204th position of the amino acid sequence set forth in SEQ ID NO: 1 was substituted with a codon encoding tryptophan (TGG), and a codon encoding the asparagine of the 213th position of the amino acid sequence set forth in SEQ ID NO: 1 was substituted with a codon encoding tyrosine (TAC), respectively.

Further, PCR was carried out by using the plasmid NoTE_262(WW+N213Y) as a template, and a pair of the primer Nos. 16 and 17 shown in Table 1 to obtain a gene fragment in which a part of nucleotides of the 262nd to 864th positions of the nucleotide sequence set forth in SEQ ID NO: 2 was subjected to mutation. A plasmid for NoTE variant expression (NoTE_262(WW+G160A+N213Y)) was constructed by using this gene fragment according to a technique in a manner similar to the above-described manner.

(ix) NoTE_262(WW+G160A+N213Y): A codon encoding the glycine of the 203rd position of the amino acid sequence set forth in SEQ ID NO: 1 was substituted with a codon encoding tryptophan (TGG), a codon encoding the valine of the 204th position of the amino acid sequence set forth in SEQ ID NO: 1 was substituted with a codon encoding tryptophan (TGG), a codon encoding the glycine of the 160th position of the amino acid sequence set forth in SEQ ID NO: 1 was substituted with a codon encoding alanine (GCT), and a codon encoding the asparagine of the 213rd position of the amino acid sequence set forth in SEQ ID NO: 1 was substituted with a codon encoding tyrosine (Y) (TAC), respectively.

(3) Introduction of Plasmid for Expression into *Escherichia coli*, Extraction of Lipid from *Escherichia coli* Culture Fluid and Analysis of Fatty Acids Contained Therein An *Escherichia coli* mutant strain (strain K27 (fadD88), See Overath et al, Eur. J. Biochem., 1969, vol. 7, 559-574), was transformed by a competent cell transformation method, using the various plasmids for NoTE variant expression. Each of the thus-obtained transformants was stand overnight at 30° C., and a colony thus obtained was inoculated in 1 mL of LBAmp liquid medium (Bacto Trypton 1%, Yeast Extract 0.5%, NaCl 1%, and Ampicillin sodium 50 μg/mL), and then cultured overnight at 30° C. The culture fluid of 2 μL was inoculated to 2 mL of Overnight Express Instant TB Medium (Novagen) and was subjected to shaking culture at 30° C. After 24 hours cultivation, lipid components contained in the culture fluid were analyzed by the method described below. In addition, as a negative control, the *Escherichia coli* strain K27 transformed with the plasmid vector pBluescriptII SK(−), and the *Escherichia coli* strain K27 transformed with the plasmid for expression of the wild type NoTE (NoTE_262) described above, were also subjected to the same experiment.

<Method of Analyzing Lipid Components>

To 1 mL of the culture fluid, 50 CL of 1 mg/mL 7-pentadecanone as an internal standard was added, and then 0.5 mL of chloroform, 1 mL of methanol and 10 &L of 2N hydrochloric acid were further added. The mixture was vigorously stirred and then was left for 30 minutes. Further, 0.5 mL of chloroform and 0.5 mL of 1.5% KCl were added thereto. The mixture was stirred and centrifuged for 15 minutes at 3,000 rpm, and then the chloroform layer (lower layer) was collected with pasteur pipette.

A nitrogen gas was blown onto the resultant chloroform layer to be dried into solid, 0.7 mL of 0.5 N potassium hydroxide/methanol solution was added thereto, and the resultant mixture was kept warm at 80° C. for 30 minutes. Then, 1 mL of 14% solution of boron trifluoride (manufactured by Sigma-Aldrich) was added to the sample, and the mixture was kept warm at 80° C. for 10 minutes. Thereafter, 1 mL of saturated saline and 1 mL of hexane were added thereto, and the mixture was vigorously stirred and then was left for 30 minutes at room temperature. Then, the hexane layer (upper layer) was collected to obtain fatty acid esters.

Under the measuring conditions as follows, the obtained fatty acid esters were provided for gas chromatographic analysis.

<Gas Chromatography Conditions>
Capillary column: DB-1 MS (30 m×200 μm×0.25 μm, manufactured by J&W Scientific)
Mobile phase: high purity helium
Flow rate Inside the column: 1.0 mL/min
Temperature rise program: 100° C. (for 1 min.)→10° C./min→300° C. (for 5 min.)
Equilibration time: for 1 min.
Injection port split Injection (split ratio: 100:1)
Pressure: 14.49 psi, 104 mL/min
Amount of injection: 1 μL
Cleaning vial: methanol/chloroform
Detector temperature: 300° C.

The fatty acid esters were identified by providing the identical sample for a gas chromatography-mass spectrometry analysis under identical conditions described above.

Amounts of the fatty acid methyl esters were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples, and then the amount of each of the fatty acids per liter of the culture fluid was calculated. Further, the total amount of the fatty acids was calculated by summing the amounts of each of the fatty acids thus obtained, and ratio of amounts of each of the fatty acids in the total amount of the fatty acids was calculated.

The results are shown in Table 5. Herein, in Tables below, "TFA" presents a total amount of fatty acids, and "Fatty Acid Composition (% TFA)" presents a ratio of amount of each fatty acid relative to a weight of the total fatty acid. Moreover, the expressions "C17:0Δ" and "C19:0Δ" designate cis-9,10-Methylen-hexadecanoic acid and cis-11,12-Methylen-octadecanoic acid, respectively. Further, the description "C12:n" represents a total of fatty acids having compositions of C12:1 and C12:0, and "C12:n (% TFA)" presents a ratio of amount of the C12:n relative to a weight of the total fatty acid.

TABLE 5

| Plasmid | TFA (mg/L) | Fatty acid composition (% TFA) | | | | | | | | | | | (n = 3) C12:n (% TFA) |
| --- | --- | --- | --- | --- | --- | --- | --- | --- | --- | --- | --- | --- | --- |
| | | C10:0 | C12:1 | C12:0 | C14:1 | C14:0 | C16:1 | C16:0 | C17:0Δ | C18:1 | C19:0Δ | | |
| pBS | 214.7 ± 26.1 | 0.0 ± 0.0 | 0.0 ± 0.0 | 0.8 ± 0.0 | 0.0 ± 0.0 | 6.0 ± 0.1 | 0.0 ± 0.0 | 47.8 ± 0.2 | 29.0 ± 0.2 | 3.7 ± 0.3 | 12.7 ± 0.1 | | 0.8 ± 0.0 |
| NoTE_262 | 581.5 ± 21.7 | 0.9 ± 0.0 | 7.1 ± 0.3 | 4.5 ± 0.1 | 20.0 ± 0.2 | 12.9 ± 0.1 | 21.6 ± 0.2 | 18.3 ± 0.1 | 7.5 ± 0.4 | 4.9 ± 0.1 | 2.3 ± 0.0 | | 11.6 ± 0.4 |
| (i) NoTE_262 (G203W) | 845.3 ± 39.6 | 1.5 ± 0.1 | 7.8 ± 0.4 | 10.5 ± 0.4 | 10.3 ± 0.2 | 22.7 ± 0.4 | 16.5 ± 0.1 | 17.9 ± 0.6 | 5.9 ± 0.2 | 4.4 ± 0.2 | 2.5 ± 0.1 | | 18.3 ± 0.7 |
| (ii) NoTE_262 (V204W) | 398.8 ± 26.3 | 1.3 ± 0.1 | 12.9 ± 0.2 | 7.0 ± 0.2 | 20.2 ± 0.2 | 12.8 ± 0.2 | 15.2 ± 0.1 | 16.2 ± 0.3 | 7.9 ± 0.1 | 4.7 ± 0.2 | 1.8 ± 0.1 | | 19.9 ± 0.3 |

TABLE 5-continued

| Plasmid | TFA (mg/L) | Fatty acid composition (% TFA) | | | | | | | | | | (n = 3) C12:n (% TFA) |
|---|---|---|---|---|---|---|---|---|---|---|---|---|
| | | C10:0 | C12:1 | C12:0 | C14:1 | C14:0 | C16:1 | C16:0 | C17:0Δ | C18:1 | C19:0Δ | |
| (iii) NoTE_262 (G203W + V204W) | 1254.7 ± 18.9 | 2.3 ± 0.1 | 10.6 ± 0.1 | 10.0 ± 0.1 | 13.1 ± 0.1 | 22.9 ± 0.1 | 21.5 ± 0.1 | 11.7 ± 0.1 | 3.3 ± 0.0 | 3.8 ± 0.0 | 0.8 ± 0.0 | 20.6 ± 0.2 |
| (iv) NoTE_262 (G203W + V204F) | 1248.1 ± 45.5 | 2.0 ± 0.3 | 13.0 ± 0.5 | 8.9 ± 0.2 | 16.4 ± 0.4 | 23.0 ± 0.4 | 21.1 ± 0.6 | 9.5 ± 0.3 | 2.9 ± 0.1 | 2.6 ± 0.1 | 0.7 ± 0.0 | 21.9 ± 0.6 |
| (v) NoTE_262 (WW + L143P) | 708.1 ± 18.4 | 5.5 ± 0.1 | 13.8 ± 0.2 | 7.8 ± 0.2 | 10.0 ± 0.0 | 19.1 ± 0.1 | 12.4 ± 0.2 | 18.4 ± 0.2 | 5.5 ± 0.1 | 5.2 ± 0.1 | 2.2 ± 0.0 | 21.6 ± 0.4 |
| (vi) NoTE_262 (WW + G160A) | 1122.4 ± 18.1 | 3.0 ± 0.1 | 13.7 ± 0.3 | 10.8 ± 0.2 | 14.8 ± 0.1 | 20.4 ± 0.2 | 21.2 ± 0.4 | 9.2 ± 0.2 | 3.1 ± 0.1 | 3.3 ± 0.1 | 0.6 ± 0.0 | 24.5 ± 0.6 |
| (vii) NoTE_262 (WW + G212P) | 1210.2 ± 34.9 | 2.5 ± 0.1 | 12.2 ± 0.5 | 13.2 ± 0.2 | 13.0 ± 0.2 | 23.2 ± 0.3 | 16.8 ± 0.2 | 9.7 ± 0.3 | 3.2 ± 0.0 | 5.0 ± 0.2 | 1.0 ± 0.0 | 25.5 ± 0.6 |
| (viii) NoTE_262 (WW + N213Y) | 839.7 ± 6.4 | 5.7 ± 0.1 | 10.7 ± 0.2 | 14.6 ± 0.1 | 8.0 ± 0.1 | 19.2 ± 0.3 | 13.9 ± 0.1 | 14.4 ± 0.2 | 4.9 ± 0.1 | 6.4 ± 0.0 | 2.2 ± 0.1 | 25.3 ± 0.3 |
| (ix) NoTE_262 (WW + G160A + N213Y) | 746.4 ± 20.3 | 8.7 ± 0.1 | 13.7 ± 0.3 | 14.1 ± 0.2 | 8.1 ± 0.2 | 13.7 ± 0.1 | 13.3 ± 0.1 | 14.4 ± 0.6 | 5.8 ± 0.2 | 7.0 ± 0.1 | 1.3 ± 0.0 | 27.8 ± 0.6 |

(Mean ± Standard Deviation)

As shown in Table 5, in comparison with the transformant having the introduced plasmid NoTE_262, a ratio of C10 fatty acid and C12 fatty acids (C12:n) each in the total amount of fatty acids significantly increased in the transformants having the introduced NoTE variants constructed in such a manner that at least one of amino acids of the 203rd position and the 204th position of the amino acid sequence set forth in SEQ ID NO: 1 was substituted with tryptophan.

Moreover, in comparison with the transformants having the introduced NoTE_262(G203W) or NoTE_262(V204W), the ratio of the content of C10 fatty acids and C12 fatty adds each in the total amount of fatty acids further increased in the transformants having the introduced plasmid NoTE_262 (G203W+V204W) constructed in such a manner that both amino acids of the 203rd position and the 204th position of the amino acid sequence set forth in SEQ ID NO: 1 were substituted with tryptophan, and plasmid NoTE_262 (G203W+V204F) constructed in such a manner that the amino acids of the 203rd position and the 204th position of the amino acid sequence set forth in SEQ ID NO: 1 were substituted with tryptophan and phenylalanine, respectively.

Further, in comparison with the transformant having the introduced NoTE_262(G203W+V204W), the ratio of the content of C10 fatty acid and C12 fatty acids each in the total amount of fatty acids further increased in the transformants having the introduced NoTE_262(WW+L143P), NoTE_262 (WW+G160A), NoTE_262(WW+G212P) or NoTE_262 (WW+N213Y) which were constructed in such a manner that other amino acids at specific positions, in addition to the amino acids of the 203rd position and the 204th position of the amino acid sequence set forth in SEQ ID NO: 1, were substituted with a specific amino acid. In particular, in comparison with the transformant strains having the introduced NoTE_262(WW+G160A) or NoTE_262(WW+ N213Y), the ratio of the content of C10 fatty acid and C12 fatty acids each in the total amount of fatty acids still further increased in the transformant having the introduced NoTE_262(WW+G160A+N213Y).

Example 2 Production of Lipid by *Escherichia coli* Having Introduced Gene Encoding NoTE Variant from which N-Terminal of Amino Acid Sequence Set Forth in SEQ ID NO: 1 was Deleted (1) Construction of Plasmid for NoTE Variant Expression PCR was carried out by using the plasmids NoTE_262 and NoTE_262(G203W+V204W) prepared in Example 1 as a template, respectively, and a pair of the primer Nos. 22 and 8 shown in Table 1 to obtain gene fragments consisting of a nucleotide sequence of the 382nd to 864th positions of the nucleotide sequence set forth in SEQ ID NO: 2 and gene fragments in which a part of nucleotides of the 382nd to 864th positions of the nucleotide sequence set forth in SEQ ID NO: 2 was subjected to mutation, respectively. A plasmid for NoTE expression (NoTE_382) and a plasmid for NoTE variant expression (NoTE_382(G203W+V204W)) were constructed by using these gene fragments according to a technique in a manner similar to Example1, respectively.

In the following plasmid notation, "NoTE_382" means that a plasmid had the nucleotide sequence of the 382nd to 864th positions set forth in SEQ ID NO: 2 as a nucleotide sequence encoding a polypeptide consisting of the amino acid sequence of the 128th to 287th positions set forth in SEQ ID NO: 1.

Moreover, with respect to the plasmid NoTE_382 (G203W+V204W), the codons at the following sites were modified relative to the nucleotide sequence set forth in SEQ ID NO: 2.

(x) NoTE_382(G203W+V204W): A codon encoding the glycine of the 203rd position of the amino acid sequence set forth in SEQ ID NO: 1 was substituted with a codon encoding tryptophan (TGG), and a codon encoding the valine of the 204th position of the amino acid sequence set forth in SEQ ID NO: 1 was substituted with a codon encoding tryptophan (TGG), respectively.

(2) Introduction of Plasmid for Expression into *Escherichia coli*, Extraction of Lipid from *Escherichia coli* Culture Fluid and Analysis of Fatty Acids Contained Therein The plasmid NoTE_382(G203W+V204W) was introduced into *Escherichia coli*, and the resultant strain was cultured to analyze a lipid component contained in the culture fluid according to a method similar to Example 1. Further, as a negative control, the plasmid NoTE_382 was also subjected to the same experiment. The results are shown in Table 6.

TABLE 6

| Plasmid | TFA (mg/L) | Fatty acid composition (% TFA) | | | | | | | | | | C12:n (% TFA) |
|---|---|---|---|---|---|---|---|---|---|---|---|---|
| | | C10:0 | C12:1 | C12:0 | C14:1 | C14:0 | C16:1 | C16:0 | C17:0Δ | C18:1 | C19:0Δ | |
| NoTE_382 | 236.3 | 0.6 | 1.7 | 2.0 | 7.5 | 7.7 | 15.3 | 34.2 | 14.3 | 12.3 | 4.3 | 3.7 |
| (x) NoTE_382 (G203W + V204W) | 996.2 | 2.6 | 9.1 | 10.5 | 11.5 | 22.0 | 19.0 | 14.8 | 4.0 | 5.2 | 1.2 | 19.6 |

As shown in Table 6, also when the 127 residues on the N-terminal of the NoTE were deleted in the amino acid sequence, in comparison with the transformant having the introduced plasmid for wild type NoTE_382 expression, the ratio of C10 fatty acid and C12 fatty acids (C12:n) each in the total amount of fatty acids significantly increased in the transformant having the introduced NoTE_382(G203W+V204W) constructed in such a manner that the amino acids of the 203rd position and the 204th position of the amino acid sequence set forth in SEQ ID NO: 1 were substituted with tryptophan.

Example 3 Producing Lipid by *Escherichia coli* Having Introduced Gene Encoding NgTE Variant (1) Preparation of NgTE Gene, and Construction of Plasmid for NgTE Expression A gene encoding an acyl-ACP thioesterase derived from *Nannochloropsis gaditana* consisting of an amino acid sequence set forth in SEQ ID NO: 3 (NgTE gene, SEQ ID NO: 4) was obtained by using a custom artificial gene synthesis service.

Using the NgTE gene as a template, and a pair of the primer Nos. 23 and 24 as shown in Table 1, a gene fragment consisting of the nucleotide sequence of 253rd to 825th positions set forth in SEQ ID NO: 4 was prepared by PCR. The obtained gene fragment was fused with the pBluescriptII SK(-) vector in a manner similar to the method in Example 1 to construct a plasmid NgTE_253 for wild type NgTE expression. This plasmid NgTE_253 was constructed in the form of removing amino acid residues of the 1st to 84th positions on an N-terminal side of the amino acid sequence set forth in SEQ ID NO: 3, and fusing, to the upstream of the removed terminus, amino acid residues of the 1st to 29th positions on an N-terminal side of a LacZ protein derived from the plasmid vector pBluescriptII SK(-).

In the following plasmid notation, "NgTE_253" means that a plasmid had the nucleotide sequence of the 253rd to 825th positions set forth in SEQ ID NO: 4 as a nucleotide sequence encoding a polypeptide consisting of the amino acid sequence of the 85th to 274th positions set forth in SEQ ID NO: 3.

(2) Construction of Plasmid for NgTE Variant Expression

PCR was carried out by using the plasmid NgTE_253 as a template, and a pair of the primer Nos. 25 and 26 shown in Table 1, to obtain a gene fragment in which a part of nucleotides of the 253rd to 825th positions of the nucleotide sequence set forth in SEQ ID NO: 4 was subjected to mutation. A plasmid for NgTE variant expression (NgTE_253(G190W+V191W)) was constructed by using the obtained gene fragment according to a technique in a manner similar to Example 1.

With respect to the plasmid NgTE_253(G190W+V191W), the codons at the following sites were modified relative to the nucleotide sequence set forth in SEQ ID NO: 4.

(xi) NgTE_253(G190W+V191W): A codon encoding the glycine of the 190th position of the amino acid sequence set forth in SEQ ID NO: 3 was substituted with a codon encoding tryptophan (TGG), and a codon encoding the valine of the 191st position of the amino acid sequence set forth in SEQ ID NO: 3 was substituted with a codon encoding tryptophan (TGG), respectively.

(3) Introduction of Plasmid for Expression into *Escherichia coli*, Extraction of Lipid from *Escherichia coli* Culture Fluid and Analysis of Fatty Acids Contained Therein The plasmid NgTE_253(G190W+V191W) was introduced into *Escherichia coli*, and the resultant strain was cultured to analyze a lipid component contained in the culture fluid according to a method similar to Example 1. Moreover, as a negative control, the plasmid NoTE_253 was also subjected to the same experiment The results are shown in Table 7.

TABLE 7

| Plasmid | TFA (mg/L) | Fatty acid composition (% TFA) | | | | | | | | | | C12:n (% TFA) |
|---|---|---|---|---|---|---|---|---|---|---|---|---|
| | | C12:1 | C12:0 | C14:1 | C14:0 | C16:1 | C16:0 | C17:0Δ | C18:1 | C19:0Δ | | |
| NgTE_253 | 377.4 | 3.1 | 2.8 | 10.4 | 11.1 | 17.2 | 32.7 | 11.1 | 8.8 | 2.8 | | 5.9 |
| (xi) NgTE_253 (G190W + V191W) | 672.4 | 6.1 | 9.8 | 9.6 | 25.0 | 16.4 | 18.4 | 6.0 | 6.4 | 2.2 | | 16.0 |

As shown in Table 7, in comparison with the transformant having the introduced plasmid for wild type NgTE_253 expression, the ratio of C12 fatty acids (C12:n) in the total amount of fatty acids significantly increased in the transformant having the introduced NgTE_253(G190W+V191W) which was constructed in such a manner that amino acids of the 190th position and the 191st position of the amino acid sequence set forth in SEQ NO: 3 were substituted with tryptophan, respectively.

Example 4 Producing Lipid by *Nannochloropsis oculata* Having Introduced Gene Encoding NoTE Variant (1) Construction of Plasmid for NoTE Variant Expression PCR was carried out by using the plasmids NoTE_262, NoTE_262(G203W+V204F) or NoTE_262(G203W+V204W) prepared in Example 1 as a template, and a pair of the primer Nos. 27 and 28 shown in Table 2, to obtain a gene fragment consisting of the nucleotide sequence of the 262nd to 864th positions of the nucleotide sequence set forth in SEQ ID NO: 2 and a gene fragment in which a part of nucleotides of the 262nd to 864th positions of the nucleotide sequence set forth in SEQ ID NO: 2 was subjected to mutation, respectively.

A VCP1 promoter sequence (SEQ ID NO: 29), a VCP1 chloroplast transit signal sequence (SEQ ID NO: 30) and a VCP1 terminator sequence (SEQ ID NO: 31) were artificially synthesized based on the complete cds sequence (Accession number: JF957601.1) of the VCP1 (violaxanthin/(chlorophyll a)-binding protein) gene of *Nannochloropsis* sp. strain W2J3B registered in GenBank. Using each of the thus-synthesized DNA fragments as a template, and a pair of the primer Nos. 32 and 33, a pair of the primer Nos. 34 and 35, and a pair of the primer Nos. 36 and 37 as shown in Table 2, PCR was carried out to prepare the VCP1 promoter sequence, the VCP1 chloroplast transit signal sequence and the VCP1 terminator sequence, respectively. Moreover, using a plasmid vector pUC19 (manufactured by TAKARA BIO) as a template, and a pair of the primer Nos. 38 and 39 shown in Table 2, PCR was carried out to amplify the plasmid vector pUC19.

The NoTE gene fragment, the VCP1 promoter sequence, the VCP1 chloroplast transit signal sequence and the VCP1 terminator sequence obtained as described above were fused with the plasmid vector pUC19 in a manner similar to the method in Example 1, to construct a plasmid NoTE_262_Nanno for NoTE expression, and a plasmid NoTE_262(G203W+V204F)_Nanno and a plasmid NoTE_262(G203W+V204W)_Nanno for NoTE variants expression, respectively. Herein, these plasmids consisted of the pUC19 vector sequence and a sequence for NoTE gene expression in which the VCP1 promoter sequence, the VCP1 chloroplast transit signal sequence, the NoTE gene fragment (wild type or modified) and the VCP1 terminator sequence were linked in this order.

As the nucleotide sequence encoding the polypeptide consisting of the amino acid sequence of the 88th to 287th positions set forth in SEQ ID NO: 1, the plasmid had the nucleotide sequence of the 262nd to 864th positions set forth in SEQ ID NO: 2.

Moreover, with respect to the plasmids for NoTE variant expression, the codons at the following sites were modified relative to the nucleotide sequence set forth in SEQ ID NO: 2.

(xii) NoTE_262(G203W+V204F) Nanno: A codon encoding the glycine of the 203rd position of the amino acid sequence set forth in SEQ ID NO: 1 was substituted with a codon encoding tryptophan (TGG), and a codon encoding the valine of the 204th position of the amino acid sequence set forth in SEQ ID NO: 1 was substituted with a codon encoding phenylalanine (TTT), respectively.

(xii) NoTE_262(G203W+V204W)_Nanno: A codon encoding the glycine of the 203rd position of the amino acid sequence set forth in SEQ ID NO: 1 was substituted with a codon encoding tryptophan (TGG), and a codon encoding the valine of the 204th position of the amino acid sequence set forth in SEQ ID NO: 1 is substituted with a codon encoding tryptophan (TGG), respectively.

(2) Construction of Plasmid for Zeocin Resistance Gene Expression in *Nannochloropsis*

A zeocin resistance gene (SEQ ID NO: 40), and a tubulin promoter sequence (SEQ ID NO: 41) derived from *Nannochloropsis gaditana* strain CCMP 526 described in a literature (Randor Radakovits, et al., Nature Communications, DOI:10.1038/ncomms1688, 2012) were artificially synthesized.

Using the thus-synthesized DNA fragments as a template, and a pair of the primer Nos. 42 and 43, and a pair of the primer Nos. 44 and 45 shown in Table 2, PCR was carried out, to prepare the zeocin resistance gene and the tubulin promoter sequence, respectively. These amplified fragments were fused with the VCP1 terminator sequence and the amplified fragment of the plasmid vector pUC19 prepared in a manner similar to the method in Example 1, to construct a plasmid for zeocin resistance gene expression. Herein, the plasmid for gene expression consisted of the pUC19 vector sequence and a sequence for zeocin resistance gene expression in which the tubulin promoter sequence, the zeocin resistance gene and the VCP1 terminator sequence were linked in this order.

(3) Introduction of Plasmids for NoTEs Expression and Plasmid for Zeocin Resistance Gene Expression into *Nannochloropsis*

Using the plasmids NoTE_262_Nanno, NoTE_262 (G203W+V204F)_Nanno, and NoTE_262(G203W+V204W)_Nanno for expression as a template, and a pair of the primer Nos. 46 and 47 shown in Table 2, PCR was carried out, to amplify sequences for NoTE genes expression in the plasmids.

Moreover, using the plasmid for zeocin resistance gene expression as a template, and a pair of the primer Nos. 48 and 47 shown in Table 2, PCR was carried out to amplify a sequence for zeocin resistance gene expression.

The amplified DNA fragments were purified using High Pure PCR Product Purification Kit (manufactured by Roche Applied Science). Herein, sterilized water was used for elution upon purification without using an elution buffer included in the kit.

About $1 \times 10^9$ cells of *Nannochloropsis oculata* strain NIES2145 (obtained from National Institute for Environmental Studies (NIES)) were washed with 384 mM sorbitol solution to completely remove a salt, and the resultant was used as a host cell of transformation. The DNA fragment for NoTE gene expression (wild type or modified) and DNA fragment for zeocin resistance gene expression as amplified above were mixed by about 500 ng for each with the host cell, and electroporation was carried out under conditions of 50 μF, 500Ω and 2,200 v/2 mm.

After 24 hours recovery cultivation in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCs_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), the resultant material was Inoculated in f/2 agar medium containing 2 μg/mL of zeocin, and cultured for two to three weeks under 12 h/12 h light-dark conditions at 25° C. under an atmosphere of 0.3% $CO_2$. A transformant containing the fragment for NoTE gene expression was selected from the resultant colonies by a PCR method. The selected strain was inoculated to 20 mL of medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare preculture fluid. Then, 2 mL of the preculture fluid was inoculated to 18 mL of the N15P5 medium, and subjected to shaking culture for two weeks under the 12 h/12 h light-dark conditions at 25° C. under the atmosphere of 0.3% $CO_2$. In addition, as a negative control, an experiment was also conducted on the wild type strain, *Nannochloropsis oculata* strain NIES2145.

(4) Extraction of Lipid from *Nannochloropsis* Culture Fluid and Analysis of Fatty Acids Contained Therein After the cultivation, the analysis of lipid components contained in the culture fluid was carried out in a manner similar to the method in Example 1. Table 8 shows the results. Herein, in Table 8 below, "n" designates an integer of 0 to 5. For example, when "C18:n" is described, the description means a total of each fatty acid having compositions of C18:0, C18:1, C18:2, C18:3, C18:4 and C18:5.

TABLE 8

| Plasmid | Fatty acid composition (% TFA) | | | | | |
|---|---|---|---|---|---|---|
| | C12:0 | C14:0 | C16:1 | C16:0 | C18:n | C20:n |
| Wild type strain | 0.00 | 3.9 | 29.9 | 37.2 | 17.7 | 11.3 |
| NoTE_262_Nanno | 1.32 | 6.0 | 34.3 | 23.9 | 21.2 | 13.4 |
| (xii) NoTE_262 (G203W + V204F)_Nanno | 3.33 | 8.6 | 35.5 | 20.9 | 19.2 | 12.5 |
| (xiii) NoTE_262 (G203W + V204W)_Nanno | 4.62 | 10.1 | 36.7 | 16.8 | 18.4 | 13.4 |

As shown in Table 8, in comparison with the transformant having the introduced plasmid for NoTE_262 expression, ratios of C12:0 fatty acid and C14:0 fatty acid each in the total amount of fatty acids significantly increased in the transformants having the introduced NoTE_262(G203W+V204F)_Nanno or NoTE_262(G203W+V204W)_Nanno which were constructed in such a manner that at least one of amino acids of the 203rd position and the 204th position of the amino acid sequence set forth in SEQ NO: 1 was substituted with tryptophan.

Example 5 Producing Lipid by *Escherichia coli* Having Introduced Gene Encoding NoTE Variant (1) Construction of Plasmid for NoTE Multiple Variant Expression PCR was carried out by using the plasmid NoTE_262 (V204W) prepared in Example 1 as a template, and a pair of the primer Nos. 51 and 52, a pair of the primer Nos. 51 and 53, a pair of the primer Nos. 54 and 55, a pair of the primer Nos. 54 and 56, a pair of the primer Nos. 54 and 57, a pair of the primer Nos. 54 and 58, a pair of the primer Nos. 54 and 59, and a pair of the primer Nos. 60 and 61 shown in Table 3, respectively, to obtain gene fragments in which a part of nucleotides of the 262nd to 864th positions of the nucleotide sequence set forth in SEQ ID NO: 2 was subjected to mutation, respectively. Various plasmids for NoTE variant expression (NoTE_262(V204W+H146N), NoTE_262(V204W+H146S), NoTE_262(V204W+M202F), NoTE_262(V204W+M202H), NoTE_262(V204W+M202L), NoTE_262(V204W+M202Q), NoTE_262(V204W+M202V) and NoTE_262(V204W+P281Q)) were constructed by using these gene fragments according to a technique in a manner similar to the above-described manner, respectively. With respect to these plasmids, the codons at the following sites were modified relative to the nucleotide sequence set forth in SEQ ID NO: 2.

(xiv) NoTE_262(V204W+H146N): A codon encoding the valine of the 204th position of the amino acid sequence set forth in SEQ ID NO: 1 was substituted with a codon encoding tryptophan (TGG), and a codon encoding the histidine of the 146th position of the amino acid sequence set forth in SEQ ID NO: 1 was substituted with a codon encoding asparagine (AAC), respectively.

(xv) NoTE_262(V204W+H146S): A codon encoding the valine of the 204th position of the amino acid sequence set forth in SEQ ID NO: 1 was substituted with a codon encoding tryptophan (TGG), and a codon encoding the histidine of the 146th position of the amino acid sequence set forth in SEQ ID NO: 1 was substituted with a codon encoding serine (TCA), respectively.

(xvi) NoTE_262(V204W+M202F): A codon encoding the valine of the 204th position of the amino acid sequence set forth in SEQ ID NO: 1 was substituted with a codon encoding tryptophan (TGG), and a codon encoding the methionine of the 202nd position of the amino acid sequence set forth in SEQ ID NO: 1 was substituted with a codon encoding phenylalanine (F) (TTC), respectively.

(xvii) NoTE_262(V204W+M202H): A codon encoding the valine of the 204th position of the amino acid sequence set forth in SEQ ID NO: 1 was substituted with a codon encoding tryptophan (TGG), and a codon encoding the methionine of the 202nd position of the amino acid sequence set forth in SEQ ID NO: 1 was substituted with a codon encoding histidine (CAT), respectively.

(xviii) NoTE 262(V204W+M202L): A codon encoding the valine of the 204th position of the amino acid sequence set forth in SEQ ID NO: 1 was substituted with a codon encoding tryptophan (TGG), and a codon encoding the methionine of the 202nd position of the amino acid sequence set forth in SEQ ID NO: 1 was substituted with a codon encoding leucine (CTA), respectively.

(xix) NoTE_262(V204W+M202Q): A codon encoding the valine of the 204th position of the amino acid sequence set forth in SEQ ID NO: 1 was substituted with a codon encoding tryptophan (TGG), and a codon encoding the methionine of the 202nd position of the amino acid sequence set forth in SEQ ID NO: 1 was substituted with a codon encoding glutamine (CAA), respectively.

(xx) NoTE_262(V204W+M202V): A codon encoding the valine of the 204th position of the amino acid sequence set forth in SEQ ID NO: 1 was substituted with a codon encoding tryptophan (TGG), and a codon encoding the methionine of the 202nd position of the amino acid sequence set forth in SEQ ID NO: 1 was substituted with a codon encoding valine (GTA), respectively.

(xxi) NoTE_262(V204W+P281Q): A codon encoding the valine of the 204th position of the amino acid sequence set forth in SEQ ID NO: 1 was substituted with a codon encoding tryptophan (TGG), and a codon encoding the proline of the 281st position of the amino acid sequence set forth in SEQ ID NO: 1 was substituted with a codon encoding glutamine (CAG), respectively.

Subsequently, PCR was carried out by using the plasmid NoTE_262(V204W+P281Q) as a template, and a pair of the primer Nos. 54 and 56 shown in Table 3, to obtain a gene fragment in which a part of nucleotides of the 262nd to 864th positions of the nucleotide sequence set forth in SEQ ID NO: 2 was subjected to mutation. A plasmid for NoTE variant expression (NoTE_262(V204W+M202H+P281Q)) was constructed by using this gene fragment according to a technique in a manner similar to the above-described manner. With respect to this plasmid, the codons at the following sites were modified relative to the nucleotide sequence set forth in SEQ ID NO: 2.

(xxii) NoTE_262(V204W+M202H+P281Q): A codon encoding the valine of the 204th position of the amino acid sequence set forth in SEQ ID NO: 1 was substituted with a codon encoding tryptophan (TGG), a codon encoding the methionine of the 202nd position of the amino acid sequence set forth in SEQ ID NO: 1 was substituted with a codon encoding histidine (CAT), and a codon encoding the proline of the 281st position of the amino acid sequence set forth in SEQ ID NO: 1 was substituted with a codon encoding glutamine (CAG), respectively.

(2) Introduction of Plasmid for Expression into *Escherichia coli*, Extraction of Lipid from *Escherichia coli* Culture Fluid and Analysis of Fatty Acids Contained Therein Each of the plasmids for gene expression was introduced into *Escherichia coli*, and the resultant strain was cultured, to analyze lipid components contained in the culture fluid according to a method similar to Example 1. Moreover, as comparisons, the plasmid for NoTE_262 expression and the plasmid for NoTE_262(V204W) expression were also subjected to the same experiment. The results are shown in Table 9.

the amino acid sequence set forth in SEQ NO: 1 was substituted, production of C8 fatty acid which was almost unable to be confirmed in the transformants having the introduced NoTE_262 or NoTE_262(V204W), was confirmed.

Further, in the transformants having the introduced plasmids constructed in such a manner that the valine of the 204th position of the amino acid sequence set forth in SEQ NO: 1 was substituted with tryptophan, and the methionine of the 202nd position thereof or the proline of the 281st position thereof was substituted with other amino acid, the ratio of the content of C12 fatty acids each in the total amount of fatty acids further increased, in comparison with the transformant having the introduced NoTE_262 (V204W).

Example 6 Producing Lipid by *Nannochloropsis oculata* Having Introduced Gene Encoding NoTE Variant (1) Construction of Plasmid for NoTE Variant Expression PCR was carried out by using the plasmids NoTE_262, NoTE_262(G203W), NoTE_262(V204W) or NoTE_262 (G203W+V204W) prepared in Example 1 as a template, and a pair of the primer Nos. 27 and 28 shown in Table 2, to obtain gene fragments consisting of the nucleotide sequence of the 262nd to 864th positions of the nucleotide sequence set forth in SEQ ID NO: 2 and gene fragments in which a part of nucleotides of the 262nd to 864th positions of the nucleotide sequence set forth in SEQ ID NO: 2 was subjected to mutation, respectively.

PCR was carried out using the pUC19 vector containing the VCP1 promoter sequence, the VCP1 chloroplast transit

TABLE 9

| Plasmid | TFA (mg/L) | Fatty acid composition (% TFA) | | | | | | | | | | | C12:n (% TFA) |
|---|---|---|---|---|---|---|---|---|---|---|---|---|---|
| | | C8:0 | C10:0 | C12:1 | C12:0 | C14:1 | C14:0 | C16:1 | C16:0 | C17:0Δ | C18:1 | C19:0Δ | |
| NoTE_262 | 581.5 | 0.0 | 0.9 | 7.1 | 4.5 | 20.0 | 12.9 | 21.6 | 18.3 | 7.5 | 4.9 | 2.3 | 11.6 |
| (ii) NoTE_262 (V204W) | 282.5 | 0.0 | 1.0 | 14.9 | 7.7 | 23.4 | 15.3 | 15.7 | 13.4 | 6.0 | 1.8 | 0.8 | 22.7 |
| (xiv) NoTE_262 (V204W + H146N) | 270.6 | 3.4 | 3.4 | 10.4 | 6.5 | 17.4 | 15.8 | 22.1 | 13.5 | 5.4 | 1.4 | 0.7 | 16.8 |
| (xv) NoTE_262 (V204W + H146S) | 530.7 | 1.7 | 2.6 | 7.4 | 10.6 | 14.4 | 17.6 | 13.2 | 19.7 | 6.6 | 4.5 | 1.6 | 18.0 |
| (xvi) NoTE_262 (V204W + M202F) | 392.0 | 0.0 | 1.6 | 14.0 | 10.9 | 18.8 | 11.8 | 8.7 | 20.9 | 4.1 | 7.9 | 1.4 | 24.8 |
| (xvii) NoTE_262 (V204W + M202H) | 612.7 | 0.0 | 0.3 | 12.4 | 8.1 | 24.8 | 14.6 | 12.4 | 17.5 | 2.6 | 6.5 | 0.9 | 20.5 |
| (xviii) NoTE_262 (V204W + M202L) | 274.5 | 0.0 | 1.5 | 16.7 | 8.0 | 22.8 | 11.5 | 13.0 | 15.0 | 4.2 | 6.2 | 1.0 | 24.8 |
| (xix) NoTE_262 (V204W + M202Q) | 372.7 | 0.0 | 1.2 | 16.0 | 8.1 | 24.6 | 13.2 | 13.8 | 14.4 | 2.6 | 5.5 | 0.7 | 24.0 |
| (xx) NoTE_262 (V204W + M202V) | 363.2 | 0.0 | 1.1 | 16.8 | 8.6 | 24.2 | 11.4 | 12.6 | 15.5 | 2.9 | 6.2 | 0.8 | 25.4 |
| (xxi) NoTE_262 (V204W + P281Q) | 230.2 | 0.0 | 2.5 | 16.4 | 10.6 | 21.3 | 16.0 | 11.5 | 13.1 | 4.7 | 2.7 | 1.2 | 27.0 |
| (xxii) NoTE_262 (V204W + M202H + P281Q) | 615.8 | 0.0 | 1.7 | 21.4 | 12.2 | 23.0 | 13.0 | 8.1 | 12.1 | 3.1 | 4.6 | 0.8 | 33.6 |

As shown in Table 9, in comparison with the transformant having the introduced plasmid NoTE_262, the ratio of C12 fatty acids in the total amount of fatty acids significantly increased in any of the variants.

Moreover, in the transformants having the introduced plasmid NoTE_262(V204W+H146N) or plasmid NoTE_262(V204W+H146S), which were constructed in such a manner that the amino acid of the 146th position of signal sequence and the VCP1 terminator sequence constructed in Example 4 as a template, and a pair of the primer No. 32 shown in Table 2 and the primer No. 62 shown in Table 3, to amplify cassettes for NoTE expression (fragment containing the VCP1 promoter sequence, the VCP1 chloroplast transit signal sequence, the wild type or modified NoTE sequence, and the VCP1 terminator sequence).

Subsequently, PCR was carried out using the plasmid for zeocin resistance gene expression constructed in Example 4 as a template, and a pair of the primer No. 39 shown in Table 2 and the primer No. 63 shown in Table 3, to amplify a fragment containing the cassette for zeocin resistance gene expression (the tubulin promoter sequence, the zeocin resistance gene, and the VCP1 terminator sequence) and the pUC19 sequence.

(3) Extraction of Lipid from *Nannochloropsis* Culture Fluid and Analysis of Fatty Acids Contained Therein Selection and culture of a transformant, and the analysis of lipid components contained in the culture fluid were carried out in a manner similar to the method in Example 4. In addition, the hexane amount to be used upon extracting the lipid was adjusted to 0.5 mL. The results are shown in Table 10.

TABLE 10

| Plasmid | Fatty acid composition (% TFA) | | | | | | |
|---|---|---|---|---|---|---|---|
| | C10:0 | C12:0 | C14:0 | C16:1 | C16:0 | C18:n | C20:n |
| NoTE_262_Nanno(zeo) | 0.37 | 1.38 | 5.2 | 38.6 | 19.9 | 22.9 | 11.7 |
| (xxiii) NoTE_262 (G203W)_Nanno(zeo) | 0.75 | 2.72 | 7.3 | 35.7 | 23.2 | 18.3 | 12.0 |
| (xxiv) NoTE_262 (V204W)_Nanno(zeo) | 1.57 | 5.80 | 10.7 | 30.1 | 17.5 | 20.8 | 13.6 |
| (xxv) NoTE_262 (G203W + V204W)_Nanno(zeo) | 2.19 | 5.33 | 9.9 | 37.5 | 12.6 | 20.5 | 12.0 |

The cassette for NoTE expression, and the fragments consisting of the cassette for zeocin resistance gene expression and the pUC19 sequence were fused by a method in a manner similar to Example 1, to construct plasmids for drug resistance linking type NoTE expression (NoTE_262_Nanno(zeo), NoTE_262(G203W)_Nanno (zeo), NoTE_262(V204W)_Nanno(zeo) and NoTE_262 (G203W+V204W)_Nanno(zeo)) in which the cassette for NoTE expression and the cassette for zeocin resistance gene expression were linked, respectively. With respect to the plasmids for NoTE expression, the codons at the following sites were modified relative to the nucleotide sequence set forth in SEQ ID NO: 2.

(xxiii) NoTE_262(G203W)_Nanno(zeo): A codon encoding the glycine of the 203rd position of the amino acid sequence set forth in SEQ ID NO: 1 was substituted with a codon encoding tryptophan (TGG).

(xxiv) NoTE_262(V204W)_Nanno(zeo): A codon encoding the valine of the 204th position of the amino acid sequence set forth in SEQ ID NO: 1 was substituted with a codon encoding tryptophan (TGG).

(xxv) NoTE_262(G203W+V204W)_Nanno(zeo): A codon encoding the glycine of the 203rd position of the amino acid sequence set forth in SEQ ID NO: 1 was substituted with a codon encoding tryptophan (TGG), and a codon encoding the valine of the 204th position of the amino acid sequence set forth in SEQ ID NO: 1 was substituted with a codon encoding tryptophan (TGG), respectively.

(2) Introduction of Plasmids for NoTE Expression into *Nannochloropsis*, Culture of Transformant, Extraction of Lipid from Culture Fluid and Analysis of Fatty Acids Contained Therein PCR was carried out using the expression plasmid NoTE_262_Nanno(zeo), NoTE_262(G203W)_Nanno(zeo), NoTE_262(V204W)_Nanno(zeo) or NoTE_262(G203W+V204W)_Nanno(zeo) as a template, and a pair of the primer Nos. 46 and 47 shown in Table 2, to amplify a fragment in which the cassette for NoTE gene expression and the cassette for zeocin resistance gene expression were linked, respectively.

Obtained DNA fragments were purified, and introduced into *Nannochloropsis oculata* strain NIES2145 by an electroporation method in a manner similar to the method in Example 4, respectively.

As shown in Table 10, in comparison with the transformant having the Introduced NoTE_262, the ratio of the content of C10 fatty acid, C12 fatty acid and C14 fatty acid each in the total amount of fatty acids significantly Increased in the transformants having the introduced NoTE_262 (G203W)_Nanno(zeo) which was constructed in such a manner that the glycine of the 203rd position of the amino acid sequence set forth in SEQ NO: 1 was substituted with tryptophan; NoTE_262(V203W)_Nanno(zeo) which was constructed in such a manner that the valine of the 204th position of the amino acid sequence set forth in SEQ NO: 1 was substituted with tryptophan; and NoTE_262(G203W+V204W)_Nanno(zeo) which was constructed in such a manner that the amino acids of the 203rd position and the 204th position of the amino acid sequence set forth in SEQ NO: 1 were substituted with tryptophan, respectively.

Example 7 Producing Lipid by *Escherichia coli* Having Introduced Gene Encoding NoTE Variant in which N-Terminal Length was Modified (1) Construction of Plasmid for NoTE Variant Expression in which N-Terminal Length was Modified PCR was carried out by using the cDNA of *Nannochloropsis oculata* strain NIES2145 prepared in Example 1 as a template, and a pair of any one of the primer Nos. 64 to 69 shown in Table 4 and primer No. 22 shown in Table 1, and the primer No. 6 shown in Table 1, to obtain a gene fragment consisting of the nucleotide sequence of the 1st to 864th positions of the nucleotide sequence set forth in SEQ ID NO: 2, a gene fragment consisting of the nucleotide sequence of the 172nd to 864th positions of the nucleotide sequence set forth in SEQ ID NO: 2, a gene fragment consisting of the nucleotide sequence of the 232nd to 864th positions of the nucleotide sequence set forth in SEQ ID NO: 2, a gene fragment consisting of the nucleotide sequence of the 292nd to 864th positions of the nucleotide sequence set forth in SEQ ID NO: 2, a gene fragment consisting of the nucleotide sequence of the 322nd to 864th positions of the nucleotide sequence set forth in SEQ ID NO: 2, a gene fragment consisting of the nucleotide sequence of the 352nd to 864th positions of the nucleotide sequence set forth in SEQ ID NO: 2, and a gene fragment consisting of the nucleotide sequence of the 382nd to 864th positions of the nucleotide sequence set forth in SEQ ID NO: 2, respectively. Plasmids for NoTE expression in which N-terminal length was modified NoTE_1, NoTE_172, NoTE_232, NoTE_292, NoTE_322, NoTE_352 and NoTE_382 were constructed by using these gene fragments according to a technique in a manner similar to Example 1, respectively.

In the following plasmid notation, "NoTE_1", "NoTE_172", "NoTE_232", "NoTE_292", "NoTE_322", "NoTE_352" and "NoTE_382" mean that a plasmid had the nucleotide sequence of the 1st to 864th positions, the 172nd to 864th positions, the 232nd to 864th positions, the 292nd to 864th positions, the 322nd to 864th positions, the 352nd to 864th positions and the 382nd to 864th positions set forth in SEQ ID NO: 2 as a nucleotide sequence encoding a polypeptide consisting of the amino acid sequence of the 1st to 287th positions, the 57th to 287th positions, the 77th to 287th positions, the 97th to 287th positions, the 107th to 287th positions, the 117th to 287th positions, and the 127th to 287th positions set forth in SEQ ID NO: 1, respectively.

PCR was carried out by using these plasmids as a template, and a pair of the primer Nos. 10 and 13 shown in Table 1, to obtain gene fragments in which a part of nucleotides of the 1st to 864th positions, the 172nd to 864th positions, the 232nd to 864th positions, the 292nd to 864th positions, the 322nd to 864th positions, the 352nd to 864th positions, and the 382nd to 864th positions of the nucleotide sequence set forth in SEQ ID NO: 2 was subjected to mutation, respectively. Plasmids for NoTE variant expression in which N-terminal length was modified NoTE_1(V204W), NoTE_172(V204W), NoTE_232(V204W), NoTE_292 (V204W), NoTE_322(V204W), NoTE_352(V204W) and NoTE_382(V204W) were constructed by using these gene fragments according to a technique in a manner similar to Example 1, respectively.

With respect to any of these plasmids (xxvi) NoTE_1 (V204W), (xxvii) NoTE_172(V204W), (xxviii) NoTE_232 (V204W), (xxix) NoTE_292(V204W), (xxx) NoTE_322 (V204W), (xxxi) NoTE_352(V204W) and (xxxii) NoTE_382(V204W), the codons at the following sites were modified relative to the nucleotide sequence set forth in SEQ ID NO: 2.

(xxvi) to (xxxii): A codon encoding the valine of the 204th position of the amino acid sequence set forth in SEQ ID NO: 1 was substituted with a codon encoding tryptophan (TGG).

(2) Introduction of Plasmid for Expression into *Escherichia coli*, Extraction of Lipid from *Escherichia coli* Culture Fluid and Analysis of Fatty Acids Contained Therein The plasmids NoTE_1(V204W), NoTE_172(V204W), NoTE_232(V204W), NoTE_292(V204W), NoTE_322 (V204W), NoTE_352(V204W) and NoTE_382(V204W) were Introduced into *Escherichia coli* respectively, and the resultant strain was cultured to analyze a lipid component contained in the culture fluid according to a method similar to Example 1. Moreover, as a negative control, the plasmids NoTE_1, NoTE_172, NoTE_232, NoTE_292, NoTE_322, NoTE_352 and NoTE_382 were also subjected to the same experiment, respectively. The results are shown in Table 11.

TABLE 11

| Plasmid | TFA (mg/L) | Fatty acid composition (% TFA) | | | | | | | | | | C12:n (% TFA) |
|---|---|---|---|---|---|---|---|---|---|---|---|---|
| | | C10:0 | C12:1 | C12:0 | C14:1 | C14:0 | C16:1 | C16:0 | C17:0Δ | C18:1 | C19:0Δ | |
| NoTE_1 | 348.8 | 0.0 | 1.3 | 2.2 | 6.9 | 10.2 | 11.8 | 35.9 | 16.9 | 11.9 | 2.9 | 3.6 |
| NoTE_172 | 364.7 | 0.0 | 1.1 | 1.4 | 5.4 | 5.5 | 23.1 | 37.6 | 10.1 | 15.1 | 0.6 | 2.6 |
| NoTE_232 | 429.2 | 0.0 | 4.5 | 3.0 | 15.9 | 12.4 | 24.8 | 23.8 | 8.4 | 6.6 | 0.7 | 7.5 |
| NoTE_292 | 460.2 | 0.0 | 2.8 | 2.3 | 12.0 | 10.8 | 21.7 | 28.9 | 10.6 | 9.1 | 1.8 | 5.1 |
| NoTE_322 | 441.5 | 0.0 | 4.5 | 3.0 | 16.0 | 11.9 | 24.5 | 23.4 | 9.0 | 6.7 | 1.0 | 7.5 |
| NoTE_352 | 299.2 | 0.0 | 3.7 | 2.2 | 10.2 | 7.2 | 26.3 | 30.9 | 9.1 | 9.8 | 0.7 | 5.9 |
| NoTE_382 | 349.3 | 0.0 | 1.5 | 1.6 | 5.9 | 5.7 | 21.2 | 37.5 | 11.2 | 14.6 | 0.8 | 3.1 |
| (xxvi) NoTE_1 (V204W) | 409.9 | 1.5 | 9.3 | 8.8 | 17.1 | 14.7 | 9.8 | 21.1 | 8.6 | 4.8 | 4.3 | 18.1 |
| (xxvii) NoTE_172 (V204W) | 439.1 | 1.6 | 10.7 | 8.7 | 19.2 | 14.7 | 11.7 | 18.6 | 7.0 | 4.7 | 3.1 | 19.3 |
| (xxviii) NoTE_232 (V204W) | 440.0 | 1.5 | 12.0 | 6.9 | 22.7 | 14.4 | 15.6 | 14.5 | 6.6 | 3.8 | 1.9 | 19.0 |
| (xxix) NoTE_292 (V204W) | 406.6 | 1.7 | 13.4 | 7.9 | 22.4 | 15.0 | 14.2 | 13.7 | 6.6 | 3.1 | 2.0 | 21.3 |
| (xxx) NoTE_322 (V204W) | 370.3 | 1.9 | 14.5 | 8.1 | 22.9 | 14.8 | 14.2 | 12.7 | 6.4 | 2.6 | 1.9 | 22.7 |
| (xxxi) NoTE_352 (V204W) | 342.0 | 1.9 | 14.4 | 7.8 | 22.7 | 14.3 | 14.9 | 12.7 | 6.7 | 2.8 | 1.8 | 22.2 |
| (xxxii) NoTE_382 (V204W) | 354.0 | 1.8 | 9.7 | 6.2 | 19.3 | 12.6 | 13.8 | 18.9 | 9.2 | 5.6 | 2.9 | 16.0 |

As shown in Table 11, also when the amino acid at the N-terminal of the NoTE was modified so as to have various lengths, in comparison with the transformant having the introduced plasmids for wild type NoTE expression, the ratio of C10 fatty acid and C12 fatty acids (C12:n) each in the total amount of fatty acids significantly increased in the transformants having the introduced plasmids for NoTE variant expression constructed in such a manner that the amino acid of the 204th position of the amino acid sequence set forth in SEQ NO: 1 was substituted with tryptophan.

As described above, the transformant in which productivity of the fatty acids having the specific number of carbon atoms is improved can be prepared by introducing the gene encoding the protein as specified in the present Invention into the host. Further, productivity of the specific fatty acids can be improved by culturing this transformant.

What is claimed is:

1. A method of producing a lipid, comprising the steps of:
introducing a gene encoding any one of the following proteins (A) to (C) into a prokaryotic or eukaryotic microorganism or plant host cell, thereby obtaining a transformant,
culturing the transformant and expressing the gene, and producing the lipid,
wherein proteins (A) to (C) are:
(A) A protein consisting of the amino acid sequence of the 128th to 287th positions set forth in SEQ ID NO: 1 but in which at least one of the glycine at the 203rd position or the valine at the 204th position set forth in SEQ ID NO: 1 is substituted with tryptophan;
(B) A protein consisting of:
(i) an amino acid sequence having at least 90% sequence identity with the amino acid sequence of the 128th to 287th positions set forth in SEQ ID NO: 1,
(ii) the amino acid sequence of part (i) having at least 90% sequence identity with the amino acids sequence of the 128th to 287th positions set forth in SEQ ID NO:1 and in which 1 to 8 amino acids are deleted, substituted, inserted or added,
wherein, in each of protein (B)(i)-(B)(ii), at least one of the amino acids corresponding to the 203rd position or the 204th position set forth in SEQ ID NO: 1 is substituted with tryptophan, and
wherein protein (B) has acyl-ACP thioesterase activity; and
(C) A protein comprising the amino acid sequence of protein (A) or (B) and that has acyl-ACP thioesterase activity.

2. The method of claim 1, wherein, in the amino acid sequence of protein (B)(i) or (B)(ii), the glycine at the 203rd position set forth in SEQ ID NO: 1 or the amino acid corresponding to this position is substituted with tryptophan, and the valine at the 204th position set forth in SEQ ID NO: 1 or the amino acid corresponding to this position is substituted with tryptophan or phenylalanine.

3. The method of claim 1, wherein, in the amino acid sequence of protein (A) or (B), the glycine of the 203rd position set forth in SEQ ID NO: 1 or the amino acid corresponding to this position is substituted with tryptophan, and the valine of the 204th position set forth in SEQ ID NO: 1 or the amino acid corresponding to this position is substituted with tryptophan.

4. The method of claim 1, wherein the amino acid sequence of protein (B)(i) or (B)(ii), further contains at least one substitution selected from the group consisting of the following amino acid substitutions (Ca) to (Cg):
(Ca) The leucine of the 143rd position set forth in SEQ ID NO: 1 or the amino acid corresponding to this position is substituted with proline;
(Cb) The histidine of the 146th position set forth in SEQ ID NO: 1 or the amino acid corresponding to this position is substituted with asparagine or serine;
(Cc) The glycine of the 160th position set forth in SEQ ID NO: 1 or the amino acid corresponding to this position is substituted with alanine;
(Cd) The methionine of the 202nd position set forth in SEQ ID NO: 1 or the amino acid corresponding to this position is substituted with phenylalanine, histidine, leucine, glutamine or valine;
(Ce) The glycine of the 212th position set forth in SEQ ID NO: 1 or the amino acid corresponding to this position is substituted with proline;
(Cf) The asparagine of the 213th position set forth in SEQ ID NO: 1 or the amino acid corresponding to this position is substituted with tyrosine; and
(Cg) The proline of the 281st position set forth in SEQ ID NO: 1 or the amino acid corresponding to this position is substituted with glutamine.

5. The method of claim 1, wherein the gene encoding proteins (A) to (C) consists of following DNAs (A1) to (C1), respectively:
(A1) A DNA encoding protein (A), the DNA's sequence consisting of the nucleotide sequence of the 382nd to 864th positions set forth in SEQ ID NO: 2, but in which at least one set of nucleotides at the 607th to 609th positions or at the 610th to 612th positions set forth in SEQ ID NO: 2 is substituted with nucleotides encoding tryptophan;

(B1) A DNA encoding protein (B), the DNA's sequence consisting of a nucleotide sequence having at least 76% sequence identity with the nucleotide sequence of the 382nd to 864th positions set forth in SEQ ID NO: 2, in which at least one set of nucleotides corresponding to the 607th to 609th positions or corresponding to the 610th to 612th positions set forth in SEQ ID NO: 2 is substituted with nucleotides encoding tryptophan, wherein protein (B) consists of (i) an amino acid sequence having at least 90% sequence identity with the amino acid sequence of the 128th to 287th positions set forth in SEQ ID NO: 1, or (ii) the amino acid sequence of protein B of part (i) having at least 90% sequence identity with the amino acids sequence of the 128th to 287th positions set forth in SEQ ID NO:1 and in which 1 to 8 amino acids are deleted, substituted, inserted or added, wherein the DNA encodes a protein having acyl-ACP thioesterase activity;

and (C1) A DNA encoding protein (C), the DNA's sequence comprising the nucleotide sequence of DNA (A1) or (B1), wherein the DNA encodes a protein having acyl-ACP thioesterase activity.

6. The method of claim 1, wherein the host cell is a microorganism.

7. The method of claim 6, wherein the microorganism is a microalga.

8. The method of claim 7, wherein the microalga is an alga belonging to the genus *Nannochloropsis*.

9. The method of claim 6, wherein the microorganism is *Escherichia coli*.

10. The method of claim 1, wherein the lipid contains a fatty acid having 8, 10 or 12 carbon atoms, or an ester thereof.

11. A protein specified in any one of the following items (A) to (C):

(A) A protein consisting of the amino acid sequence of the 128th to 287th positions set forth in SEQ ID NO: 1 but in which at least one of the glycine at the 203rd position or the valine at the 204th position set forth in SEQ ID NO: 1 is substituted with tryptophan;

(B) A protein consisting of:
(i) an amino acid sequence having at least 90% sequence identity with the amino acid sequence of the 128th to 287th positions set forth in SEQ ID NO: 1,
(ii) the amino acid sequence of part (i) having at least 90% sequence identity with the amino acids sequence of the 128th to 287th positions set forth in SEQ ID NO:1 and in which 1 to 8 amino acids are deleted, substituted, inserted or added,
wherein, in each of protein (B)(i)-(B)(ii), at least one of the amino acids corresponding to the 203rd position or the 204th position set forth in SEQ ID NO: 1 is substituted with tryptophan
and wherein protein (B) has acyl-ACP thioesterase activity;

and (C) A protein comprising the amino acid sequence of protein (A) or (B) and wherein protein (C) has acyl-ACP thioesterase activity.

12. A gene encoding:

(A) A protein consisting of the amino acid sequence of the 128th to 287th positions set forth in SEQ ID NO: 1 but in which at least one of the glycine at the 203rd position or the valine at the 204th position set forth in SEQ ID NO: 1 is substituted with tryptophan;

(B) A protein consisting of:
(i) an amino acid sequence having at least 90% sequence identity with the amino acid sequence of the 128th to 287th positions set forth in SEQ ID NO: 1,
(ii) the amino acid sequence of part (i) having at least 90% sequence identity with the amino acids sequence of the 128th to 287th positions set forth in SEQ ID NO:1 and in which 1 to 8 amino acids are deleted, substituted, inserted or added,
wherein, in each of protein (B)(i)-(B)(ii), at least one of the amino acids corresponding to the 203rd position or the 204th position set forth in SEQ ID NO: 1 is substituted with tryptophan
and (C) A protein comprising the amino acid sequence of protein (A) or (B) and having acyl-ACP thioesterase activity.

13. The gene of claim 12, wherein the gene consists of a DNA as specified in any one of the following items (A1) to (C1):

(A1) A DNA encoding protein (A), the DNA's sequence consisting of the nucleotide sequence of the 382nd to 864th positions set forth in SEQ ID NO: 2, in which at least one set of nucleotides at the 607th to 609th positions or at the 610th to 612th positions set forth in SEQ ID NO: 2 is substituted with nucleotides encoding tryptophan;

(B1) A DNA encoding protein (B), the DNA's sequence consisting of a nucleotide sequence having at least 76% sequence identity with the nucleotide sequence of the 382nd to 864th positions set forth in SEQ ID NO: 2, in which at least one set of nucleotides corresponding to the 607th to 609th positions or corresponding to the 610th to 612th positions set forth in SEQ ID NO: 2 is substituted with nucleotides encoding tryptophan, wherein DNA (B1) encodes a protein having acyl-ACP thioesterase activity;

wherein protein (B) consists of (i) an amino acid sequence having at least 90% sequence identity with the amino acid sequence of the 128th to 287th positions set forth in SEQ ID NO: 1, or (ii) the amino acid sequence of protein B of part (i) having at least 90% sequence identity with the amino acids sequence of the 128th to 287th positions set forth in SEQ ID NO:1 and in which 1 to 8 amino acids are deleted, substituted, inserted or added, and (C1) A DNA encoding protein (C), the DNA's sequence comprising the nucleotide sequence of DNA (A1) or (B1), and wherein DNA (C) encodes a protein having acyl-ACP thioesterase activity.

14. A recombinant vector, comprising the gene of claim 12.

15. A transformant, which is obtained by introducing the gene of claim 12 into a prokaryotic or eukaryotic microorganism or plant host cell.

16. A method of modifying a lipid's fatty acid composition, comprising introducing the gene of claim 12 into a prokaryotic or eukaryotic microorganism or plant host cell to produce a transformant, culturing the transformant under conditions that express the protein encoded by the gene and that produce lipid, wherein the fatty acid composition of the lipid that is produced by the transformant is modified as compared to that of the host before introduction of the gene.

17. A method of enhancing productivity of a fatty acid having 8, 10 or 12 carbon atoms, comprising introducing the gene of claim 12 into a prokaryotic or eukaryotic microorganism or plant host cell to produce a transformant, culturing the transformant under conditions that express the protein encoded by the gene and that produce a fatty acid having 8, 10 or 12 carbon atoms, wherein productivity of a fatty acid having 8, 10 or 12 carbon atoms is enhanced in the transformant as compared to that of the host cell before introduction of the gene.

18. A transformant, which is obtained by introducing the recombinant vector of claim 14 into a prokaryotic or eukaryotic microorganism or plant host cell.

19. A method of modifying a lipid's fatty acid composition, comprising culturing the transformant of claim 18 under conditions that produce lipid, wherein the fatty acid composition of the lipid that is produced is modified as compared to that of the host cell before introduction of the gene.

20. A method of enhancing productivity of a fatty acid having 8, 10 or 12 carbon atoms, comprising culturing the transformant of claim 18 under conditions that produce fatty acid having 8, 10 or 12 carbon atoms, wherein productivity of a fatty acid having 8, 10 or 12 carbon atoms is enhanced in the transformant as compared to that of the host cell before introduction of the gene.

* * * * *